US012590171B2

(12) United States Patent
Qin et al.

(10) Patent No.: US 12,590,171 B2
(45) Date of Patent: Mar. 31, 2026

(54) ANTI-VHH DOMAIN ANTIBODIES AND USE THEREOF

(71) Applicant: Nanjing GenScript Biotech Co., Ltd., Nanjing (CN)

(72) Inventors: Xijian Qin, Nanjing (CN); Liwei Sun, Nanjing (CN); Wanyi Wang, Nanjing (CN); Guangwei Song, Nanjing (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 958 days.

(21) Appl. No.: 17/753,021

(22) PCT Filed: Sep. 27, 2020

(86) PCT No.: PCT/CN2020/118150
§ 371 (c)(1),
(2) Date: Feb. 15, 2022

(87) PCT Pub. No.: WO2021/057978
PCT Pub. Date: Apr. 1, 2021

(65) Prior Publication Data
US 2022/0281997 A1 Sep. 8, 2022

(30) Foreign Application Priority Data

Sep. 27, 2019 (CN) .......................... 201910922329.6

(51) Int. Cl.
| | |
|---|---|
| C07K 16/42 | (2006.01) |
| C07K 16/28 | (2006.01) |
| C12N 5/071 | (2010.01) |
| C12N 15/85 | (2006.01) |
| C12P 21/00 | (2006.01) |
| G01N 33/68 | (2006.01) |
| A61K 39/00 | (2006.01) |

(52) U.S. Cl.
CPC .......... C07K 16/42 (2013.01); C07K 16/2809 (2013.01); C12N 5/0682 (2013.01); C12N 15/85 (2013.01); C12P 21/005 (2013.01); G01N 33/6854 (2013.01); A61K 39/00 (2013.01); C12N 2800/107 (2013.01)

(58) Field of Classification Search
None
See application file for complete search history.

(56) References Cited

U.S. PATENT DOCUMENTS

2019/0233519 A1 8/2019 Zhang et al.

FOREIGN PATENT DOCUMENTS

CN 109843923 A 6/2019

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Rudikoff et al. (Proc. Natl. Acad. Sci. USA, 79: 1979-1983, Mar. 1982). (Year: 1982).*
Colman (Research in Immunology, 145:33-36, 1994). (Year: 1994).*
Examiner prepared alignment of antibody Vh domains, 1 page, 2025. (Year: 2025).*
Examiner prepared alignment of antibody Vl domains, 1 page, 2025. (Year: 2025).*
Examiner prepared alignment of Vhh domains, 1 page, 2025. (Year: 2025).*
"MonoRabTM Rabbit Anti-Camelid VHH Antibody [iFluor488], MAb.," GenScript, May 5, 2017 (May 5, 2017).
"Jackson ImmunoResearch: Jackson Alpaca Family-Nanobody VHH Newly Launched," Xibao Biotechnology (Sep. 26, 2019).
"Accelerating Nanobody Production Using Polyclonal Anti-VHH Antibodies," (Sep. 13, 2019).
International Search Report (Form PCT/ISA/210) for International Patent Application No. PCT/CN2020/118150, issued from the International Searching Authority, date of mailing Dec. 30, 2020, with English-language translation, 7 pages.
Written Opinion of the International Searching Authority (Form PCT/ISA/237) for International Patent Application No. PCT/CN2020/118150, issued from the International Searching Authority, date of mailing Dec. 30, 2020, with English-language translation, 10 pages.
Katrin et al., "Conditional control of fluorescent protein degradation by an auxin-dependent nanobody," Nature Communications 9(1): 1-13 (2018).
Rudikoff et al., "Single amino acid substitution altering antigen-binding specificity," PNAS 79:1979-1983 (1982).
Winkler et al., "Changing the antigen binding specificity by single point mutations of an anti-p24 (HIV-1) antibody," J. Immunol. 165(8):4505-4514 (2000).
Chanier et al., "Nanobody engineering: toward next generation immunotherapies and immunoimaging of cancer," Antibodies 8(1):1-21 (2019).
Jena et al., "Chimeric Antigen Receptor (CAR)-Specific Monoclonal Antibody to Detect CD19-Specific T Cells in Clinical Trials," PLOS One 8(3): e57838 (2013).

* cited by examiner

Primary Examiner — Zachary S Skelding
(74) Attorney, Agent, or Firm — Ice Miller LLP

(57) ABSTRACT

The invention provides a group of anti-VHH domain antibodies and use thereof. The present invention further provides use of the described antibodies in the development, screening and purification of nano-antibodies, and use of the described antibodies in the field of immunotherapy.

18 Claims, 9 Drawing Sheets
Specification includes a Sequence Listing.

FR1-CDR1-FR2-CDR2-FR3-CDR3-FR4-6His
QVQLVESGGGSVQAGGSLRLSCAASGDSPSVNYMGWFRRAPEKQREEVASIYPT
GGTFYTDSVKGRFTISRDNAKNTLYLQMTALKPEDTAMYYCAAGKWGTDYWGQG
TQVIVSSHHHHHH

*Fig. 1*

| Number | Serum dilution ratio before fusion | ELISA OD450 | |
|---|---|---|---|
| | | Animal number: #6119 | Animal number: #563 |
| 1 | 1:1,000 | 2.039 | 2.924 |
| 2 | 1:2,000 | 2.016 | 2.819 |
| 3 | 1:4,000 | 1.965 | 2.782 |
| 4 | 1:8,000 | 1.886 | 2.645 |
| 5 | 1:16,000 | 1.734 | 2.286 |
| 6 | 1:32,000 | 1.576 | 2.062 |
| 7 | 1:64,000 | 1.323 | 1.637 |
| 8 | 1:128,000 | 1.013 | 1.162 |
| 9 | 1:256,000 | 0.752 | 0.790 |
| 10 | 1:512,000 | 0.488 | 0.528 |
| 11 | Blank | 0.064 | 0.136 |
| 12 | Blank | 0.066 | 0.143 |
| 13 | S/N | 0.1365 | 0.2919 |
| Titer | | >1:512,000 | >1:512,000 |

*Fig. 2*

| Number | Detection sample | ELISA OD450 | |
|---|---|---|---|
| | | Detection target 1: VHH-His | Detection target 2: His tag protein |
| 1 | Clone R166.C5 | 2.758 | 0.074 |
| 2 | Clone R166.G3 | 3.06 | 0.130 |
| 3 | Clone R166.F2 | 2.908 | 0.091 |
| 4 | Clone R166.G8 | 2.883 | 0.102 |
| 5 | Clone R166.H9 | 2.893 | 0.082 |
| 6 | Clone R166.D1 | 2.556 | 0.100 |
| 7 | Clone R166.G10 | 2.913 | 0.121 |
| 8 | Clone R166.H10 | 2.655 | 0.083 |
| 9 | Clone R166.F9 | 2.561 | 0.091 |
| 10 | Clone R166.G2 | 2.356 | 0.114 |
| 11 | Clone R166.E5 | 3.059 | 0.123 |
| 12 | Clone R166.E3 | 2.13 | 0.085 |
| 13 | Clone R166.H8 | 2.083 | 0.112 |
| 14 | Clone R166.E7 | 2.454 | 0.082 |
| 15 | Clone R166.A5 | 2.428 | 0.079 |
| 16 | Positive serum 1:1,000 | 2.953 | 0.747 |
| 17 | Anti-His antibody 1ug/ml | 2.906 | 2.858 |
| 18 | Blank | 0.073 | 0.056 |
| 19 | Blank | 0.110 | 0.095 |

*Fig. 3*

| Clone number | Dilution ratio of cell supernatant | | | | | Blank | Positive serum 1:1,000 |
|---|---|---|---|---|---|---|---|
| | Stock solution | 1:3 | 1:9 | 1:27 | 1:81 | | |
| Clone R166.C5 | 2.4 | 2.513 | 2.46 | 2.282 | 1.972 | 0.055 | 2.368 |
| Clone R166.G3 | 2.389 | 2.328 | 1.954 | 1.22 | 0.545 | 0.054 | 2.368 |
| Clone R166.F2 | 2.453 | 2.369 | 1.945 | 1.339 | 0.542 | 0.067 | 2.802 |
| Clone R166.G8 | 2.33 | 2.309 | 2.143 | 1.783 | 1.074 | 0.053 | 2.368 |
| Clone R166.H9 | 2.424 | 2.353 | 2.243 | 2.093 | 1.559 | 0.052 | 2.368 |
| Clone R166.D1 | 2.226 | 2.197 | 2.047 | 1.763 | 1.18 | 0.054 | 2.368 |
| Clone R166.G10 | 2.369 | 2.279 | 2.064 | 1.708 | 1.046 | 0.054 | 2.368 |
| Clone R166.H10 | 2.359 | 2.378 | 2.268 | 1.905 | 1.214 | 0.056 | 2.368 |
| Clone R166.F9 | 2.419 | 2.374 | 2.197 | 1.759 | 1.028 | 0.06 | 2.368 |
| Clone R166.G2 | 2.517 | 2.195 | 1.528 | 0.73 | 0.267 | 0.059 | 2.802 |
| Clone R166.E5 | 2.615 | 2.599 | 2.377 | 1.629 | 0.655 | 0.06 | 2.802 |
| Clone R166.E3 | 2.479 | 2.256 | 1.53 | 0.699 | 0.303 | 0.111 | 3.203 |
| Clone R166.H8 | 2.622 | 2.684 | 2.485 | 2.141 | 1.262 | 0.059 | 2.802 |
| Clone R166.E7 | 2.469 | 2.303 | 1.929 | 1.343 | 0.462 | 0.061 | 2.618 |
| Clone R166.A5 | 2.569 | 2.14 | 1.475 | 0.855 | 0.473 | 0.054 | 2.618 |

*Fig. 4*

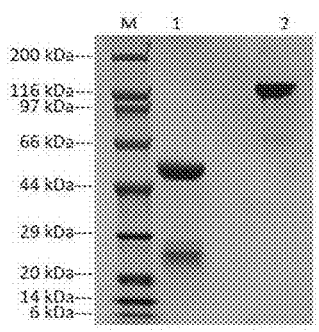

Purity detection of clone R166.C1 purified antibody by SDS-PAGE
Lane M: Protein Marker, TaKaRa, Cat.No.3452
Lane 1: reducing condition
Lane 2: non-reducing condition

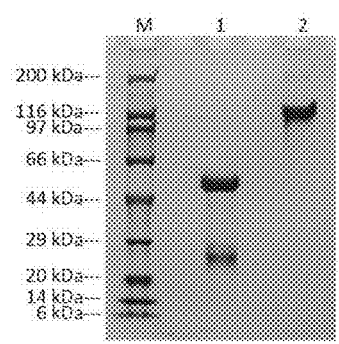

Purity detection of clone R166.C2 purified antibody by SDS-PAGE
Lane M: Protein Marker, TaKaRa, Cat.No.3452
Lane 1: reducing condition
Lane 2: non-reducing condition

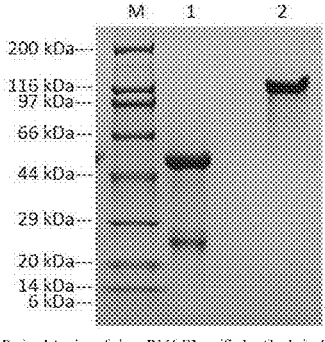

Purity detection of clone R166.F2 purified antibody by SDS-PAGE
Lane M: Protein Marker, TaKaRa, Cat.No.3452
Lane 1: reducing condition
Lane 2: non-reducing condition

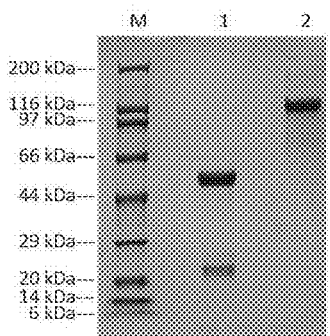

Purity detection of clone R166.G8 purified antibody by SDS-PAGE
Lane M: Protein Marker, TaKaRa, Cat.No.3452
Lane 1: reducing condition
Lane 2: non-reducing condition

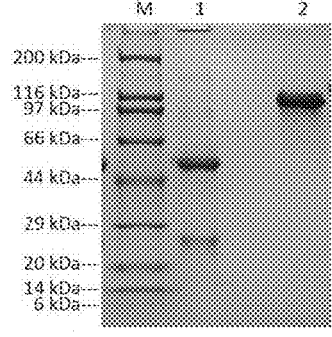

Purity detection of clone R166.H9 purified antibody by SDS-PAGE
Lane M: Protein Marker, TaKaRa, Cat.No.3452
Lane 1: reducing condition
Lane 2: non-reducing condition

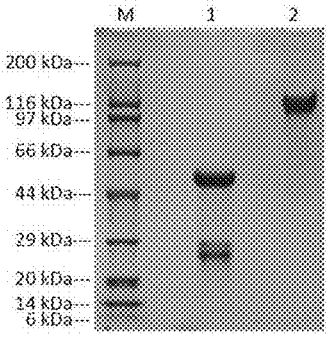

Purity detection of clone R166.D1 purified antibody by SDS-PAGE
Lane M: Protein Marker, TaKaRa, Cat.No.3452
Lane 1: reducing condition
Lane 2: non-reducing condition

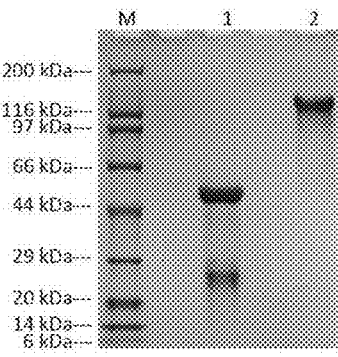

Purity detection of clone R166.G10 purified antibody by SDS-PAGE
Lane M: Protein Marker, TaKaRa, Cat.No.3452
Lane 1: reducing condition
Lane 2: non-reducing condition

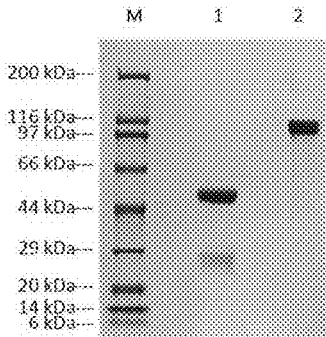

Purity detection of clone R166.H10 purified antibody by SDS-PAGE
Lane M: Protein Marker, TaKaRa, Cat.No.3452
Lane 1: reducing condition
Lane 2: non-reducing condition

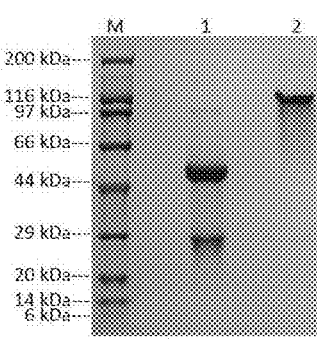

Purity detection of clone R166.F9 purified antibody by SDS-PAGE
Lane M: Protein Marker, TaKaRa, Cat.No.345
Lane 1: reducing condition
Lane 2: non-reducing condition

*Fig. 5a*

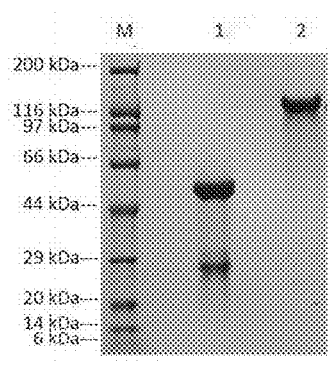

Purity detection of clone R166.G2 purified antibody by SDS-PAGE
Lane M: Protein Marker, TaKaRa, Cat.No.3452
Lane 1: reducing condition
Lane 2: non-reducing condition

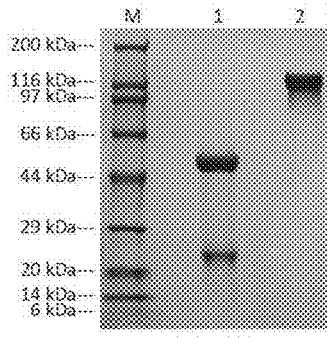

Purity detection of clone R166.E5 purified antibody by SDS-PAGE
Lane M: Protein Marker, TaKaRa, Cat.No.3452
Lane 1: reducing condition
Lane 2: non-reducing condition

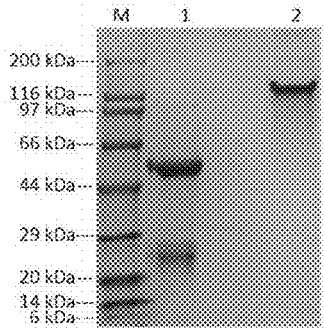

Purity detection of clone R166.E3 purified antibody by SDS-PAGE
Lane M: Protein Marker, TaKaRa, Cat.No.3452
Lane 1: reducing condition
Lane 2: non-reducing condition

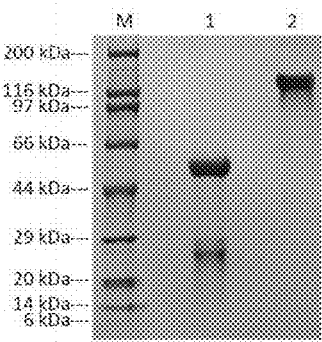

Purity detection of clone R166.B8 purified antibody by SDS-PAGE
Lane M: Protein Marker, TaKaRa, Cat.No.3452
Lane 1: reducing condition
Lane 2: non-reducing condition

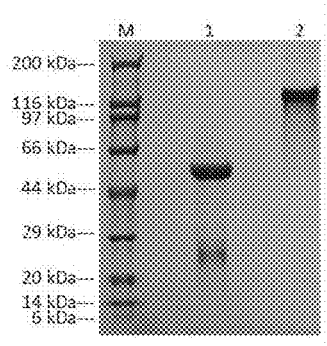

Purity detection of clone R166.E7 purified antibody by SDS-PAGE
Lane M: Protein Marker, TaKaRa, Cat.No.3452
Lane 1: reducing condition
Lane 2: non-reducing condition

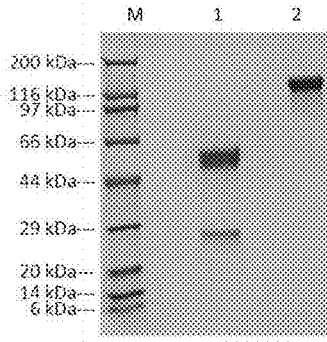

Purity detection of clone R166.A5 purified antibody by SDS-PAGE
Lane M: Protein Marker, TaKaRa, Cat.No.3452
Lane 1: reducing condition
Lane 2: non-reducing condition

*Fig. 5b*

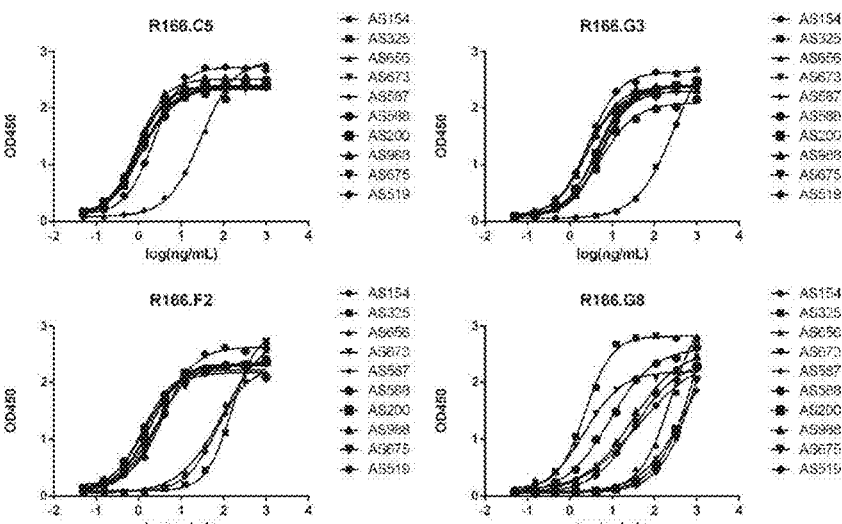

*Fig. 6a*

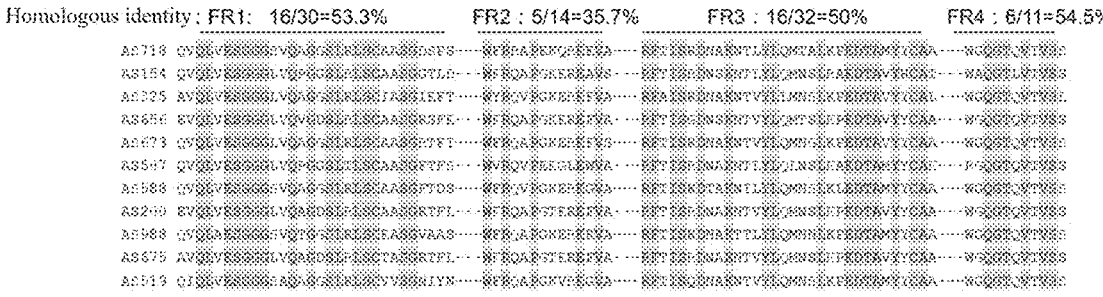
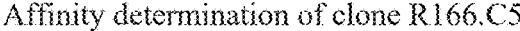
Identity of framework region: 49.4%
*Fig. 7*
Affinity determination of clone R166.C5
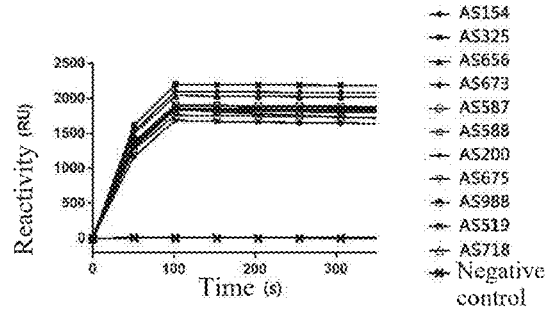
| Ligand | ka (1/Ms) | kd (1/s) | KD (M) |
|--------|-----------|----------|--------|
| AS154 | 8.49E+04 | 3.42E-05 | 4.02E-10 |
| AS325 | 1.16E+05 | 4.68E-07 | 4.04E-12 |
| AS656 | 1.11E+05 | 1.49E-07 | 1.34E-12 |
| AS673 | 1.14E+05 | 4.95E-07 | 4.36E-12 |
| AS587 | 9.49E+04 | 2.09E-04 | 2.20E-09 |
| AS588 | 1.00E+05 | 7.10E-07 | 7.09E-12 |
| AS200 | 1.24E+05 | 1.46E-06 | 1.18E-11 |
| AS988 | 9.74E+04 | 6.89E-07 | 7.08E-12 |
| AS675 | 1.22E+05 | 4.23E-06 | 3.45E-11 |
| AS519 | 1.01E+05 | 1.68E-07 | 1.66E-12 |
| AS718 | 1.06E+05 | 3.68E-07 | 3.47E-12 |
*Fig. 8*
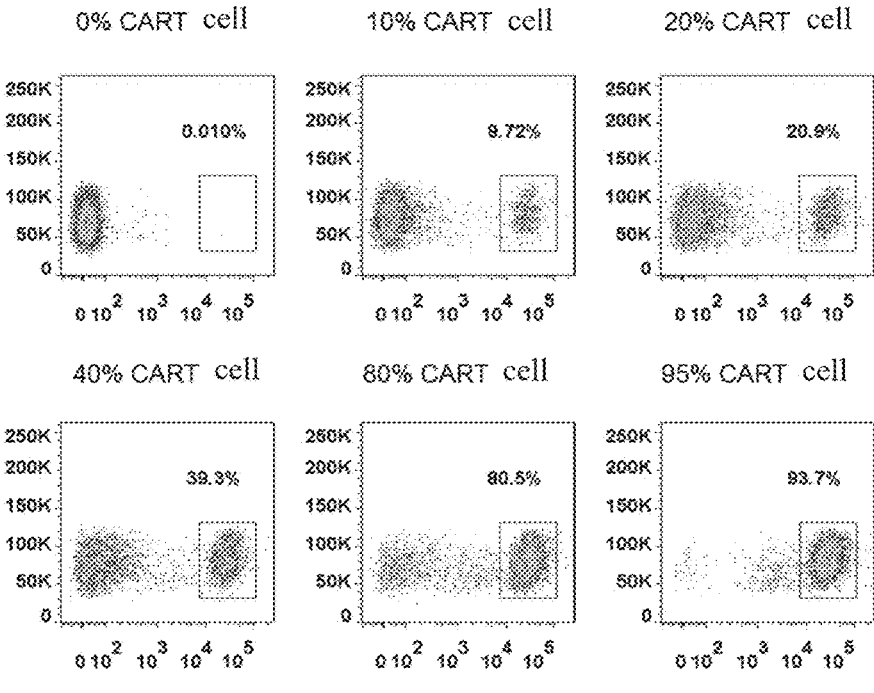
*Fig. 9*

Before magnetic separation of CART cell
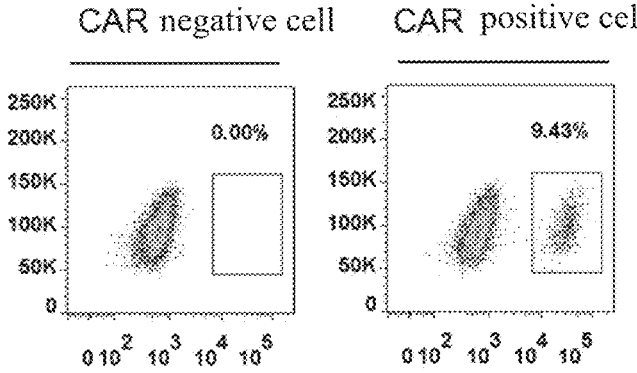
After magnetic separation of CART cell
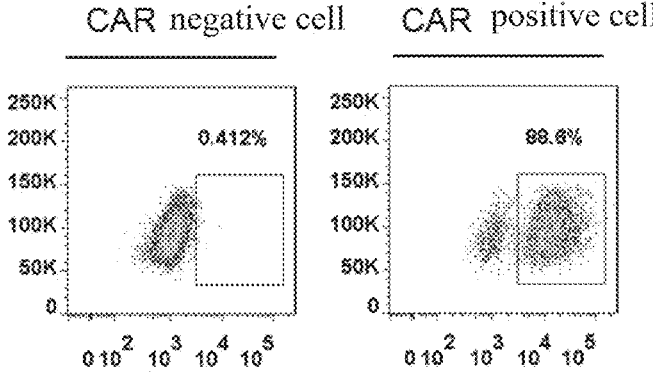
*Fig. 10*

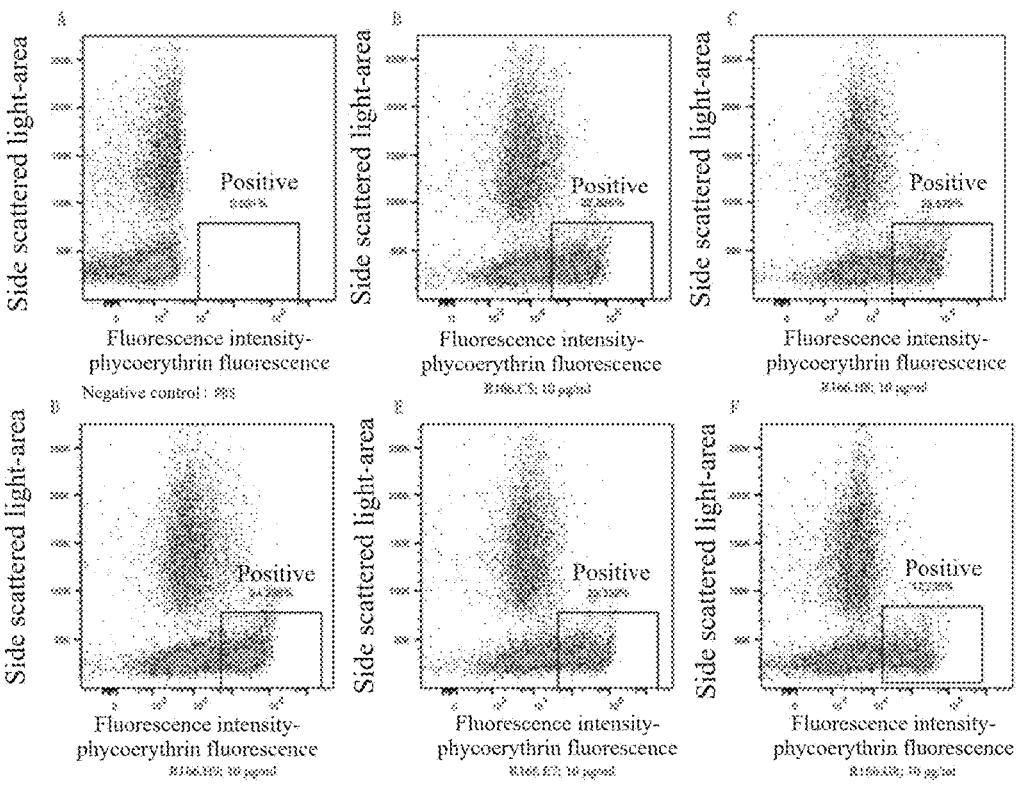

*Fig. 12*

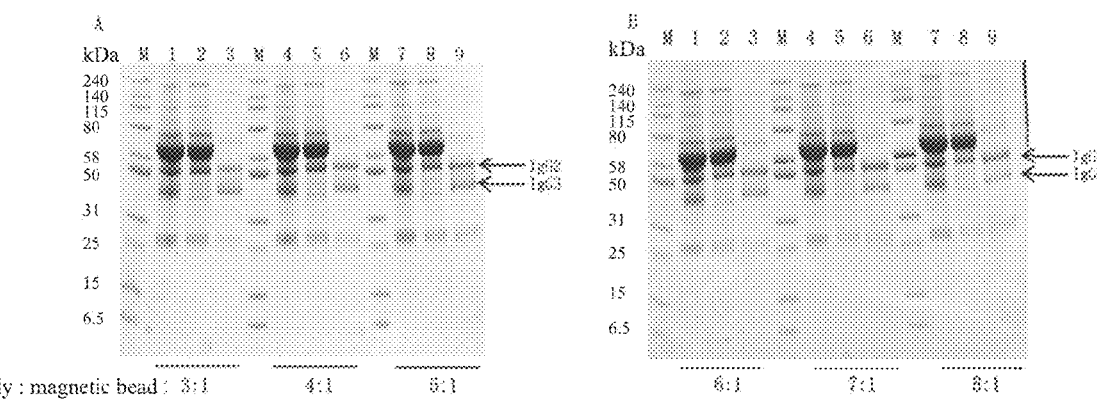

Lane M: protein molecular weight standard:
Lanes 1, 4 and 7: alpaca serum before purification, reduced;
Lanes 2, 5 and 8: effluent after purification, reduced;
Lanes 3, 6 and 9: eluate after purification, reduced;

Lane M: protein molecular weight standard:
Lanes 1, 4 and 7: alpaca serum before purification, reduced;
Lanes 2, 5 and 8: effluent after purification, reduced;
Lanes 3, 6 and 9: eluate after purification, reduced;

*Fig. 13*

ANTI-VHH DOMAIN ANTIBODIES AND USE THEREOF

CROSS-REFERENCE TO RELATED APPLICATION

This application is a Section 371 of International Application No. PCT/CN2020/118150, filed on Sep. 27, 2020, which published in the Chinese language on Apr. 1, 2021 under International Publication No. WO 2021/057978, which claims priority to CN201910922320.6, filed on Sep. 27, 2019. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "065824.13US1 Sequence Listing" and a creation date of Feb. 15, 2022 and having a size of 101 kb. The sequence listing is submitted via EFS-Web is part of the specification and is herein incorporated by reference in its entirety.

TECHNICAL FIELD

The present invention relates to a group of anti-VHH domain antibodies. The present invention also relates to methods for preparing and obtaining the antibodies. Moreover, the present invention relates to use of the antibodies in the development, screening and purification of nanobodies. The present invention also relates to use of the antibodies in the field of immunotherapy.

BACKGROUND ART

Camel-derived nanobody is also called single-domain antibody or variable domain of heavy chain of HCAb (VHH) and only comprises a variable region fragment of a camel-derived heavy-chain antibody, wherein the variable region fragment has a size of only about 15 kDa. The camel-derived nanobody can bind to an antigen with high affinity and high specificity and has very important application in the field of antibody drug development, immune cell therapy, etc.

In 1993, Hamers-Casterman et al. first found that heavy-chain antibodies (HCAbs) that lack light chains are present in camelid animal [C. Hamers, et al., Naturally occurring antibodies devoid of light chains. Nature, 1993. Vol 363: p 466-468], and the heavy-chain antibodies only contain heavy chain variable regions and CH2 and CH3 constant regions. The VHH variable region expressed by means of molecular cloning has very good stability and affinity and is currently known as the smallest antibody unit. On the basis of nanobody development technology, Ablynx has successfully developed and marketed the first therapeutic nanobody drug caplacizumab for the treatment of acquired thrombotic thrombocytopenic purpura (aTTP) [https://www.ablynx.com/rd-portfolio/clinical-programmes/caplacizumab/].

In addition, the camel-derived nanobody also has very important application in the field of immune cell therapy. LCAR-B38M of Nanjing Legend Biotech Co., Ltd. is the first cell treatment therapy in China that was approved by the cFDA for clinical application and is also the first project that was submitted and approved in both China and the United States. The project has shown amazing therapeutic effects as per the currently published data, which has important significance in the development of immune cell therapy in China. In this project, a unique nanobody is used to design a chimeric antigen receptor (CAR), which avoids the shortcomings of poor stability and low affinity of conventional scFv technical routes. With the development of immune cell therapy technology, nanobody has gained increasing interest of researchers.

Although nanobody has great significance in the field of antibody drug development and immune cell therapy, there is currently a lack of an antibody for identifying camel-derived nanobodies for better development of camel-derived nanobodies or for the optimization of the identification, sorting and magnetic separation of CART cells in immune cell therapy. The present invention develops a group of antibodies with high affinity, high specificity and high functionality for the camel-derived nanobodies, which effectively solves the above-mentioned problems and meets the needs in various application fields.

SUMMARY OF THE INVENTION

In one aspect, the present invention provides an antibody or an antigen-binding fragment thereof, which specifically binds to a VHH domain. In one embodiment, the VHH domain is a VHH domain of a camel-derived antibody. In one embodiment, the camel-derived antibody is a single-domain antibody or a heavy-chain antibody derived from *Camelus dromedarius, Camelus bactrianus, Vicugna pacos* or *Lama glama*.

In another aspect, the present invention provides an antibody or an antigen-binding fragment thereof. In some embodiments, the antibody or the antigen-binding fragment thereof disclosed in the present invention contains a heavy chain variable region (HCVR) and a light chain variable region (LCVR), wherein (A) the heavy chain variable region comprises heavy chain complementarity determining regions HCDR1, HCDR2 and HCDR3, wherein (a) the HCDR1 has a sequence selected from an amino acid sequence shown in SEQ ID NO: 1, 2, 3, 4, 5, 6, 7, 8, 9, 10, 11, 12, 13, 14 or 15 or an amino acid sequence having at least 90%, 91%, 92%, 93%, 94%, 95%, 96%, 97%, 98%, 99% or 100% identity thereto, (b) the HCDR2 has a sequence selected from an amino acid sequence shown in SEQ ID NO: 16, 17, 18, 19, 20, 21, 22, 23, 24, 25, 26, 27, 28, 29 or 30 or an amino acid sequence having at least 90%, 91%, 92%, 93%, 94%, 95%, 96%, 97%, 98%, 99% or 100% identity thereto, (c) the HCDR3 has a sequence selected from an amino acid sequence shown in SEQ ID NO: 31, 32, 33, 34, 35, 36, 37, 38, 39, 40, 41, 42, 43, 44 or 45 or an amino acid sequence having at least 90%, 91%, 92%, 93%, 94%, 95%, 96%, 97%, 98%, 99% or 100% identity thereto, and (d) the heavy chain complementarity determining region HCDR contains the amino acid sequences of (a), (b) and (c) having no more than 3 amino acid substitutions, deletions or insertions at one or more positions; and (B) the light chain variable region comprises light chain complementarity determining regions LCDR1, LCDR2 and LCDR3, wherein (e) the LCDR1 has a sequence selected from an amino acid sequence shown in SEQ ID NO: 46, 47, 48, 49, 50, 51, 52, 53, 54, 55, 56, 57, 58, 59 or 60 or an amino acid sequence having at least 90%, 91%, 92%, 93%, 94%, 95%, 96%, 97%, 98%, 99% or 100% identity thereto, (f) the LCDR2 has a sequence selected from an amino acid sequence shown in SEQ ID NO: 61, 62, 63, 64, 65, 66, 67, 68, 69, 70, 71, 72, 73, 74 or 75 or an amino acid sequence having at least 90%, 91%, 92%, 93%, 94%, 95%, 96%, 97%, 98%, 99% or 100% identity thereto, (g) the LCDR3 has a sequence selected from an amino acid sequence shown in SEQ ID NO: 76, 77, 78, 79, 80, 81, 82, 83, 84, 85, 86, 87, 88, 89 or 90 or an amino acid sequence having at least 90%, 91%, 92%, 93%, 94%, 95%, 96%, 97%, 98%, 99% or 100% identity thereto, (h) the light chain complementarity determining region LCDR contains the amino acid sequences of (e), (f) and (g) having no more than 3 amino acid substitutions, deletions or insertions at one or more positions.

In a further embodiment, the antibody or the antigen-binding fragment thereof disclosed in the present invention contains (1) HCDR1 shown in SEQ ID NO: 1, HCDR2 shown in SEQ ID NO: 16, HCDR3 shown in SEQ ID NO: 31, LCDR1 shown in SEQ ID NO: 46, LCDR2 shown in SEQ ID NO: 61 and LCDR3 shown in SEQ ID NO: 76; (2) HCDR1 shown in SEQ ID NO: 2, HCDR2 shown in SEQ ID NO: 17, HCDR3 shown in SEQ ID NO: 32, LCDR1 shown in SEQ ID NO: 47, LCDR2 shown in SEQ ID NO: 62 and LCDR3 shown in SEQ ID NO: 77; (3) HCDR1 shown in SEQ ID NO: 3, HCDR2 shown in SEQ ID NO: 18, HCDR3 shown in SEQ ID NO: 33, LCDR1 shown in SEQ ID NO: 48, LCDR2 shown in SEQ ID NO: 63 and LCDR3 shown in SEQ ID NO: 78; (4) HCDR1 shown in SEQ ID NO: 4, HCDR2 shown in SEQ ID NO: 19, HCDR3 shown in SEQ ID NO: 34, LCDR1 shown in SEQ ID NO: 49, LCDR2 shown in SEQ ID NO: 64 and LCDR3 shown in SEQ ID NO: 79; (5) HCDR1 shown in SEQ ID NO: 5, HCDR2 shown in SEQ ID NO: 20, HCDR3 shown in SEQ ID NO: 35, LCDR1 shown in SEQ ID NO: 50, LCDR2 shown in SEQ ID NO: 65 and LCDR3 shown in SEQ ID NO: 80; (6) HCDR1 shown in SEQ ID NO: 6, HCDR2 shown in SEQ ID NO: 21, HCDR3 shown in SEQ ID NO: 36, LCDR1 shown in SEQ ID NO: 51, LCDR2 shown in SEQ ID NO: 66 and LCDR3 shown in SEQ ID NO: 81; (7) HCDR1 shown in SEQ ID NO: 7, HCDR2 shown in SEQ ID NO: 22, HCDR3 shown in SEQ ID NO: 37, LCDR1 shown in SEQ ID NO: 52, LCDR2 shown in SEQ ID NO: 67 and LCDR3 shown in SEQ ID NO: 82; (8) HCDR1 shown in SEQ ID NO: 8, HCDR2 shown in SEQ ID NO: 23, HCDR3 shown in SEQ ID NO: 38, LCDR1 shown in SEQ ID NO: 53, LCDR2 shown in SEQ ID NO: 68 and LCDR3 shown in SEQ ID NO: 83; (9) HCDR1 shown in SEQ ID NO: 9, HCDR2 shown in SEQ ID NO: 24, HCDR3 shown in SEQ ID NO: 39, LCDR1 shown in SEQ ID NO: 54, LCDR2 shown in SEQ ID NO: 69 and LCDR3 shown in SEQ ID NO: 84; (10) HCDR1 shown in SEQ ID NO: 10, HCDR2 shown in SEQ ID NO: 25, HCDR3 shown in SEQ ID NO: 40, LCDR1 shown in SEQ ID NO: 55, LCDR2 shown in SEQ ID NO: 70 and LCDR3 shown in SEQ ID NO: 85; (11) HCDR1 shown in SEQ ID NO: 11, HCDR2 shown in SEQ ID NO: 26, HCDR3 shown in SEQ ID NO: 41, LCDR1 shown in SEQ ID NO: 56, LCDR2 shown in SEQ ID NO: 71 and LCDR3 shown in SEQ ID NO: 86; (12) HCDR1 shown in SEQ ID NO: 12, HCDR2 shown in SEQ ID NO: 27, HCDR3 shown in SEQ ID NO: 42, LCDR1 shown in SEQ ID NO: 57, LCDR2 shown in SEQ ID NO: 72 and LCDR3 shown in SEQ ID NO: 87; (13) HCDR1 shown in SEQ ID NO: 13, HCDR2 shown in SEQ ID NO: 28, HCDR3 shown in SEQ ID NO: 43, LCDR1 shown in SEQ ID NO: 58, LCDR2 shown in SEQ ID NO: 73 and LCDR3 shown in SEQ ID NO: 88; (14) HCDR1 shown in SEQ ID NO: 14, HCDR2 shown in SEQ ID NO: 29, HCDR3 shown in SEQ ID NO: 44, LCDR1 shown in SEQ ID NO: 59, LCDR2 shown in SEQ ID NO: 74 and LCDR3 shown in SEQ ID NO: 89; or (15) HCDR1 shown in SEQ ID NO: 15, HCDR2 shown in SEQ ID NO: 30, HCDR3 shown in SEQ ID NO: 45, LCDR1 shown in SEQ ID NO: 60, LCDR2 shown in SEQ ID NO: 75 and LCDR3 shown in SEQ ID NO: 90.

In some embodiments, the antibody or the antigen-binding fragment thereof disclosed in the present invention comprises a heavy chain variable region (HCVR), wherein the amino acid sequence of the heavy chain variable region is selected from an amino acid sequence shown in SEQ ID NO: 91, 92, 93, 94, 95, 96, 97, 98, 99, 100, 101, 102, 103, 104 or 105 or an amino acid sequence having at least 90%, 91%, 92%, 93%, 94%, 95%, 96%, 97%, 98%, 99% or 100% identity thereto.

In some embodiments, the antibody or the antigen-binding fragment thereof disclosed in the present invention comprises a light chain variable region (LCVR), wherein the amino acid sequence of the light chain variable region is selected from an amino acid sequence shown in SEQ ID NO: 106, 107, 108, 109, 110, 111, 112, 113, 114, 115, 116, 117, 118, 119 or 120 or an amino acid sequence having at least 90%, 91%, 92%, 93%, 94%, 95%, 96%, 97%, 98%, 99% or 100% identity thereto.

In a further embodiment, the antibody or the antigen-binding fragment thereof disclosed in the present invention contains (1) a heavy chain variable region shown in SEQ ID NO: 91 and a light chain variable region shown in SEQ ID NO: 106; (2) a heavy chain variable region shown in SEQ ID NO: 92 and a light chain variable region shown in SEQ ID NO: 107; (3) a heavy chain variable region shown in SEQ ID NO: 93 and a light chain variable region shown in SEQ ID NO: 108; (4) a heavy chain variable region shown in SEQ ID NO: 94 and a light chain variable region shown in SEQ ID NO: 109; (5) a heavy chain variable region shown in SEQ ID NO: 95 and a light chain variable region shown in SEQ ID NO: 110; (6) a heavy chain variable region shown in SEQ ID NO: 96 and a light chain variable region shown in SEQ ID NO: 111; (7) a heavy chain variable region shown in SEQ ID NO: 97 and a light chain variable region shown in SEQ ID NO: 112; (8) a heavy chain variable region shown in SEQ ID NO: 98 and a light chain variable region shown in SEQ ID NO: 113; (9) a heavy chain variable region shown in SEQ ID NO: 99 and a light chain variable region shown in SEQ ID NO: 114; (10) a heavy chain variable region shown in SEQ ID NO: 100 and a light chain variable region shown in SEQ ID NO: 115; (11) a heavy chain variable region shown in SEQ ID NO: 101 and a light chain variable region shown in SEQ ID NO: 116; (12) a heavy chain variable region shown in SEQ ID NO: 102 and a light chain variable region shown in SEQ ID NO: 117; (13) a heavy chain variable region shown in SEQ ID NO: 103 and a light chain variable region shown in SEQ ID NO: 118; (14) a heavy chain variable region shown in SEQ ID NO: 104 and a light chain variable region shown in SEQ ID NO: 119; or (15) a heavy chain variable region shown in SEQ ID NO: 105 and a light chain variable region shown in SEQ ID NO: 120.

In any one of the described embodiments, the antibody or the antigen-binding fragment thereof of the present invention specifically binds to a VHH domain. In one embodiment, the VHH domain is a VHH domain of a camel-derived antibody. That is, the antibody or the antigen-binding fragment thereof specified in the described sequence has good binding ability to a camel-derived single-domain antibody or a camel-derived heavy-chain antibody. In one embodiment, the camel-derived antibody is a single-domain antibody or a heavy-chain antibody derived from *Camelus dromedarius, Camelus bactrianus, Vicugna pacos* or *Lama glama.*

In one embodiment of the described aspects, the antibody or the antigen-binding fragment thereof of the present invention binds to the VHH domain at a framework region. In one embodiment of the described aspects, the antibody or the antigen-binding fragment thereof of the present invention binds to the VHH domain at a conformational epitope. In one embodiment of the described aspects, the antibody or the antigen-binding fragment thereof of the present invention binds to the VHH domain at a conformational epitope in a framework region.

In one embodiment of the described aspects, the antibody or the antigen-binding fragment thereof of the present invention specifically binds to a VHH domain shown in any one of SEQ ID NOs: 241 and 246-255, or a VHH domain having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% amino acid sequence identity to any one of SEQ ID NOs: 241 and 246-255, or a consensus sequence of SEQ ID NOs: 241 and 246-255. In one embodiment of the described aspects, the antibody or the antigen-binding fragment thereof of the present invention specifically binds to a framework region of the VHH domain shown in any one of SEQ ID NOs: 241 and 246-255, or a framework region having at least 45%, at least 50%, at least 55%, at least 60%, at least 65%, at least 70%, at least 75%, at least 80%, at least 85%, at least 90%, at least 95%, at least 96%, at least 97%, at least 98% or at least 99% amino acid sequence identity to the framework region of the VHH domain shown in any one of SEQ ID NOs: 241 and 246-255, or a consensus framework sequence of SEQ ID NOs: 241 and 246-255.

In one embodiment of the described aspects, the antibody or the antigen-binding fragment thereof of the present invention specifically binds to a VHH domain, for example, a VHH domain shown in any one of SEQ ID NOs: 241 and 246-255, or a VHH domain having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% amino acid sequence identity to any one of SEQ ID NOs: 241 and 246-255, or a consensus sequence of SEQ ID NOs: 241 and 246-255, or a framework region comprising the VHH domain shown in any one of SEQ ID NOs: 241 and 246-255, or a VHH domain of a framework region having at least 45%, at least 50%, at least 55%, at least 60%, at least 65%, at least 70%, at least 75%, at least 80%, at least 85%, at least 90%, at least 95%, at least 96%, at least 97%, at least 98% or at least 99% amino acid sequence identity to the framework region of the VHH domain shown in any one of SEQ ID NOs: 241 and 246-255, or a consensus framework sequence of SEQ ID NOs: 241 and 246-255 with a binding affinity $K_D$ of 10 nM to 1 pM, for example, 1 nM to 10 pM, for example, 1 pM to 10 pM, for example, 1 pM to 5 pM. In one embodiment, the binding affinity is determined by surface plasmon resonance (SPR) technique.

In one embodiment of the described aspects, the antibody or the antigen-binding fragment thereof of the present invention binds to the VHH domain at an epitope comprising one or more positions selected from: positions 3, 4, 6-10, 13, 15, 17, 18, 20-22, 25, 26, 36, 38, 41, 46, 48, 66 67, 69, 70, 72, 75, 79, 80, 82C, 85-88, 90, 92, 93, 105-107, 109, 111 and 112 according to Kabat numbering; or the positions corresponding to positions 3, 4, 6-10, 13, 15, 17, 18, 20-22, 25, 26, 36, 38, 41, 46, 48, 66, 67, 69-70, 72, 75, 79, 80, 85, 88-91, 93, 95, 96, 107-109, 111, 113 and 114 of SEQ ID NO: 241 according to sequential numbering (see FIG. 11).

In one embodiment of the described aspects, the antibody or the antigen-binding fragment thereof of the present invention binds to the VHH domain at an epitope comprising one or more positions selected from: positions 3-10, 13, 15, 17-22, 25, 26, 36-43, 45, 46, 48, 49, 66-70, 72, 73, 75-82, 82B-88, 90-94 and 103-113 according to Kabat numbering; or the positions corresponding to positions 3-10, 13, 15, 17-22, 25, 26, 36-43, 45, 46, 48, 49, 66-70, 72, 73, 75-82, 84-91, 93-97 and 105-115 of SEQ ID NO: 248 and/or 255 according to sequential numbering.

In one embodiment of the described aspects, the antibody or the antigen-binding fragment thereof of the present invention binds to the VHH domain at an epitope comprising one or more positions selected from: positions 3-10, 13, 15, 17-22, 25, 26, 36-38, 40, 41, 43, 45, 46, 48, 49, 66-70, 72, 73, 75-77, 79-82, 82C-88, 90-94, 103-109 and 111-113 according to Kabat numbering; or the positions corresponding to positions 3-10, 13, 15, 17-22, 25, 26, 36-38, 40, 41, 43, 45, 46, 48, 49, 66-70, 72, 73, 75-77, 79-82, 85-91, 93-97, 105-111 and 113-115 of SEQ ID NO: 248 and/or 255 according to sequential numbering.

In one embodiment of the described aspects, the antibody or the antigen-binding fragment thereof of the present invention binds to the VHH domain at an epitope comprising one or more positions selected from: positions 39, 42, 78, 82B and 110 according to Kabat numbering; or the positions corresponding to positions 39, 42, 78, 84 and 112 of SEQ ID NO: 248 and/or 255 according to sequential numbering.

In another aspect, the present invention encompasses an antibody or an antigen-binding fragment thereof, which binds to the same epitope as the above-mentioned antibody or antigen-binding fragment thereof. In another aspect, the present invention encompasses an antibody or an antigen-binding fragment thereof, which competes for binding with the above-mentioned antibody or antigen-binding fragment thereof.

In one aspect, the antibody or the antigen-binding fragment thereof of the present invention is a naked antibody or an antigen-binding fragment thereof.

In one aspect, the present invention provides one or more polynucleotides, which encode the antibody or the antigen-binding fragment thereof of the present invention. In one aspect, the present invention provides one or more vectors, which comprise the polynucleotide of the present invention. In one embodiment, the vector is selected from a cloning vector and an expression vector. In one aspect, the present invention provides a host cell, which comprises the polynucleotide or vector of the present invention. In one embodiment, the host cell is selected from a prokaryotic cell, a yeast cell, an insect cell or a mammalian cell. In one aspect, the present invention provides a method for producing an antibody or an antigen-binding fragment thereof, which comprises culturing the host cell of the present invention under the condition suitable for antibody production to express the antibody or the antigen-binding fragment thereof. In one embodiment, the method further comprises recycling the antibody or the antigen-binding fragment thereof.

In one aspect, the present invention provides a conjugate, which comprises the antibody or the antigen-binding fragment thereof of the present invention. In one embodiment, the antibody or the antigen-binding fragment thereof is coupled with fluorescein, biotin, an enzyme, an agarose resin, a magnetic bead or a biochip.

In one aspect, the present invention provides a kit, which comprises a container comprising the antibody or the antigen-binding fragment thereof or the conjugate of the present invention.

In one aspect, the present invention provides a method for detecting a VHH domain, which comprises adding the antibody or the antigen-binding fragment thereof or the conjugate of the present invention to a sample that is known or suspected to contain the VHH domain and detecting a complex formed between the antibody or the antigen-binding fragment thereof or the conjugate and the VHH domain.

In one aspect, the present invention provides a method for separating a VHH domain, which comprises adding the antibody or the antigen-binding fragment thereof or the conjugate of the present invention to a sample that is known or suspected to contain the VHH domain and separating a complex formed between the antibody or the antigen-binding fragment thereof or the conjugate and the VHH domain.

In one embodiment, the VHH domain is in a camel-derived antibody. In one embodiment, the camel-derived antibody is a single-domain antibody or a heavy-chain antibody derived from *Camelus dromedarius, Camelus bactrianus, Vicugna pacos* or *Lama glama*. In one embodiment, the VHH domain is in a chimeric antigen receptor. In one embodiment, the chimeric antigen receptor is on an immune cell. In one embodiment, the immune cell is selected from PBMC, a T cell, a NK cell or a macrophage. In one embodiment, the method is performed using FACS or MCS.

BRIEF DESCRIPTION OF THE DRAWINGS

FIG. 1 shows a schematic diagram and amino acid sequence of camel-derived nanobody VHH-His used in animal immunization.

FIG. 2 shows titer detection of fusion animal serum by ELISA.

FIG. 3 shows titer detection of supernatant of stable parent clone by ELISA.

FIG. 4 shows titer detection of supernatant of stable subclone by ELISA.

FIG. 5a and FIG. 5b show purity detection of 15 purified antibodies by PAGE.

FIG. 6a and FIG. 6b show EC50 affinity detection of the 15 antibodies and 10 different camel-derived nanobodies.

FIG. 7 shows amino acid sequence alignment of framework regions of camel-derived nanobodies.

FIG. 8 shows affinity detection of clone R166.C5.

FIG. 9 shows flow cytometry detection of CART cells.

FIG. 10 shows flow cytometry detection of CART cells before and after magnetic separation.

FIG. 12 shows FACS plots of five PE-labeled purified antibodies for flow cytometry separation detection of camel PBMC cells.

FIG. 13 shows SDS-PAGE profiles of antibody-coupled magnetic beads before and after the purification of camel serum heavy-chain antibodies.

DETAILED DESCRIPTION OF EMBODIMENTS

I. Definitions

Figure 6B:
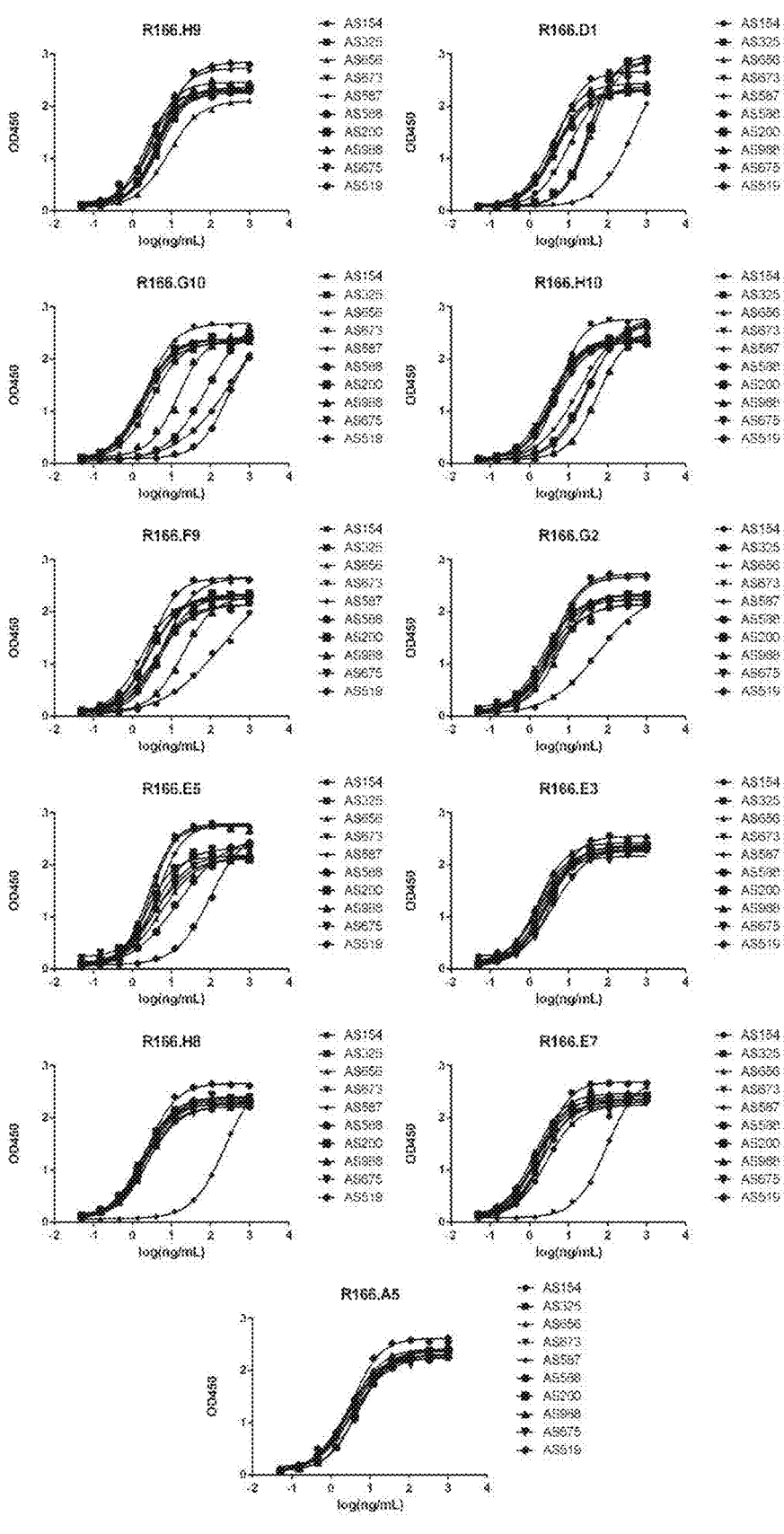
Figure 11:
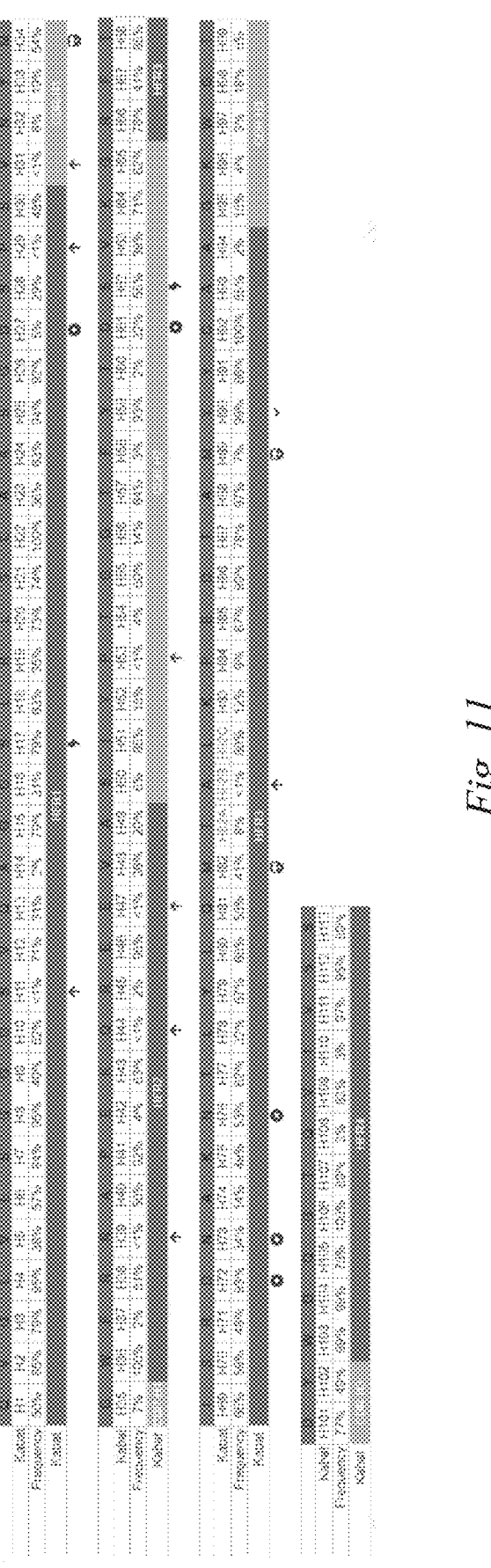
FIG. 11 shows Kabat numbering and residue frequency of camel-derived nanobodies used in animal immunization.

As used in the present description and appended claims, the singular forms "a," "an," and "the" include plural referents, unless the context clearly dictates otherwise. Therefore, for example, reference to "a molecule" optionally includes a combination of two or more of such molecules, and the like.

As used herein, the term "about" refers to a conventional error range of the corresponding numerical value easily known by those skilled in the art. Reference herein to "about" a certain value or a parameter includes (and describes) the embodiment involving the value or parameter itself.

It is understood that the aspects and embodiments of the present invention described herein include aspects and embodiments involving "comprise", "consist of", and "essentially consist of".

The terms "anti-VHH domain antibody", "antibody binding to a VHH domain" and "antibody specifically binding to a VHH domain" refer to an antibody capable of binding to a VHH domain with sufficient affinity. In one embodiment, as measured by, for example, radioimmunoassay (MA), the extent of binding of an anti-VHH domain antibody to an irrelevant, non-VHH domain protein is less than about 10% of that of the binding of the antibody to a VHH domain. In certain embodiments, an antibody binding to a VHH domain has a dissociation constant (Kd)≤1 μM, ≤100 nM, ≤10 nM, ≤1 nM, ≤0.1 nM, ≤0.01 nM or ≤0.001 nM (e.g., $10^{-8}$M or less, e.g., $10^{-8}$M to $10^{-13}$M, e.g., $10^{-9}$M to $10^{-13}$M). In certain embodiments, an anti-VHH domain antibody binds to a VHH domain epitope that is conserved in VHH domains from different species.

The term "heavy-chain antibody" or "HCAb" refers to a functional antibody that comprises a heavy chain but lacks a light chain commonly found in four-chain antibody. It is known that camelid animal (such as *Camelus dromedarius, Camelus bactrianus, Vicugna pacos* or *Lama glama*) can produce HCAb.

The term "single-domain antibody" or "sdAb" refers to a single antigen binding polypeptide with three complementarity determining regions (CDR). The sdAb alone can bind to an antigen without pairing with the corresponding CDR-containing polypeptide. In some cases, a single-domain antibody is engineered from camelid animal HCAb, and the heavy chain variable domain thereof is referred to herein as "VHH" (heavy chain variable domain of heavy-chain antibody). Camelid animal sdAb is the smallest known antigen-binding antibody fragment. Generally, VHH has the following structure from N-terminal to C-terminal: FR1-CDR1-FR2-CDR2-FR3-CDR3-FR4, wherein FR1 to FR4 respectively refer to framework regions 1 to 4, and CDR1 to CDR3 refer to complementarity determining regions 1 to 3.

For the purposes herein, "receptor human framework" refers to a framework of an amino acid sequence of a light chain variable domain (VL) framework or a heavy chain variable domain (VH) framework derived from a human immunoglobulin framework or a human consensus framework as defined below. The receptor human framework "derived" from a human immunoglobulin framework or a human consensus framework may contain the same amino acid sequence thereof or can contain an amino acid sequence change. In some embodiments, the number of amino acid changes is 10 or less, 9 or less, 8 or less, 7 or less, 6 or less, 5 or less, 4 or less, 3 or less, or 2 or less. In some embodiments, the VL receptor human framework is identical in terms of the sequence to the VL human immunoglobulin framework or human consensus framework.

"Affinity" refers to the strength of the sum of all non-covalent interactions between a single binding site of a molecule (e.g., antibody) and a binding partner thereof (e.g., antigen). Unless otherwise indicated, "binding affinity" as used herein refers to an intrinsic binding affinity that reflects 1:1 interaction between members of a binding pair (e.g., antibody and antigen). The affinity of molecule X for the partner thereof, Y, can generally be represented by the dissociation constant (Kd). Affinity can be measured by common methods known in the art, which comprise the methods described herein. Specific illustrative and exemplary embodiments for measuring binding affinity are described below.

An "affinity matured" antibody refers to an antibody with one or more alterations in one or more hypervariable regions (HVR), and such alterations result in an improvement of the affinity of the antibody for antigen compared to a parent antibody which does not possess such alterations.

The term "antibody" herein is used in the broadest sense and encompasses various antibody structures, including but not limited to a monoclonal antibody, a polyclonal antibody, a multispecific antibody (e.g., bispecific antibody), and an antibody fragment so long as it exhibits the desired antigen-binding activity.

An "antibody fragment" refers to a molecule that is different from an intact antibody, which comprises a part of the intact antibody and binds to the antigen to which the intact antibody binds. Examples of antibody fragments include but are not limited to Fv, Fab, Fab', Fab'-SH, and F(ab')2; diabody; linear antibody; single-chain antibody molecule (e.g., scFv); and multispecific antibody formed from antibody fragments. For example, the antigen-binding fragment can comprise the heavy chain variable domain and/or light chain variable domain of the antibody.

An "antibody binding to the same epitope" as the reference antibody refers to the antibody that blocks binding of the reference antibody to the antigen thereof by 50% or more in a competition assay, and on the contrary, the reference antibody blocks binding of the antibody to the antigen thereof by 50% or more in a competition assay. The exemplary competition assay is provided herein.

The term "chimeric antibody" refers to an antibody in which a part of the heavy and/or light chain is derived from a specific source or specie and the remaining part of the heavy and/or light chain is derived from a different source or specie.

A "class" of an antibody refers to the type of constant domains or constant regions possessed by the heavy chain thereof. There are 5 main classes of antibodies: IgA, IgD, IgE, IgG, and IgM, and several of these can be further divided into subclass (isotype), for example, IgG1, IgG2, IgG3, IgG4, IgA1, and IgA2. The heavy chain constant domains corresponding to different classes of immunoglobulins are referred to as $\alpha$, $\delta$, $\epsilon$, $\gamma$, and $\mu$, respectively.

"Framework region" or "FR" refers to variable domain residues other than hypervariable region (HVR) residues. Generally, FR of a variable domain consists of 4 FR domains: FR1, FR2, FR3, and FR4. Therefore, HVR and FR sequences generally appear in the following order in VH (or VL): FR1-H1(L1)-FR2-H2(L2)-FR3-H3(L3)-FR4.

The terms "full-length antibody", "intact antibody", and "whole antibody" can be used interchangeably herein and refer to an antibody that has a structure that is substantially similar to that of a natural antibody or has a heavy chain containing the Fc region as defined herein.

The terms "host cell," "host cell line," and "host cell culture" are used interchangeably and refer to the cells into which exogenous nucleic acid is introduced, including the progeny of such cells. The host cell includes a "transformant" and a "transformed cell", which includes a primary transformed cell and the progeny derived therefrom regardless of the number of passages. The progeny can be not completely identical to the parent cell in terms of nucleic acid content and can contain mutations. The mutant progeny that has the same function or biological activity screened or selected in the original transformed cell is included herein.

A "human antibody" refers to an antibody having an amino acid sequence corresponding to the amino acid sequence of an antibody produced by human or human cells or derived from a non-human source using human antibody repertoire or other human antibody coding sequences. This definition of a human antibody explicitly excludes a humanized antibody comprising non-human antigen-binding residues.

A "human consensus framework" refers to a framework representing the most frequently present amino acid residue in a sequence collection of a human immunoglobulin VL or VH framework. Generally, the sequence collection of a human immunoglobulin VL or VH is from a sequence subgroup of a variable domain. Generally, the sequence subgroup is the subgroup as described in Kabat et al., Sequences of Proteins of Immunological Interest, fifth Ed., NIH Publication 91-3242, Bethesda MD (1991), vol 1-3. In one embodiment, for VL, the subgroup is subgroup $\kappa I$ as described in Kabat et al., supra. In one embodiment, for VH, the subgroup is subgroup III as described in Kabat et al., supra.

A "humanized" antibody refers to a chimeric antibody comprising amino acid residues from a non-human HVR and amino acid residues from human FR. In certain embodiments, a humanized antibody can comprise at least one, usually two substantially entire variable domains, wherein all or substantially all HVRs (e.g., CDRs) correspond to those of a non-human antibody, and all or substantially all FRs correspond to those of a human antibody. Optionally, a humanized antibody can comprise at least a part of the constant region of an antibody derived from a human antibody. A "humanized form" of an antibody, e.g., a non-human antibody, refers to an antibody that has undergone humanization.

As used herein, the term "hypervariable region" or "HVR" refers to each region that is hypervariable in sequence (such as, "complementarity determining region" or "CDR") and/or forms a structurally defined loop (such as "hypervariable loop") and/or contains antigen-contacting residues ("antigen contacting") in an antibody variable domain. Generally, an antibody comprises 6 HVRs: H1, H2 and H3 (in VH); and L1, L2 and L3 (in VL). Exemplary HVRs herein include:

(a) hypervariable loop, which is present at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDR, which is present at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacting, which is present at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) a combination of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise stated, HVR residues and other residues (e.g., FR residues) in a variable domain are numbered according to Kabat et al., supra.

An "immunoconjugate" refers to an antibody conjugated to one or more heterologous molecules, including but not limited to a cytotoxic agent, for example, a conjugate comprising the antibody of the present invention.

An "isolated nucleic acid encoding an anti-VHH domain antibody" refers to one or more nucleic acid molecules encoding heavy and light chains (or fragments thereof) of an antibody, including such nucleic acid molecules in a single vector or different vectors, and such nucleic acid molecules present at one or more positions in host cells.

As used herein, the term "monoclonal antibody" refers to an antibody obtained from a population of substantially homogeneous antibodies, namely, each antibody constituting the population is same and/or binds to the same epitope, in addition to, for example, the antibody which contains naturally occurring mutations or is a possible variant occurring during the production of monoclonal antibody preparation, wherein such variants are generally present in extremely small amount. Each monoclonal antibody of the monoclonal antibody preparation is targeted for a single determinant on the antigen, which is different from the polyclonal antibody preparation which contains different antibodies for different determinants (epitopes). Therefore, the modifier "monoclonal" indicates the property of an antibody obtained from a group of substantially homogeneous antibodies and should not be interpreted as that any specific method is required for the production of antibodies. For example, multiple techniques can be used to produce the monoclonal antibody to be used in accordance with the present invention, and include, but not limited to hybridoma method, recombinant DNA method, phage display method, and the method of using transgenic animals containing all or part of human immunoglobulin loci. Such methods and other exemplary methods for producing monoclonal antibodies are described herein.

A "naked antibody" refers to an antibody that is not conjugated to a heterologous module (such as a cytotoxic module) or a radioactive label. The naked antibody can be present in a pharmaceutical formulation.

A "natural antibody" refers to naturally occurring immunoglobulin molecules with different structures. For example, a natural IgG antibody is a heterotetrameric glycoprotein of about 150,000 Daltons and composed of two identical light chains and two identical heavy chains bonded by a disulfide. Each heavy chain from N-terminal to C-terminal has a variable region (VH), also known as variable heavy domain or heavy chain variable domain, followed by three constant domains (CH1, CH2, and CH3). Similarly, each light chain from N-terminal to C-terminal has a variable region (VL), also known as variable light domain or light chain variable domain, followed by a constant light (CL) domain.

An antibody light chain can be classified into one of two types, known as kappa (κ) and lambda (λ) according to the constant domain amino acid sequence thereof.

The "percent (%) amino acid sequence identity" with respect to reference polypeptide sequence is defined as the percentage of amino acid residues in a candidate sequence that are identical to the amino acid residues in the reference polypeptide sequence, after aligning the sequences and introducing gaps, if necessary, to achieve the maximum percent sequence identity, and not considering any conservative substitutions as part of the sequence identity. Alignment for the purpose of determining percent amino acid sequence identity can be achieved in various ways within the technical scope of the art, for example, using publicly available computer software, such as BLAST, BLAST-2, ALIGN or Megalign (DNASTAR) software. Those skilled in the art can determine appropriate parameters for sequence alignment, including any algorithms required for obtaining maximal alignment over the full length of the sequences being compared. However, for the purpose of the present invention, the value of % amino acid sequence identity is generated using the sequence comparison computer program ALIGN-2. The ALIGN-2 sequence comparison computer program is written by Genentech, Inc., and the source code together with user documentation are submitted to the US Copyright Office (Washington D.C., 20559) and are registered under the US Copyright Registration No. TXU510087. The ALIGN-2 program is available to the public from Genentech, Inc. (South San Francisco, California), or can compile from the source code. The ALIGN2 program should be compiled to be used on UNIX operating systems, including digital UNIX V4.0D. All sequence comparison parameters are set by the ALIGN-2 program and remain unchanged.

In the case of using ALIGN-2 to compare amino acid sequences, the % amino acid sequence identity of a given amino acid sequence A to, with, or against a given amino acid sequence B (or which can be expressed as given amino acid sequence A which has or comprises a certain % amino acid sequence identity to, with, or against a given amino acid sequence B) is calculated as follows:

$$\text{score } X/Y \text{ multiplied by } 100$$

wherein X is the number of amino acid residues which are scored as identical matches by the sequence alignment program ALIGN-2 in the A and B alignment of the program and Y is the total number of amino acid residues in B. It should be appreciated that if the length of amino acid sequence A is not equal to the length of amino acid sequence B, the % amino acid sequence identity of A to B will not be equal to the % amino acid sequence identity of B to A. Unless explicitly stated otherwise, all values of % amino acid sequence identity used herein are obtained by using ALIGN-2 computer program as described in the previous paragraph.

The term "variable region" or "variable domain" refers to a domain in a heavy or light chain of an antibody that is involved in the binding of the antibody to an antigen. The heavy and light chain variable domains (VH and VL, respectively) of a natural antibody generally have similar structures, wherein each domain comprises 4 conserved framework regions (FR) and 3 hypervariable regions (HVR) (see, for example, Kindt et al., Kuby Immunology, 6th edition, W.H. Freeman and Co., pp. 91 (2007)). A single VH or VL domain can be sufficient to confer antigen-binding specificity. In addition, the VH or VL domain from an antigen-binding antibody can be respectively used to screen a library of complementary VL or VH domains to isolate the antibody that binds to a specific antigen. See, for example, Portolano et al., J. Immunol. 150:880-887 (1993); Clarkson et al., Nature 352:624-628 (1991).

As used herein, the term "vector" refers to a nucleic acid molecule capable of multiplying another nucleic acid to which it is linked. The term includes a vector that is a self-replicating nucleic acid structure and a vector incorporated into the genome of a host cell into which it is introduced. Certain vectors can direct the expression of a nucleic acid to which they are operably linked. Such vectors are referred to herein as "expression vector".

"Expression" generally refers to the process by which information (such as genetically encoded and/or epigenetic information) is transformed into a structure that exists and operates in a cell. Therefore, as used herein, "expression" can refer to transcription into a polynucleotide, translation into a polypeptide, or even polynucleotide and/or polypeptide modification (e.g., post-translational modification of a polypeptide). Fragments of the transcribed polynucleotide, the translated polypeptide, or polynucleotide and/or poly-
peptide modifications (e.g., post-translational modification
of a polypeptide) should also be regarded as being expressed
whether they are derived from a transcript generated by
alternative splicing or a degraded transcript, or from a
post-translational processing of the polypeptide (e.g., by
proteolysis). An "expressed gene" includes genes that are
transcribed into a polynucleotide (such as mRNA) and then
translated into a polypeptide, as well as genes that are
transcribed into RNA but not translated into a polypeptide
(e.g., transfer and ribosomal RNA).

II. Composition and Method of Using Same

The present invention provides a group of anti-VHH
domain antibodies or antigen-binding fragments thereof,
which specifically recognize the conformational epitopes of
camel-derived VHH domain framework regions. In the
present invention, it is found that the antibody has high
affinity, high specificity and high functionality. Moreover,
the present invention provides a method for preparing the
antibody and use thereof in the development of camel-
derived nanobodies and in the field of immune cell therapy.

In some embodiments, the antibody and method disclosed
in the present invention are used to detect the nanobody or
heavy-chain antibody derived from *Camelus dromedarius*.
In some other embodiments, the antibody and method dis-
closed in the present invention are used to detect the
nanobody or heavy-chain antibody derived from *Camelus
bactrianus*. In still other embodiments, the antibody and
method disclosed in the present invention are used to detect
the nanobody or heavy-chain antibody derived from *Vicugna
pacos*. In preferred embodiments, the antibody and method
disclosed in the present invention are used to detect the
nanobody or heavy-chain antibody derived from *Lama
glama*.

In one embodiment, the antibody and method disclosed in
the present invention are used for the separation of PBMC
cells specific for camel-derived heavy-chain antibodies, and
the antibody is also suitable for the separation of other types
of cells. In another embodiment, the antibody is used for
binding analysis of nanobodies. In one preferred embodi-
ment, the antibody is used for the affinity purification of
VHH antibodies by coupling to a solid-phase carrier
medium.

In one embodiment, the antibody disclosed in the present
invention is used for the flow cytometric identification of a
class of CART cells. In another embodiment, the antibody is
used for the flow cytometric sorting of CART cells. In one
preferred embodiment, the antibody is used for MACS
separation and purification of CART cells.

A. Exemplary Anti-VHH Domain Antibody

In one aspect, the present invention provides an anti-VHH
domain antibody or an antigen-binding fragment thereof.

In one embodiment, the antibody or the antigen-binding
fragment thereof of the present invention specifically binds
to a VHH domain. In one embodiment, the VHH domain is
a VHH domain of a camel-derived antibody. In one embodi-
ment, the camel-derived antibody is a single-domain anti-
body or a heavy-chain antibody derived from *Camelus
dromedarius, Camelus bactrianus, Vicugna pacos* or *Lama
glama*.

In one embodiment, the antibody or the antigen-binding
fragment thereof of the present invention binds to the VHH
domain at a framework region. In one embodiment, the
antibody or the antigen-binding fragment thereof of the
present invention binds to the VHH domain at a conformational epitope. In one embodiment, the antibody or the
antigen-binding fragment thereof of the present invention
binds to the VHH domain at a conformational epitope in a
framework region.

In one embodiment, the antibody or the antigen-binding
fragment thereof of the present invention specifically binds
to a VHH domain shown in any one of SEQ ID NOs: 241
and 246-255, or a VHH domain having at least 35%, at least
40%, at least 45%, at least 50%, at least 55%, at least 60%,
at least 65%, at least 70%, at least 75%, at least 80%, at least
85%, at least 90%, at least 95%, at least 96%, at least 97%,
at least 98% or at least 99% amino acid sequence identity to
any one of SEQ ID NOs: 241 and 246-255, or a consensus
sequence of SEQ ID NOs: 241 and 246-255. In one embodi-
ment, the antibody or the antigen-binding fragment thereof
of the present invention specifically binds to a framework
region of the VHH domain shown in any one of SEQ ID
NOs: 241 and 246-255, or a framework region having at
least 45%, at least 50%, at least 55%, at least 60%, at least
65%, at least 70%, at least 75%, at least 80%, at least 85%,
at least 90%, at least 95%, at least 96%, at least 97%, at least
98% or at least 99% amino acid sequence identity to the
framework region of the VHH domain shown in any one of
SEQ ID NOs: 241 and 246-255, or a consensus framework
sequence of SEQ ID NOs: 241 and 246-255.

In another aspect, the present invention provides an
anti-VHH domain antibody, which comprises at least one,
two, three, four, five or six HVRs selected from: (a) HVR-
H1 comprising the amino acid sequence of SEQ ID NO: 1,
2, 3, 4, 5, 6, 7, 8, 9, 10, 11, 12, 13, 14 or 15; (b) HVR-H2
comprising the amino acid sequence of SEQ ID NO: 16, 17,
18, 19, 20, 21, 22, 23, 24, 25, 26, 27, 28, 29 or 30; (c)
HVR-H3 comprising the amino acid sequence of SEQ ID
NO: 31, 32, 33, 34, 35, 36, 37, 38, 39, 40, 41, 42, 43, 44 or
45; (d) HVR-L1 comprising the amino acid sequence of
SEQ ID NO: 46, 47, 48, 49, 50, 51, 52, 53, 54, 55, 56, 57,
58, 59 or 60; (e) HVR-L2 comprising the amino acid
sequence of SEQ ID NO: 61, 62, 63, 64, 65, 66, 67, 68, 69,
70, 71, 72, 73, 74 or 75; and (f) HVR-L3 comprising the
amino acid sequence of SEQ ID NO: 76, 77, 78, 79, 80, 81,
82, 83, 84, 85, 86, 87, 88, 89 or 90.

In one aspect, the present invention provides an antibody,
which comprises at least one, at least two, or all three VH
HVR sequences selected from: (a) HVR-H1 comprising the
amino acid sequence of SEQ ID NO: 1, 2, 3, 4, 5, 6, 7, 8, 9,
10, 11, 12, 13, 14 or 15; (b) HVR-H2 comprising the amino
acid sequence of SEQ ID NO: 16, 17, 18, 19, 20, 21, 22, 23,
24, 25, 26, 27, 28, 29 or 30; and (c) HVR-H3 comprising the
amino acid sequence of SEQ ID NO: 31, 32, 33, 34, 35, 36,
37, 38, 39, 40, 41, 42, 43, 44 or 45.

In another aspect, the present invention provides an
antibody, which comprises at least one, at least two, or all
three VL HVR sequences selected from: (a) HVR-L1 com-
prising the amino acid sequence of SEQ ID NO: 46, 47, 48,
49, 50, 51, 52, 53, 54, 55, 56, 57, 58, 59 or 60; (b) HVR-L2
comprising the amino acid sequence of SEQ ID NO: 61, 62,
63, 64, 65, 66, 67, 68, 69, 70, 71, 72, 73, 74 or 75; and (c)
HVR-L3 comprising the amino acid sequence of SEQ ID
NO: 76, 77, 78, 79, 80, 81, 82, 83, 84, 85, 86, 87, 88, 89 or
90.

In another aspect, the antibody of the present invention
comprises (a) VH domain, which comprises at least one, at
least two, or all three VH HVR sequences selected from: (i)
HVR-H1 comprising the amino acid sequence of SEQ ID
NO: 1, 2, 3, 4, 5, 6, 7, 8, 9, 10, 11, 12, 13, 14 or 15; (ii)
HVR-H2 comprising the amino acid sequence of SEQ ID
NO: 16, 17, 18, 19, 20, 21, 22, 23, 24, 25, 26, 27, 28, 29 or 30; and (iii) HVR-H3 comprising the amino acid sequence of SEQ ID NO: 31, 32, 33, 34, 35, 36, 37, 38, 39, 40, 41, 42, 43, 44 or 45; and (b) VL domain, which comprises at least one, at least two, or all three VL HVR sequences selected from: (i) HVR-L1 comprising the amino acid sequence of SEQ ID NO: 46, 47, 48, 49, 50, 51, 52, 53, 54, 55, 56, 57, 58, 59 or 60; (ii) HVR-L2 comprising the amino acid sequence of SEQ ID NO: 61, 62, 63, 64, 65, 66, 67, 68, 69, 70, 71, 72, 73, 74 or 75; and (iii) HVR-L3 comprising the amino acid sequence of SEQ ID NO: 76, 77, 78, 79, 80, 81, 82, 83, 84, 85, 86, 87, 88, 89 or 90.

In another aspect, the anti-VHH domain antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 91, 92, 93, 94, 95, 96, 97, 98, 99, 100, 101, 102, 103, 104 or 105. In certain embodiments, the VH sequence having at least 90%, 91%, 92%, 93%, 94%, 95%, 96%, 97%, 98% or 99% identity contains substitutions (e.g., conservative substitutions), insertions or deletions relative to the reference sequence; however, the anti-VHH domain antibody containing the VH sequence retains the ability to bind to a VHH domain. In certain embodiments, 1 to 10 amino acids are substituted, inserted and/or deleted in SEQ ID NO: 91, 92, 93, 94, 95, 96, 97, 98, 99, 100, 101, 102, 103, 104 or 105. In certain embodiments, the substitutions, insertions or deletions occur in a region other than the HVR (i.e., in the FR). Optionally, the anti-VHH domain antibody comprises the VH sequence in SEQ ID NO: 91, 92, 93, 94, 95, 96, 97, 98, 99, 100, 101, 102, 103, 104 or 105, including the post-translational modification of the sequence.

In another aspect, provided is an anti-VHH domain antibody, wherein the antibody comprises a light chain variable domain (VL) having at least 90%, 91%, 92%, 93%, 94%, 95%, 96%, 97%, 98%, 99% or 100% sequence identity to the amino acid sequence of SEQ ID NO: 106, 107, 108, 109, 110, 111, 112, 113, 114, 115, 116, 117, 118, 119 or 120. In certain embodiments, the VL sequence having at least 90%, 91%, 92%, 93%, 94%, 95%, 96%, 97%, 98% or 99% identity contains substitutions (e.g., conservative substitutions), insertions, or deletions relative to the reference sequence; however, the anti-VHH domain antibody containing the VL sequence retains the ability to bind to a VHH domain. In certain embodiments, 1 to 10 amino acids are substituted, inserted and/or deleted in SEQ ID NO: 106, 107, 108, 109, 110, 111, 112, 113, 114, 115, 116, 117, 118, 119 or 120. In certain embodiments, the substitutions, insertions or deletions occur in a region other than the HVR (i.e., in the FR). Optionally, the anti-VHH domain antibody comprises the VL sequence in SEQ ID NO: 106, 107, 108, 109, 110, 111, 112, 113, 114, 115, 116, 117, 118, 119 or 120, including the post-translational modification of the sequence.

In another aspect, provided is an anti-VHH domain antibody, wherein the antibody comprises the VH in any of the embodiments provided above and the VL in any of the embodiments provided above.

In any one of the described embodiments, the anti-VHH domain antibody is humanized. In one embodiment, the anti-VHH domain antibody comprises the HVR of any of the described embodiments and further comprises a receptor human framework, such as a human immunoglobulin framework or a human consensus framework.

In yet another aspect, the present invention provides an antibody that binds to the same epitope as the anti-VHH domain antibody provided herein. For example, in certain embodiments, provided is an antibody that binds to the same epitope as the anti-VHH domain antibody.

In yet another aspect of the present invention, the anti-VHH domain antibody according to any of the described embodiments is a monoclonal antibody, including a chimeric antibody, a humanized antibody or a human antibody. In one embodiment, the anti-VHH domain antibody is an antibody fragment, for example, Fab, Fab', Fab'-SH, Fv, single chain variable fragment (scFv) and (Fab')$_2$ fragment. In another embodiment, the antibody is a full-length antibody, for example, an intact IgG antibody or an IgG1 isotype or other antibodies or isotypes.

In yet another aspect, the anti-VHH domain antibody according to any of the described embodiments may have any of the features described in sections 1-8 below, singly or in combination:

1. Antibody Affinity

In certain embodiments, the antibody provided herein has a dissociation constant (Kd) of $\leq 1$ μM, $\leq 100$ nM, $\leq 10$ nM, $\leq 1$ nM, $\leq 0.1$ nM, $\leq 0.01$ nM or $\leq 0.001$ nM (e.g., $10^{-8}$M or less, e.g., $10^{-8}$M to $10^{-12}$ M, e.g., $10^{-9}$M to $10^{-12}$ M, e.g., $10^{-10}$ M to $10^{-12}$ M, e.g., $10^{-11}$ M to $10^{-12}$ M).

In one embodiment, Kd is measured by radioimmunoassay (RIA). In one embodiment, RIA is performed with the antibody of interest in Fab format and the antigen thereof. For example, the binding affinity of the Fab to the antigen in a solution can be measured by equilibrating the Fab with minimum concentration of ($^{125}$I)-labeled antigens in the presence of a titration series of unlabeled antigens and then capturing the bound antigens with an anti-Fab antibody-coated plate (see, for example, Chen et al., J. Mol. Biol. 293:865-881(1999)). For establishing the conditions of the assay, the VHH domain ROTITER® multi-well plate (Thermo Scientific) was coated with 5 μg/ml of anti-Fab antibody (Cappel Labs) for capturing in 50 mM sodium carbonate (pH 9.6) overnight and then blocked with 2% (w/v) of bovine serum albumin in PBS at room temperature (about 23° C.) for 2-5 hours. In a non-adsorbed plate (Nunc #269620), 100 pM or 26 pM [125I]-antigen was mixed with serially diluted Fab of interest (for example, the assessment of the Fab is consistent with that of the anti-VEGF antibody Fab-12 in Presta et al., Cancer Res. 57: 4593-4599 (1997)). Then, the Fab of interest was incubated overnight; however, the incubation can continue for a longer period of time (e.g., about 65 hours) to ensure that equilibrium is reached. Thereafter, the mixture was transferred to a capture plate and incubated at room temperature (e.g., 1 hour). The solution was then removed, and the plate was washed 8 times with 0.1% of polysorbate 20 (TWEEN-20®) in PBS. After the plate was dried, 150 μl/well of scintillation fluid (VHH domain ROSCINT-20™; Packard) was added; and then the plate was counted on a TOPCOUNT™ gamma counter (Packard) for 10 minutes. The concentration of each Fab that gives less than or equal to 20% of the maximum binding was selected for the competitive binding assay.

According to another embodiment, Kd is measured using BIACORE® surface plasmon resonance assay. For example, the assay is performed with an immobilized antigen CMS chip and BIACORE®-2000 or BIACORE®-3000 (BIAcore, Inc., Piscataway, NJ) at about 10 response units (RU) at 25° C. In one embodiment, hydrochloric acid N-ethyl-N'-(3-dimethylaminopropyl)-carbodiimide (EDC) and N-hydroxysuccinimide (NETS) were used to activate carboxymethylated dextran biosensor chips according to the instructions from the supplier (CMS, BIACORE, Inc.). The antigen was diluted to 5 μg/ml (about 0.2 μM) with 10 mM sodium acetate pH 4.8 and then injected at a flow rate of 5 μl/min to obtain about 10 response units (RU) of coupled proteins. After the antigen was injected, 1 M ethanolamine was injected to block the unreacted group. For kinetic measurement, two-fold serial dilutions of Fab (0.78 nM to 500 nM) were injected in PBS (PBST) containing 0.05% polysorbate 20 (TWEEN-20™) surfactant at a flow rate of about 25 µl/min at 25° C. The association rate (kon) and dissociation rate (koff) were calculated using a simple one-to-one Langmuir binding model (BIACORE® Evaluation Software version 3.2) and simultaneously fitting the association and dissociation sensorgrams. The equilibrium dissociation constant (Kd) is calculated as the ratio koff/kon. See, for example, Chen et al., J. Mol. Biol. 293:865-881 (1999). If the binding rate exceeds 106 M-1 S-1 according to the above surface plasmon resonance assay, the binding rate can be measured using fluorescence quenching technology, that is, according to the measurement with a stirring cuvette in a spectrometer such as a spectrophotometer equipped with a shut-off device (Aviv Instruments) or SLM-AMINCO™ 8000 spectrophotometer (ThermoSpectronic) in the presence of an increasing concentration of antigens, the increase or decrease of fluorescence emission intensity (excitation=295 nm; emission=340 nm, 16 nm bandpass) of 20 nM of anti-antigen antibodies (Fab format) in PBS pH 7.2 was measured at 25° C.

2. Antibody Fragment

In certain embodiments, the antibody provided herein is an antibody fragment. The antibody fragment includes, but are not limited to, Fab, Fab', Fab'-SH, F(ab')2, Fv, and scFv fragment, and other fragments described below. For a review of certain antibody fragments, see Hudson et al., Nat. Med. 9:129-134 (2003). For a review of scFv fragments, see, for example, Pluckthün, in The Pharmacology of Monoclonal Antibodies, vol. 113, Rosenburg and Moore, ed., (Springer-Verlag, New York), pp. 269-315 (1994); also see WO 93/16185; and U.S. Pat. Nos. 5,571,894 and 5,587,458. For discussion of Fab and F(ab')2 fragments comprising salvage receptor binding epitope residues and having extended in vivo half-life, see U.S. Pat. No. 5,869,046.

A diabody is an antibody fragment with two antigen binding sites, which can be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). A tribody and a tetrabody are also disclosed in Hudson et al., Nat. Med. 9:129-134 (2003).

A single-domain antibody is an antibody fragment that comprises all or part of the heavy chain variable domain or all or part of the light chain variable domain of the antibody. In certain embodiments, the single-domain antibody is a human single-domain antibody (Domantis, Inc., Waltham, MA; see, for example, U.S. Pat. No. 6,248,516 B1).

An antibody fragment can be produced by various techniques, including but not limited to proteolytic digestion of an intact antibody and the production of recombinant host cells (e.g., E. coli. or phage), as described herein.

3. Chimeric Antibody and Humanized Antibody

In certain embodiments, the antibody provided herein is a chimeric antibody. Some chimeric antibodies are disclosed in e.g., U.S. Pat. No. 4,816,567; and Morrison et al., Proc. Natl. Acad. Sci. USA, 81:6851-6855 (1984). In one example, the chimeric antibody comprises a non-human variable region (for example, a variable region derived from a mouse, rat, hamster, rabbit or non-human primate, such as monkey) and a human constant region. In yet another example, the chimeric antibody is a "class-switched" antibody, wherein the class or subclass is changed from the class or subclass of the parent antibody. The chimeric antibody includes an antigen-binding fragment thereof.

In certain embodiments, the chimeric antibody is a humanized antibody. Typically, a non-human antibody is humanized to reduce immunogenicity to humans, while retaining the specificity and affinity of the parental non-human antibody. Generally, a humanized antibody comprises one or more variable domains, wherein HVR, e.g., CDR (or a portion thereof) is derived from a non-human antibody, and FR (or a portion thereof) is derived from a human antibody sequence. Optionally, a humanized antibody can also comprise at least a part of a human constant region. In some embodiments, some FR residues in the humanized antibody are substituted with corresponding residues from a non-human antibody (e.g., an antibody derived from HVR residues), for example, to restore or improve specificity or affinity of the antibody.

The humanized antibody and a production method therefor are reviewed in, e.g., Almagro and Fransson, Front. Biosci. 13:1619-1633 (2008), and further disclosed in, e.g., Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321 and 7,087,409; Kashmiri et al., Methods 36:25-34 (2005) (describing grafting of specificity determination regions (SDR)); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" method for FR shuffling).

The human framework region that can be used for humanization includes but are not limited to a framework region selected using the "best-fit" method (see, for example, Sims et al., J. Immunol. 151:2296 (1993)); a framework region derived from a consensus sequence of human antibodies of a particular subgroup of light or heavy chain variable regions (see, for example, Carter et al., Proc. Natl. Acad. Sci. USA, 89:4285 (1992); and Presta et al., J. Immunol., 151: 2623 (1993)); a human mature (somatically mutated) framework region or human germline framework region (see, for example, Almagro and Fransson, Front. Biosci. 13:1619-1633 (2008)); and a framework region derived by screening an FR library (see, for example, Baca et al., J. Biol. Chem. 272:10678-10684 (1997) and Rosok et al., J. Biol. Chem. 271:22611-22618 (1996)).

4. Human Antibody

In certain embodiments, the antibody provided herein is a human antibody. The human antibody can be produced using multiple techniques known in the art. Generally, the human antibody is disclosed in van Dijk and van de Winkel, Curr. Opin. Pharmacol. 5: 368-74 (2001) and Lonberg, Curr. Opin. Immunol. 20:450-459 (2008).

The human antibody can be prepared by administering an immunogen to a transgenic animal, wherein the transgenic animal was modified to produce an intact human antibody or an intact antibody with a human variable region in response to antigenic challenges. Such animals usually contain all or part of the human immunoglobulin loci, which replace the endogenous immunoglobulin loci, exists outside the chromosomes or is randomly integrated into the chromosomes of the animals. In such transgenic mice, the endogenous immunoglobulin loci are generally inactivated. With regard to a review of methods for obtaining the human antibody from transgenic animal, see Lonberg, Nat. Biotech. 23:1117-1125 (2005). Also see, for example, U.S. Pat. Nos. 6,075,181 and 6,150,584, which describes XENOMOUSE™ technique; U.S. Pat. No. 5,770,429, which describes HUMAB® technique; U.S. Pat. No. 7,041,870, which describes K-M MOUSE® technique, and U.S. Patent Application Publication Document No. US 2007/0061900, which describes VELOCIMOUSE® technique. The human variable region from the intact antibody produced by such animals can be further modified, for example, by combining with different human constant regions.

The human antibody can also be produced by a hybridoma-based method. Human myeloma and mouse-human heteromyeloma cell lines for the production of a human monoclonal antibody are described (see, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). The human antibody produced by human B-cell hybridoma technique is also disclosed in Li et al., Proc. Natl. Acad. Sci. USA, 103:3557-3562 (2006). Other methods include those disclosed in e.g., U.S. Pat. No. 7,189,826 (which describes the production of a monoclonal human IgM antibody from a hybridoma cell line) and Ni, Xiandai Mianyixue, 26(4):265-268 (2006) (which describes human-human hybridoma). Human hybridoma technique (Trioma technique) is also disclosed in Vollmers and Brandlein, Histology and Histopathology, 20(3):927-937 (2005) and Vollmers and Brandlein, Methods and Findings in Experimental and Clinical Pharmacology, 27(3):185-91 (2005).

The human antibody can also be produced by separating the Fv clone variable domain sequence selected from a human-derived phage display library. Then, such variable domain sequences can be combined with the desired human constant domain. The technique for selecting a human antibody from an antibody library is described below.

5. Library-Derived Antibody

The antibody of the present invention can be isolated by screening the combined library for the antibody having the one or more desired activities. For example, various methods for producing phage display libraries and screening such libraries for the antibody having the desired binding characteristics are known in the art. Such methods are reviewed in, for example, Hoogenboom et al., in Methods in Molecular Biology 178:1-37 (O'Brien et al., Human Press, Totowa, NJ, 2001), and further disclosed in, for example, McCafferty et al., Nature 348:552-554; Clackson et al., Nature 352: 624-628 (1991); Marks et al., J. Mol. Biol. 222: 581-597 (1992); Marks and Bradbury, Methods in Molecular Biology 248:161-175 (Lo ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In some phage display methods, the complete sets of VH and VL genes are respectively cloned by polymerase chain reaction (PCR) and randomly recombined in a phage library, and then the phage library can be screened for antigen-binding phages, as disclosed in Winter et al., Ann. Rev. Immunol., 12: 433-455 (1994). A phage usually displays an antibody fragment as a single-chain Fv (scFv) fragment or as a Fab fragment. The library from an immunized source provides a high-affinity antibody against an immunogen without constructing hybridomas. Alternatively, the natural repertoire can be cloned (for example from human) to provide a single source of antibodies against a large number of non-self-antigens and self-antigens without any immunity, as described by Griffiths et al., EMBO J, 12: 725-734 (1993). Finally, an unimmunized library can also be synthesized and produced by cloning the unrearranged V gene segments from a stem cell and using a PCR primer containing a random sequence to encode a highly variable CDR3 region and realize rearrangement in vitro, as described by Hoogenboom and Winter, J. Mol. Biol., 227: 381-388 (1992). Patent publication documents describing human antibody phage libraries include, for example: U.S. Pat. No. 5,750,373, and U.S. Patent publication document Nos. 2005/0079574, 2005/0119455, 2005/0266000, 2007/0117126, 2007/0160598, 2007/0237764, 2007/0292936 and 2009/0002360.

The antibody or the antibody fragment isolated from a human antibody library is considered to be the human antibody or human antibody fragment herein.

6. Multispecific Antibody

In certain embodiments, the antibody provided herein is a multispecific antibody, such as a bispecific antibody. A multispecific antibody is a monoclonal antibody that has binding specificities for at least two different sites. In certain embodiments, one of the binding specificities is for a VHH domain and the other specificity is for any other antigen. In certain embodiments, the bispecific antibody can bind to two different epitopes of the VHH domain. The bispecific antibody can also be used to localize the cytotoxic agent to the cell expressing VHH domain. The bispecific antibody can be prepared as a full-length antibody or an antibody fragment.

Techniques for generating a multispecific antibody include, but are not limited to, the recombinant co-expression of two immunoglobulin heavy chain-light chain pairs with different specificities (see Milstein and Cuello, Nature 305: 537 (1983), WO 93/08829, and Traunecker et al., EMBO J. 10: 3655 (1991), and "protuberance-into-cavity" engineering (see, for example, U.S. Pat. No. 5,731,168); the engineered electrostatic manipulation effect for producing an antibody Fc-heterodimeric molecule (WO 2009/089004 A1); cross-linking two or more antibodies or fragments (see, for example, U.S. Pat. No. 4,676,980, and Brennan et al., Science, 229: 81 (1985)); using a leucine zipper to produce a bispecific antibody (see, for example, Kostelny et al., J. Immunol., 148(5):1547-1553 (1992)); using the "diabody" technique for producing a bispecific antibody fragment (see, for example, Hollinger et al., Proc. Natl. Acad. Sci. USA, 90:6444-6448 (1993)); and using a single-chain Fv (sFv) dimer (see, for example, Gruber et al., J. Immunol., 152: 5368 (1994)); as well as preparing a trispecific antibody to produce a multispecific antibody as described in, for example, Tutt et al., J. Immunol. 147: 60 (1991).

Engineered modified antibodies with three or more functional antigen binding sites including "octopus antibody" are also included herein (see, e.g., US 2006/0025576 A1).

The antibody or fragment herein also includes a "dual acting FAb" or "DAF" comprising an antigen binding site that binds to a VHH domain and another different antigen (see, for example, US 2008/0069820).

7. Antibody Variant

In certain embodiments, the amino acid sequence variant of the antibody provided herein is encompassed. For example, it may be desirable to improve the binding affinity and/or other biological property of the antibody. The amino acid sequence variant of the antibody can be prepared by introducing appropriate modifications into the nucleotide sequence encoding the antibody or by peptide synthesis. Such modifications include, for example, deletion and/or insertion and/or substitution of residues within the amino acid sequence of the antibody. Any combination of deletion, insertion, and substitution can be made to obtain the final construct, as long as the final construct possesses the desired characteristics, e.g., antigen-binding.

In certain embodiments, the antibody variant with one or more amino acid substitutions are provided. Sites of interest for substitution mutagenesis include HVR and FR. Conservative substitutions are shown in Table 1 under the heading of "Preferred substitution". More substantial changes are provided in Table 1 under the heading of "Exemplary substitution" and as further described below in reference to amino acid side chain classes. Amino acid substitutions can be introduced into the antibody of interest, and the product is screened for the desired activity, for example, retained/improved antigen binding, reduced immunogenicity or improved ADCC or CDC.

TABLE 1

| Amino acid substitution | | |
| --- | --- | --- |
| Initial residue | Exemplary substitution | Preferred substitution |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Iie; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

According to common side chain properties, amino acids can be grouped as follows:

(1) hydrophobic: norleucine, Met, Ala, Val, Leu, Ile;

(2) neutral, hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions would require using a member of one of these classes to substitute a member of another class.

One class of substitution variants involve substituting one or more hypervariable region residues of a parent antibody (e.g., a humanized or human antibody). Generally, the resulting variant selected for further study will have changes (e.g., improvement) in certain biological properties (e.g., increased affinity and decreased immunogenicity) relative to the parent antibody and/or will substantially retain certain biological properties of the parent antibody. An exemplary substitutional variant is an affinity matured antibody, which can be conveniently produced by, for example, using phage display-based affinity maturation techniques such as those described herein. In short, one or more HVR residues are mutated, and the variant antibodies are displayed on phages and screened for a particular biological activity (such as binding affinity).

Alteration (e.g., substitution) can be made in HVR, e.g., to improve antibody affinity. Such alterations can be made in HVR "hotspot", i.e., residues encoded by codons that undergo mutation at high frequency during the somatic maturation process (see, e.g., Chowdhury, Methods Mol. Biol. 207:179-196 (2008)), and/or residues in contact with an antigen, wherein the resulting variant VH or VL is tested for binding affinity. Affinity maturation by the construction and reselection of a secondary library is disclosed in, for example, Hoogenboom et al., in Methods in Molecular Biology 178:1-37 (O'Brien et al. eds., Human Press, Totowa, NJ, (2001)). In some embodiments of affinity maturation, diversity is introduced into a variable gene selected for maturation by any of a variety of methods (e.g., error-prone PCR, strand shuffling or oligonucleotide-directed mutagenesis). Then, a secondary library is established. The library is then screened to identify any antibody variants with the desired affinity. Another method for introducing diversity involves an HVR-directed method, wherein several HVR residues (e.g., 4-6 residues for a time) are randomized. HVR residue involved in antigen binding can be specifically identified by for example, using alanine scanning mutagenesis or modeling. In particular, CDR-H3 and CDR-L3 are often targeted.

In certain embodiments, substitution, insertions or deletions can occur within one or more HVRs, as long as such changes do not substantially reduce the ability of an antibody to bind to an antigen. For example, a conservative change (e.g., a conservative substitution, as provided herein) can be made on HVRs, which does not substantially reduce binding affinity. For example, such changes can be made outside of antigen-contacting residues in an HVR. In certain embodiments of the variant VH and VL sequences provided above, each HVR is unaltered, or contains no more than one, two or three amino acid substitutions.

A method for identifying residues or regions that can be used as a target site for mutagenesis in an antibody is called "alanine scanning mutagenesis", as described by Cunningham and Wells (1989) Science, 244:1081-1085. In this method, a residue or a group of target residues (e.g., charged residues such as arg, asp, his, lys, and glu) are identified and substituted with neutral or negatively charged amino acids (for example, alanine or polyalanine) to determine whether the interaction between an antibody and an antigen is affected. Further substitution can be introduced at an amino acid position that indicates functional sensitivity to an initial substitution. Alternatively/additionally, the crystal structure of an antigen-antibody complex is used to identify a contact point between the antibody and the antigen. As a substitutional candidate, such contact residues and neighboring residues can be targeted or eliminated. The variants can be screened to determine whether they contain the desired property.

Amino acid sequence insertions include amino- and/or carboxyl-terminal fusions ranging in length from 1 residue to a polypeptide containing 100 or more residues, as well as intra-sequence insertions of single or multiple amino acid residues. Examples of terminal insertions include an antibody with an N-terminal methionyl residue. Other insertional variants of antibody molecules include a fusion of the N-terminal or C-terminal of an antibody with an enzyme (for example, for ADEPT) or a polypeptide extending the serum half-life of the antibody.

8. Antibody Derivative

In certain embodiments, the antibody provided herein can be further modified to contain additional non-proteinaceous modules known in the art and readily available. Modules suitable for antibody derivatization include, but are not limited to, a water-soluble polymer. Non-limiting examples of water-soluble polymers include, but are not limited to, polyethylene glycol (PEG), ethylene glycol/propylene glycol copolymers, carboxymethylcellulose, dextran, polyvinyl alcohol, polyvinyl pyrrolidone, poly-1,3-dioxolane, poly-1, 3,6-trioxane, ethylene/maleic anhydride copolymers, polyamino acid (homopolymers or random copolymers), and dextran or poly (n-vinyl pyrrolidone) polyethylene glycol, propropylene glycol homopolymers, propylene oxide/ethylene oxide co-polymers, polyoxyethylated polyol (e.g., glycerol), polyvinyl alcohol, and a mixture thereof. Polyethylene glycol propionaldehyde may have advantages in production due to its stability in water. The polymer can have any molecular weight and can be branched or unbranched. The number of polymers attached to an antibody can vary, and if more than one polymer is attached, they can be the same or different molecules. Generally, the number and/or type of polymers used for derivatization can be determined according to considerations including but not limited to the specific property or function to be improved of an antibody, whether an antibody derivative will be used for treatment under specified conditions, etc.

B. Recombination Method and Composition

A recombinant method and composition can be used to produce an antibody, for example, as described in U.S. Pat. No. 4,816,567. In one embodiment, provided is an isolated nucleic acid encoding the anti-VHH domain antibody described herein. Such nucleic acids can encode the amino acid sequence comprising the VL of the antibody and/or the amino acid sequence comprising the VH of the antibody (e.g., the light and/or heavy chain of the antibody). In yet another embodiment, provided are one or more vectors containing such nucleic acids (e.g., expression vectors). In yet another embodiment, provided is a host cell comprising such nucleic acids. In one such embodiment, the host cell comprises (e.g., is transformed with the following vector): (1) a vector comprising a nucleic acid, wherein the nucleic acid encodes an amino acid sequence comprising a VL of an antibody and an amino acid sequence comprising a VH of an antibody, or (2) a first vector and a second vector, wherein the first vector comprises a nucleic acid encoding an amino acid sequence comprising a VL of an antibody, and the second vector comprises a nucleic acid encoding an amino acid sequence comprising a VH of an antibody. In one embodiment, the host cell is a eukaryotic cell, such as Chinese hamster ovary (CHO) cells or lymphoid cells (e.g., Y0, NS0, Sp20 cells). In one embodiment, provided is a method for producing an anti-VHH domain antibody, wherein the method comprises culturing a host cell comprising a nucleic acid encoding an antibody as provided above in a culture medium under the condition suitable for antibody expression, and optionally, recovering the antibody from the host cell (or host cell culture medium).

For the recombinant production of an anti-VHH domain antibody, the nucleic acid encoding the antibody (for example, as described above) is isolated and inserted into one or more vectors for further cloning and/or expression in a host cell. Such nucleic acids can be easily separated and sequenced using conventional procedures (for example, by using an oligonucleotide probe that can specifically bind to genes encoding the heavy and light chains of the antibody).

Suitable host cells for the cloning or expression of antibody-encoding vectors include the prokaryotic or eukaryotic cells described herein. For example, an antibody can be produced in bacteria (such as E. coli.), in particular, when glycosylation and Fc effector function are not required. For expression of an antibody fragment and polypeptide in bacteria, see, for example, U.S. Pat. Nos. 5,648,237, 5,789, 199 and 5,840,523 (also see Charlton, Methods in Molecular Biology, vol. 248 (B.K.C. Lo ed., Humana Press, Totowa, NJ, 2003), pp. 245-254, which describes the expression of antibody fragment in E. coli.). After expression, the antibody can be separated from a bacterial cell mass in a soluble fraction and can be further purified.

In addition to prokaryote, eukaryotic microorganism such as filamentous fungi or yeast is a suitable cloning or expression host for the antibody-encoding vector and includes fungal and yeast strains, wherein the glycosylation pathway thereof is "humanized", resulting in the production of an antibody with a partially or fully human glycosylation pattern. See Gerngross, Nat. Biotech. 22:1409-1414 (2004), and Li et al., Nat. Biotech. 24:210-215 (2006).

The host cell suitable for expressing a glycosylated antibody is also derived from multicellular organisms (invertebrate and vertebrate). Examples of invertebrate cells include insect cells. Numerous baculoviral strains have been identified, which can be used in conjunction with insect cells, particularly for transfection of Spodoptera frugiperda cells.

A plant cell culture can also be used as a host. See, for example, U.S. Pat. Nos. 5,959,177, 6,040,498, 6,420,548, 7,125,978 and 6,417,429 (which describe PLANTIBODIES™ technique for producing an antibody in a transgenic plant).

A vertebrate cell can also be used as a host. For example, a mammalian cell line suitable for growth in a suspension can be useful. Other examples of useful mammalian host cell lines are SV40-transformed monkey kidney CV1 line (COS-7); human embryonic kidney lines (293 or 293 cells, as disclosed in e.g., Graham et al., J. Gen Virol. 36:59 (1977)); baby hamster kidney cells (BHK); mouse sertoli cells (TM4 cell, as disclosed in e.g., Mather, Biol. Reprod. 23:243-251 (1980)); monkey kidney cells (CV1); African green monkey kidney cells (VERO-76); human cervical cancer cells (HELA); canine kidney cells (MDCK); buffalo rat liver cells (BRL 3A); human lung cells (W138); human liver cells (Hep G2); mouse mammary tumor cells (MMT 060562); TRI cells, as disclosed in e.g., Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines, such as Y0, NS0 and Sp2/0. For a review of certain mammalian host cell lines suitable for antibody production, see, e.g., Yazaki and Wu, Methods in Molecular Biology, vol. 248 (B.K.C. Lo ed., Humana Press, Totowa, NJ), pp. 255-268 (2003).

C. Assay

The anti-VHH domain antibody provided herein can be identified, screened, or characterized for the physical/chemical property and/or biological activity thereof by various assays known in the art.

On one hand, the antigen binding activity of the antibody of the present invention is tested, for example, by a known method such as ELISA and Western blot.

On the other hand, a competition assay can be used to identify an antibody that competes with any of the anti-VHH domain antibody described herein for binding to the VHH domain. In certain embodiments, such competitive antibodies bind to the same epitope (e.g., linear or conformational epitope) as any of the anti-VHH domain antibodies described herein. For detailed exemplary methods for mapping an epitope to which an antibody binds, see Morris (1996) "Epitope Mapping Protocols", Methods in Molecular Biology vol. 66 (Humana Press, Totowa, NJ).

In one exemplary competition assay, an immobilized VHH domain was incubated in a solution comprising a first labeled antibody (which binds to a VHH domain, e.g., any of the anti-VHH domain antibodies described herein) and a second unlabeled antibody (which is tested the ability to compete with the first antibody for binding to the VHH domain). The second antibody can be present in the supernatant of hybridoma. As a control, an immobilized VHH domain was incubated in a solution comprising a first labeled antibody but not a second unlabeled antibody. After incubation under the condition that allows the first antibody to bind to the VHH domain, the excess unbound antibody was removed, and the amount of the label combined with the immobilized VHH domain was measured. If the amount of the label combined with the immobilized VHH domain is substantially reduced compared to the control sample, this indicates that the second antibody competes with the first antibody for binding to the VHH domain. See Harlow and Lane (1988) Antibodies: A Laboratory Manual ch.14 (Cold Spring Harbor Laboratory, Cold Spring Harbor, NY).

D. Method and Composition for Detection

In certain embodiments, any of the anti-VHH domain antibodies provided herein can be used to detect the presence of the VHH domain in a biological sample. As used herein, the term "detection" encompasses quantitative or qualitative detection.

In one embodiment, provided is an anti-VHH domain antibody for use in a detection method. In yet another aspect, provided is a method for detecting the presence of the VHH domain in a biological sample. In certain embodiments, the method comprises contacting a biological sample with an anti-VHH domain antibody under a condition that allows the anti-VHH domain antibody to bind to the VHH domain, as described herein, and detecting whether a complex is formed between the anti-VHH domain antibody and the VHH domain. Such methods can be in vitro or in vivo methods.

In certain embodiments, provided is a labeled anti-VHH domain antibody. Labels include, but are not limited to, a directly detectable label or module (such as fluorescent, luminescent, electron-dense, chemiluminescent, and radioactive label), and a module that is detected indirectly by for example enzyme reaction or molecular interaction, such as an enzyme or a ligand. Exemplary labels include but are not limited to radioisotopes $^{32}P$, $^{14}C$, $^{125}I$, $^{3}H$, and $^{131}I$, fluorophores such as rare-earth chelates or fluorescein and a derivative thereof, and rhodamine and a derivative thereof, dansyl, umbelliferone, luciferase, for example, firefly luciferase and bacterial luciferase (U.S. Pat. No. 4,737,456), luciferin, 2,3-dihydrophthalazinedione, horseradish peroxidase (HRP), alkaline phosphatase, (3-galactosidase, glucoamylase, lysozyme, sugar oxidase, for example, glucose oxidase, galactose oxidase, and glucose-6-phosphoric acid dehydrogenase, heterocycle oxidase such as uricase and xanthine oxidase (which is coupled with an enzyme that uses hydrogen peroxide to oxidize dye precursor, such as HRP), lactoperoxidase or microperoxidase, biotin/avidin, spin labels, phage labels, stable free radicals, etc.

Description of Sequences

| SEQ ID NO | Description | Sequence |
| --- | --- | --- |
| 1 | R166.C5 HCDR1 | NFAMS |
| 2 | R166.H9 HCDR1 | NYNMI |
| 3 | R166.F2 HCDR1 | SHDMS |
| 4 | R166.H8 HCDR1 | SFAMS |
| 5 | R166.E7 HCDR1 | SFAMS |
| 6 | R166.G8 HCDR1 | NIYWIC |
| 7 | R166.F9 HCDR1 | SNAMG |
| 8 | R166.G2 HCDR1 | SDAMS |
| 9 | R166.D1 HCDR1 | NYDMI |
| 10 | R166.G10 HCDR1 | SSAVS |
| 11 | R166.G3 HCDR1 | RYAMG |
| 12 | R166.E5 HCDR1 | GYYMI |
| 13 | R166.E3 HCDR1 | SCVLI |
| 14 | R166.A5 HCDR1 | NYTVI |
| 15 | R166.H10 HCDR1 | SYWMS |
| 16 | R166.C5 HCDR2 | IIYSGGTRDYATWAKG |
| 17 | R166.H9 HCDR2 | MIGDGDDAAWYASWAKG |
| 18 | R166.F2 HCDR2 | YIYYGSGSTDYASWAEG |
| 19 | R166.H8 HCDR2 | IIYATGGTRDYATWAAG |
| 20 | R166.E7 HCDR2 | IIYTGGTRDYATWAKG |
| 21 | R166.G8 HCDR2 | CINSGSNSYTYYANWVDG |
| 22 | R166.F9 HCDR2 | LINIYDNTYYASWAKG |

-continued

| SEQ ID NO | Description | Sequence |
|---|---|---|
| 23 | R166.G2 HCDR2 | LINRYGNTYYASWAKG |
| 24 | R166.D1 HCDR2 | VIYPTGTTYYANWVKG |
| 25 | R166.G10 HCDR2 | IIGSGGSTYYASWVNG |
| 26 | R166.G3 HCDR2 | IIGYGGNTNYANWAKG |
| 27 | R166.E5 HCDR2 | IVTSSGSTHYASWANG |
| 28 | R166.E3 HCDR2 | FIYGSGNAYYANWAKG |
| 29 | R166.A5 HCDR2 | IIFGSGGTYYATWAEG |
| 30 | R166.H10 HCDR2 | IISGSGSTYYATWAKG |
| 31 | R166.C5 HCDR3 | DRSPDYSAAFLL |
| 32 | R166.H9 HCDR3 | YLSFTRLDL |
| 33 | R166.F2 HCDR3 | GGYVGGGVDAFDP |
| 34 | R166.H8 HCDR3 | DRSPDYSAAFNL |
| 35 | R166.E7 HCDR3 | DRSPDYSAAFNL |
| 36 | R166.G8 HCDR3 | DRDAADTSDWSLNF |
| 37 | R166.F9 HCDR3 | YGTDSDFYYLDL |
| 38 | R166.G2 HCDR3 | YGTDSDFYFLDL |
| 39 | R166.D1 HCDR3 | KPILYVDSSGWYIDL |
| 40 | R166.G10 HCDR3 | YGGNSGGYDSFNL |
| 41 | R166.G3 HCDR3 | DNKSGGNNGYPYYGLDL |
| 42 | R166.E5 HCDR3 | EGGWAFDL |
| 43 | R166.E3 HCDR3 | SQEDDSFGYGFNL |
| 44 | R166.A5 HCDR3 | GYFGNTFWAMDP |
| 45 | R166.H10 HCDR3 | GNPHYSFGFNI |
| 46 | R166.C5 LCDR1 | QASESVYSNNHLA |
| 47 | R166.H9 LCDR1 | QSSQSVYHNNWLA |
| 48 | R166.F2 LCDR1 | QASQSIYTYLS |
| 49 | R166.H8 LCDR1 | QASESVYSNNHLA |
| 50 | R166.E7 LCDR1 | QASESVYSNNHLA |
| 51 | R166.G8 LCDR1 | QSSDSVNNDNWLA |
| 52 | R166.F9 LCDR1 | QASQNIYTYLS |
| 53 | R166.G2 LCDR1 | QASQSIYSYLS |
| 54 | R166.D1 LCDR1 | QASENINNYLS |
| 55 | R166.G10 LCDR1 | QASQSIYSHLS |
| 56 | R166.G3 LCDR1 | QASQSISSHLA |
| 57 | R166.E5 LCDR1 | QSSESVANSNWLS |
| 58 | R166.E3 LCDR1 | QASQSIGTYLS |
| 59 | R166.A5 LCDR1 | QASQSISTYLS |
| 60 | R166.H10 LCDR1 | QASESIYSWLS |

-continued

| SEQ ID NO | Description | Sequence |
|---|---|---|
| 61 | R166.C5 LCDR2 | SASTLES |
| 62 | R166.H9 LCDR2 | GAATLAS |
| 63 | R166.F2 LCDR2 | RASTLAS |
| 64 | R166.H8 LCDR2 | SASTLES |
| 65 | R166.E7 LCDR2 | SASTLES |
| 66 | R166.G8 LCDR2 | QASKLAS |
| 67 | R166.F9 LCDR2 | KASTLAS |
| 68 | R166.G2 LCDR2 | KASKLVS |
| 69 | R166.D1 LCDR2 | QASRLAS |
| 70 | R166.G10 LCDR2 | GASTLAS |
| 71 | R166.G3 LCDR2 | YASTLAS |
| 72 | R166.E5 LCDR2 | WASKLAS |
| 73 | R166.E3 LCDR2 | RASTLTS |
| 74 | R166.A5 LCDR2 | QASELAY |
| 75 | R166.H10 LCDR2 | SASYLAS |
| 76 | R166.C5 LCDR3 | AGYKSSDTDGTS |
| 77 | R166.H9 LCDR3 | AGVYNDDSENA |
| 78 | R166.F2 LCDR3 | QQGALSSNIHNT |
| 79 | R166.H8 LCDR3 | AGYKSSDTDGTS |
| 80 | R166.E7 LCDR3 | AGYKSSDTDGTS |
| 81 | R166.G8 LCDR3 | QGTGYSSTWYVA |
| 82 | R166.F9 LCDR3 | QSDWLISSNGNT |
| 83 | R166.G2 LCDR3 | QSDWLISSNGNT |
| 84 | R166.D1 LCDR3 | QQGHSVSNDVGNV |
| 85 | R166.G10 LCDR3 | QCTAGTSIYGNA |
| 86 | R166.G3 LCDR3 | HQSYSGSDVDNT |
| 87 | R166.E5 LCDR3 | QGGYTSDRRA |
| 88 | R166.E3 LCDR3 | QEGYSDINVNNI |
| 89 | R166.A5 LCDR3 | QQGYSDINVDNF |
| 90 | R166.H10 LCDR3 | QYNYDSGDGITNG |
| 91 | R166.C5 HCVR heavy chain variable region | QSVEESGGRLVTPGTPLTLTCTVSGFSLRNFAMSWVRQAPG KGLEWIGIIYSGGTRDYATWAKGRFTISKTSTTVDLKMTSPT TEDTATYFCARDRSPDYSAAFLLWGQGTLVTVSS |
| 92 | R166.H9 HCVR heavy chain variable region | QSLEESGGRLVTPGTPLTLTCTASGFSLNNYNMIWVRQAPGE GLEWIGMIGDGDDAAWYASWAKGRFTISKTSTTVDLEVTSL TTEDTAIYFCARYLSFTRLDLWGQGTLVTVSS |
| 93 | R166.F2 HCVR heavy chain variable region | QSVEESGGRLVTPGTPLTLTCTASGFTISSHDMSWVRQAPGK GLEWIGYIYYGSGSTDYASWAEGRFTITRNTNENTVTLKMT SLTTEDTATYFCARGGYVGGGVDAFDPWGPGTVVTVSS |
| 94 | R166.H8 HCVR heavy chain variable region | QSVEESGGRLVTPGTPLTLTCTVSGFSLSSFAMSWVRQAPGK GLEWIGIIYATGGTRDYATWAAGRFTISKTSTTVGLKMTSPT TEDTATYFCARDRSPDYSAAFNLWGQGTLVTVSS |

-continued

| SEQ ID NO | Description | Sequence |
|---|---|---|
| 95 | R166.E7 HCVR heavy chain variable region | QSVEESGGRLVTPGTPLTLTCTVSGFSLSSFAMSWVRQAPGK GLEWIGIIYTGGTRDYATWAKGRFTISKTSTTVDLKMTSPTT EDTATYFCARDRSPDYSAAFNLWGQGTLVTVSS |
| 96 | R166.G8 HCVR heavy chain variable region | QLLEQSGGGAEGGLVKPGGSLELCCKASGFSLSNIYWICWV RQAPGTGLEWIGCINSGSNSYTYYANWVDGRFTLSRDIDQST GCLQLNSLTAADTAMYYCARDRDAADTSDWSLNFWGQGT LVTVSS |
| 97 | R166.F9 HCVR heavy chain variable region | QSLEESGGRLVKPDETLTITCTVSGIDLSSNAMGWVRQAPGK GLEWIGLINIYDNTYYASWAKGRFTISKTSTTVDLKVTSLTT EDTATYFCARYGTDSDFYYLDLWGQGTLVTVSS |
| 98 | R166.G2 HCVR heavy chain variable region | QSLEESGGRLVKPDETLTITCTVSGIDLSSDAMSWVRQAPGK GLEWIGLINRYGNTYYASWAKGRFTISKTSTTVDLKVTSLTT EDTATYFCARYGTDSDFYFLDLWGQGTLVTVSS |
| 99 | R166.D1 HCVR heavy chain variable region | QSVEESGGRLVKPDESLTLTCTVSGFSLSNYDMIWVRQAPG KGLEWIGVIYPTGTTYYANWVKGRFTISKTSTTVGLLITSPTT EDTATYFCARKPILYVDSSGWYIDLWGQGTLVTVSS |
| 100 | R166.G10 HCVR heavy chain variable region | QSVEESGGRLVTPGTPLTLTCTVSGFSLSSSAVSWVRQAPGK GLEYIGIIGSGGSTYYASWVNGRFTISKTSTTVDLKMTSLTAA DTATYFCARYGGNSGGYDSFNLWGQGTLVTVSS |
| 101 | R166.G3 HCVR heavy chain variable region | QSVEESGGRLVTPGTPLTLTCTVSGIDLSRYAMGWVRQAPG KGLEYIGIIGYGGNTNYANWAKGRFTISKTSTTVDLKMTSP TTEDTATYFCARDNKSGGNNGYPYYGLDLWGPGTLVTVSS |
| 102 | R166.E5 HCVR heavy chain variable region | QSLEESGGRLVTPGTPLTLTCTASGFSLSGYYMIWVRQAPGK GLEYIGIVTSSGSTHYASWANGRFAISKTSSTTVDLKMPSLTT EDTATYFCAREGGWAFDLWGQGTLVTVSS |
| 103 | R166.E3 HCVR heavy chain variable region | QSLEESGGRLVTPGTPLTLTCTVSGIDLSSCVLIWVRQAPEKG LEWIGFIYGSGNAYYANWAKGRFTISKTSSTTVDLKITSPTTE DTATYFCARSQEDDSFGYGFNLWGQGTLVTVSS |
| 104 | R166.A5 HCVR heavy chain variable region | QSVEESGGRLVTPGTPLTLTCTVSGFSLNNYTVIWVRQAPGK GLEWIGIIFGSGGTYYATWAEGRFTISRTSTTVDLKMTSPTTE DTATYFCARGYFGNTFWAMDPWGPGTLVTVSS |
| 105 | R166.H10 HCVR heavy chain variable region | QSLEESGGRLVTPGTPLTLTCTASGFSLSSYWMSWVRQAPG KGLEYIGIISGSGSTYYATWAKGRFTISKTSSTTVDLKITSPTT EDTATYFCARGNPHYSFGFNIWGPGTLVTVSL |
| 106 | R166.C5 LCVR light chain variable region | IVMTQTPSSKSVPVGDTVTINCQASESVYSNNHLAWFQQKP GQPPKLLIYSASTLESGVPSRFKGSGSGTQFTLTISGVQCDDA ATYYCAGYKSSDTDGTSFGGGTEVVVK |
| 107 | R166.H9 LCVR light chain variable region | AVLTQTPSPVSAAVGGTVTINCQSSQSVYHNNWLAWYQQK PGQPPKLLIYGAATLASGVPSRFKGSGSGTQFTFTITDVQCDD VGTYYCAGVYNDDSENAFGGGTEVVVK |
| 108 | R166.F2 LCVR light chain variable region | AYDMTQTPASVEVAVGGTVTIKCQASQSIYTYLSWYQQKPG QPPKLLIYRASTLASGVSSRFKGSGSGTDFTLTISGAQCADAA TYYCQQGALSSNIHNTFGGGTEVVVK |
| 109 | R166.H8 LCVR light chain variable region | IVMTQTPSSKSVPVGDTVTINCQASESVYSNNHLAWFQQKP GQPPKLLIYSASTLESGVPSRFKGSGSGTQFTLTISGVQCDDA ATYYCAGYKSSDTDGTSFGGGTEVVVK |
| 110 | R166.E7 LCVR light chain variable region | IVMTQTPSSKSVPVGDTVTINCQASESVYSNNHLAWFQQKP GQPPKLLIYSASTLESGVPSRFKGSGSGTQFTLTISGVQCDDA ATYYCAGYKSSDTDGTSFGGGTEVVVK |
| 111 | R166.G8 LCVR light chain variable region | QVLTQTPSSVSAAVGGTVTISCQSSDSVNNDNWLAWYQQKP GQPPKLLIYQASKLASGVPSRFSGSGSGTQFTLTISGVQCDDA ANYYCQGTGYSSTWYVAFGGGTEVVVK |
| 112 | R166.F9 LCVR light chain variable region | ADIVMTQTPASVSEPVGGTVTIKCQASQNIYTYLSWYQQKP GQPPKLLIYKASTLASGVSSRFKGSGSGTEFTLTINDLECADA ATYYCQSDWLISSNGNTFGGGTEVVVTGDPVA |
| 113 | R166.G2 LCVR light chain variable region | ADIVMTQTPASVSEPVGGTVTIKCQASQSIYSYLSWYQQKPG QRPKLLIYKASKLVSGVPSRFGSGSGTEFTLTISDLECADAA SYYCQSDWLISSNGNTFGGGTEVVVT |

-continued

| SEQ ID NO | Description | Sequence |
|---|---|---|
| 114 | R166.D1 LCVR light chain variable region | AYDMTQTPSSVSAAVGGTVSIKCQASENINNYLSWYQQKPG QPPKLLIYQASRLASAVPSRFKGSGSGTQFTLTIDDLECADAA TYYCQQGHSVSNDVGNVFGGGTEVVVK |
| 115 | R166.G10 LCVR light chain variable region | DVVMTQTPASVSEPVGGTVTIKCQASQSIYSHLSWYQQKPG QPPKLLIHGASTLASGASSRFKASGSGTEFTLTISDLECADAA TYYCQCTAGTSIYGNAFGGGTEVVVR |
| 116 | R166.G3 LCVR light chain variable region | AYDMTQTPASVEVPVGGTVTINCQASQSISSHLAWYQQKRG QPPKVLIYYASTLASGVSSRFKGSGSGTEYTLTISGVECADA ATYFCHQSYSGSDVDNTFGGGTEVVVR |
| 117 | R166.E5 LCVR light chain variable region | QVLTQTPFSVSTAVGGTVTINCQSSESVANSNWLSWYQQKP GQPPKLLIYWASKLASGVPSRFSGSGSGTQFTLTISGVQCAD AATYYCQGGYTSDRRAFGGGTEVVVK |
| 118 | R166.E3 LCVR light chain variable region | AYDMTQTPASVEVAVGGTVTINCQASQSIGTYLSWYQQKPG QPPKLLIYRASTLTSGVSSRFKGSGSGTQFTLTISGVECADAA TYYCQEGYSDINVNNIFGGGTEVVVK |
| 119 | R166.A5 LCVR light chain variable region | ANIVMTQTPASVSGAVGGTVTIKCQASQSISTYLSWYQQKP GQPPKLLIYQASELAYGVSSRFKGSGSGTEFTLTISGVECADA ATYYCQQGYSDINVDNFFGGGTEVVVK |
| 120 | R166.H10 LCVR light chain variable region | ADIVMTQTPASVSEPVGGTVTINCQASESIYSWLSWYQQKPG QPPKLLIYSASYLASGVPSQFRGSGSGTEYTLTISDLECADAA TYYCQYNYDSGDGITNGFGGGTEVVVK |
| 121 | R166.C5 HCDR1 | AACTTTGCAATGAGC |
| 122 | R166.H9 HCDR1 | AACTACAACATGATC |
| 123 | R166.F2 HCDR1 | AGCCACGACATGAGT |
| 124 | R166.H8 HCDR1 | AGCTTTGCAATGAGC |
| 125 | R166.E7 HCDR1 | AGCTTTGCAATGAGC |
| 126 | R166.G8 HCDR1 | AATATCTACTGGATATGT |
| 127 | R166.F9 HCDR1 | AGCAATGCAATGGGC |
| 128 | R166.G2 HCDR1 | AGCGATGCGATGAGC |
| 129 | R166.D1 HCDR1 | AACTACGACATGATC |
| 130 | R166.G10 HCDR1 | AGCTCTGCAGTGAGC |
| 131 | R166.G3 HCDR1 | AGATATGCAATGGGC |
| 132 | R166.E5 HCDR1 | GGCTACTACATGATC |
| 133 | R166.E3 HCDR1 | AGCTGTGTGTTGATC |
| 134 | R166.A5 HCDR1 | AATTATACTGTCATC |
| 135 | R166.H10 HCDR1 | AGCTACTGGATGAGC |
| 136 | R166.C5 HCDR2 | ATCATTTATTCTGGTGGTACCAGGGACTACGCGACCTGGG CGAAAGGC |
| 137 | R166.H9 HCDR2 | ATGATTGGTGATGGTGATGATGCAGCATGGTACGCGAGCT GGGCGAAAGGC |
| 138 | R166.F2 HCDR2 | TACATTTATTATGGTAGTGGTAGCACGGACTACGCGAGCT GGGCGGAAGGC |
| 139 | R166.H8 HCDR2 | ATCATTTATGCTACTGGTGGTACCAGGGACTACGCGACCT GGGCGGCAGGC |
| 140 | R166.E7 HCDR2 | ATCATTTATACTGGTGGTACCAGGGACTACGCGACCTGGG CGAAAGGC |
| 141 | R166.G8 HCDR2 | TGCATTAATTCTGGTAGTAATTCTTATACTTACTACGCGAA CTGGGTGGATGGC |

-continued

| SEQ ID NO | Description | Sequence |
|---|---|---|
| 142 | R166.F9 HCDR2 | CTCATCAATATTTATGATAACACATACTACGCGAGCTGGG<br>CGAAAGGC |
| 143 | R166.G2 HCDR2 | CTCATCAATCGTTATGGTAACACATACTACGCGAGCTGGG<br>CGAAAGGC |
| 144 | R166.D1 HCDR2 | GTCATTTATCCTACTGGTACCACATACTACGCGAACTGGG<br>TGAAAGGC |
| 145 | R166.G10 HCDR2 | ATCATTGGTAGTGGTGGTAGCACATACTACGCGAGCTGGG<br>TGAATGGT |
| 146 | R166.G3 HCDR2 | ATCATTGGTTATGGTGGTAACACAAACTACGCGAACTGGG<br>CGAAAGGC |
| 147 | R166.E5 HCDR2 | ATCGTTACTAGTAGTGGTAGCACACACTACGCGAGCTGGG<br>CGAATGGT |
| 148 | R166.E3 HCDR2 | TTCATTTATGGTAGTGGTAACGCATACTACGCGAACTGGG<br>CGAAAGGC |
| 149 | R166.A5 HCDR2 | ATCATTTTTGGTAGTGGTGGCACATACTACGCGACCTGGG<br>CGGAAGGC |
| 150 | R1 66.H10 HCDR2 | ATCATTAGTGGCAGTGGTTCCACATACTACGCGACCTGGG<br>CGAAAGGC |
| 151 | R166.C5 HCDR3 | GATCGTAGTCCTGATTATAGTGCCGCCTTTCTCTTG |
| 152 | R166.H9 HCDR3 | TATCTTAGTTTCACTCGGTTGGATCTC |
| 153 | R166.F2 HCDR3 | GGTGGTTATGTTGGTGGTGGTGTTGATGCTTTTGATCCC |
| 154 | R166.H8 HCDR3 | GATCGTAGTCCTGATTATAGTGCCGCCTTTAACTTG |
| 155 | R166.E7 HCDR3 | GATCGTAGTCCTGATTATAGTGCCGCCTTTAACTTG |
| 156 | R166.G8 HCDR3 | GATCGGGATGCTGCTGATACTAGTGATTGGTCACTTAACT<br>TC |
| 157 | R166.F9 HCDR3 | TATGGTACTGATAGTGATTTTTATTATCTCGACTTG |
| 158 | R166.G2 HCDR3 | TATGGTACTGATAGTGATTTTTATTTTCTCGACTTG |
| 159 | R166.D1 HCDR3 | AAACCCATCTTATATGTTGATAGTAGTGGTTGGTATATCG<br>ACTTG |
| 160 | R166.G10 HCDR3 | TATGGTGGTAATAGTGGTGGTTATGATTCCTTTAACTTG |
| 161 | R166.G3 HCDR3 | GATAATAAAAGTGGTGGTAATAATGGTTACCCCTACTACG<br>GCTTGGACCTC |
| 162 | R166.E5 HCDR3 | GAGGGTGGTTGGGCTTTTGACTTG |
| 163 | R166.E3 HCDR3 | TCCCAAGAGGATGATAGTTTTGGTTATGGCTTTAACTTG |
| 164 | R166.A5 HCDR3 | GGTTATTTTGGTAATACTTTTTGGGCCATGGACCCC |
| 165 | R166.H10 HCDR3 | GGAAATCCTCATTATAGTTTTGGTTTTAATATC |
| 166 | R166.C5 LCDR1 | CAGGCCAGTGAGAGTGTTTATAGTAATAACCACTTAGCC |
| 167 | R166.H9 LCDR1 | CAGTCCAGTCAGAGTGTTTATCATAACAACTGGTTAGCC |
| 168 | R166.F2 LCDR1 | CAGGCCAGTCAGAGCATTTACACCTACTTATCC |
| 169 | R166.H8 LCDR1 | CAGGCCAGTGAGAGTGTTTATAGTAACAACCACTTAGCC |
| 170 | R166.E7 LCDR1 | CAGGCCAGTGAGAGTGTTTATAGTAACAACCACTTAGCC |
| 171 | R166.G8 LCDR1 | CAGTCCAGTGACAGCGTTAATAATGACAACTGGTTAGCC |
| 172 | R166.F9 LCDR1 | CAGGCCAGTCAGAACATTTACACCTACTTATCC |
| 173 | R166.G2 LCDR1 | CAGGCCAGTCAGAGCATTTACAGCTACTTATCC |

-continued

| SEQ ID NO | Description | Sequence |
| --- | --- | --- |
| 174 | R166.D1 LCDR1 | CAGGCCAGTGAGAACATTAACAACTACTTATCC |
| 175 | R166.G10 LCDR1 | CAGGCCAGTCAGAGCATTTACAGCCACTTGTCC |
| 176 | R166.G3 LCDR1 | CAGGCCAGTCAGAGCATCAGTAGCCACTTAGCC |
| 177 | R166.E5 LCDR1 | CAGTCCAGTGAGAGTGTTGCTAATAGCAATTGGTTATCC |
| 178 | R166.E3 LCDR1 | CAGGCCAGTCAGAGCATTGGTACCTACTTATCC |
| 179 | R166.A5 LCDR1 | CAGGCCAGTCAGAGCATTAGTACTTATTTATCC |
| 180 | R166.H10 LCDR1 | CAGGCCAGTGAAAGTATTTATAGTTGGTTATCC |
| 181 | R166.C5 LCDR2 | TCTGCATCCACTCTGGAATCT |
| 182 | R166.H9 LCDR2 | GGTGCGGCCACTCTGGCATCT |
| 183 | R166.F2 LCDR2 | AGGGCGTCCACTCTGGCATCT |
| 184 | R166.H8 LCDR2 | TCTGCGTCCACTCTGGAATCT |
| 185 | R166.E7 LCDR2 | TCTGCATCCACTCTGGAATCT |
| 186 | R166.G8 LCDR2 | CAGGCATCCAAACTGGCATCT |
| 187 | R166.F9 LCDR2 | AAGGCATCCACTCTGGCATCT |
| 188 | R166.G2 LCDR2 | AAGGCATCCAAACTGGTATCT |
| 189 | R166.D1 LCDR2 | CAGGCATCCAGACTGGCATCT |
| 190 | R166.G10 LCDR2 | GGTGCATCCACCCTGGCATCT |
| 191 | R166.G3 LCDR2 | TATGCGTCCACTCTGGCATCT |
| 192 | R166.E5 LCDR2 | TGGGCATCCAAATTGGCATCT |
| 193 | R166.E3 LCDR2 | AGGGCATCCACTCTGACATCT |
| 194 | R166.A5 LCDR2 | CAGGCATCCGAATTGGCATAT |
| 195 | R166.H10 LCDR2 | AGTGCATCCTATCTGGCATCT |
| 196 | R166.C5 LCDR3 | GCAGGATACAAAAGTAGCGATACTGATGGTACTTCT |
| 197 | R166.H9 LCDR3 | GCAGGCGTTTATAATGATGATAGTGAGAATGCT |
| 198 | R166.F2 LCDR3 | CAACAGGGTGCTCTTAGTAGCAATATTCATAACACT |
| 199 | R166.H8 LCDR3 | GCAGGATACAAAAGTAGCGATACTGATGGTACTTCT |
| 200 | R166.E7 LCDR3 | GCAGGATACAAAAGTAGCGATACTGATGGTACTTCT |
| 201 | R166.G8 LCDR3 | CAAGGCACTGGTTATAGTAGTACTTGGTACGTTGCT |
| 202 | R166.F9 LCDR3 | CAAAGCGATTGGCTTATTAGTAGTAATGGGAATACT |
| 203 | R166.G2 LCDR3 | CAAAGCGATTGGCTTATTAGTAGTAATGGGAATACT |
| 204 | R166.D1 LCDR3 | CAACAGGGCCATAGTGTTAGTAATGATGTTGGTAATGTT |
| 205 | R166.G10 LCDR3 | CAATGTACTGCTGGTACTAGTATTTATGGTAATGCT |
| 206 | R166.G3 LCDR3 | CACCAGTCTTATAGTGGTAGTGATGTTGATAATACT |
| 207 | R166.E5 LCDR3 | CAAGGCGGCTATACTAGTGATCGTCGTGCT |
| 208 | R166.E3 LCDR3 | CAAGAGGGTTATAGTGATATTAATGTTAATAATATT |
| 209 | R166.A5 LCDR3 | CAGCAGGGTTATAGTGATATTAATGTCGATAATTTT |
| 210 | R166.H10 LCDR3 | CAATACAATTATGATAGTGGTGATGGTATTACTAATGGT |

-continued

| SEQ ID NO | Description | Sequence |
|---|---|---|
| 211 | R166.C5 HCVR | CAGTCGGTGGAGGAGTCCGGGGGTCGCCTGGTCACGCCT<br>GGGACACCCCTGACACTCACCTGCACAGTCTCTGGATTCT<br>CCCTAAGGAACTTTGCAATGAGCTGGGTCCGCCAGGCTCC<br>AGGGAAGGGCCTGGAATGGATCGGAATCATTTATTCTGGT<br>GGTACCAGGGACTACGCGACCTGGGCGAAAGGCCGATTC<br>ACCATCTCCAAAACCTCGACCACGGTGGATCTGAAAATGA<br>CCAGTCCGACAACTGAGGACACGGCCACCTATTTCTGTGC<br>CAGAGATCGTAGTCCTGATTATAGTGCCGCCTTTCTCTTGT<br>GGGGCCAAGGCACCCTGGTCACCGTCTCCTCA |
| 212 | R166.H9 HCVR | CAGTCCCTGGAGGAGTCCGGGGGTCGCCTGGTCACGCCTG<br>GGACACCCCTGACACTCACCTGCACAGCCTCTGGATTCTC<br>CCTCAATAACTACAACATGATCTGGGTCCGCCAGGCTCCA<br>GGGGAGGGGCTGGAATGGATCGGAATGATTGGTGATGGT<br>GATGATGCAGCATGGTACGCGAGCTGGGCGAAAGGCCGA<br>TTCACCATCTCCAAAACCTCGACCACGGTGGATCTGGAAG<br>TGACCAGTCTGACAACCGAGGACACGGCCATTTATTTTTG<br>TGCCAGATATCTTAGTTTCACTCGGTTGGATCTCTGGGGC<br>CAGGGCACCCTGGTCACCGTCTCCTCA |
| 213 | R166.F2 HCVR | CAGTCGGTGGAGGAGTCCGGGGGTCGCCTGGTCACGCCT<br>GGGACACCCCTGACACTCACCTGCACAGCCTCTGGATTCA<br>CCATCAGTAGCCACGACATGAGTTGGGTCCGCCAGGCTCC<br>AGGGAAGGGGCTGGAATGGATCGGATACATTTATTATGG<br>TAGTGGTAGCACGGACTACGCGAGCTGGGCGGAAGGCCG<br>ATTCACCATCACCAGAAACACCAACGAGAACACGGTGAC<br>TCTGAAAATGACCAGTCTGACAACCGAGGACACGGCCAC<br>CTATTTCTGTGCCAGAGGTGGTTATGTTGGTGGTGGTGTT<br>GATGCTTTTGATCCCTGGGGCCCAGGCACCGTGGTCACCG<br>TCTCCTCA |
| 214 | R166.H8 HCVR | CAGTCGGTGGAGGAGTCCGGGGGTCGCCTGGTCACGCCT<br>GGGACACCCCTGACACTCACCTGCACAGTCTCTGGATTCT<br>CCCTAAGTAGCTTTGCAATGAGCTGGGTCCGCCAGGCTCC<br>AGGGAAGGGCCTGGAATGGATCGGAATCATTTATGCTACT<br>GGTGGTACCAGGGACTACGCGACCTGGGCGGCAGGCCGT<br>TTCACCATCTCCAAAACCTCGACCACGGTGGGTCTGAAAA<br>TGACCAGTCCGACAACTGAGGACACGGCCACCTATTTCTG<br>TGCCAGAGATCGTAGTCCTGATTATAGTGCCGCCTTTAAC<br>TTGTGGGGCCAAGGCACCCTGGTCACCGTCTCCTCA |
| 215 | R166.E7 HCVR | CAGTCGGTGGAGGAGTCCGGGGGTCGCCTGGTCACGCCT<br>GGGACACCCCTGACACTCACCTGCACAGTCTCTGGATTCT<br>CCCTAAGTAGCTTTGCAATGAGCTGGGTCCGCCAGGCTCC<br>AGGGAAGGGCCTGGAATGGATCGGAATCATTTATACTGG<br>TGGTACCAGGGACTACGCGACCTGGGCGAAAGGCCGATT<br>CACCATCTCCAAAACCTCGACCACGGTGGATCTGAAAATG<br>ACCAGTCCGACAACTGAGGACACGGCCACCTATTTCTGTG<br>CCAGAGATCGTAGTCCTGATTATAGTGCCGCCTTTAACTT<br>GTGGGGCCAAGGCACCCTGGTCACCGTCTCCTCA |
| 216 | R166.G8 HCVR | CAGCTGCTGGAGCAGTCCGGAGGAGGAGCCGAAGGAGGC<br>CTGGTCAAGCCTGGGGGATCCCTGGAACTCTGCTGCAAAG<br>CCTCTGGATTCTCCCTTAGTAATATCTACTGGATATGTTGG<br>GTCCGCCAGGCTCCAGGGACGGGGCTGGAGTGGATTGGA<br>TGCATTAATTCTGGTAGTAATTCTTATACTTACTACGCGAA<br>CTGGGTGGATGGCCGATTCACTCTCTCCAGAGACATCGAC<br>CAGAGCACAGGTTGCCTACAACTGAACAGTCTGACAGCC<br>GCGGACACGGCCATGTATTATTGTGCGAGAGATCGGGAT<br>GCTGCTGATACTAGTGATTGGTCACTTAACTTCTGGGGCC<br>AAGGCACCCTGGTCACCGTCTCCTCG |
| 217 | R166.F9 HCVR | CAGTCGCTGGAGGAGTCCGGGGGTCGCCTGGTCAAGCCT<br>GACGAGACCCTGACAATCACCTGCACAGTCTCTGGAATCG<br>ACCTCAGTAGCAATGCAATGGGCTGGGTCCGCCAGGCTCC<br>AGGGAAGGGGCTGGAGTGGATCGGACTCATCAATATTTA<br>TGATAACACATACTACGCGAGCTGGGCGAAAGGCCGATT<br>CACCATCTCCAAAACCTCGACCACGGTGGATTTGAAAGTG<br>ACCAGTCTGACAACCGAGGACACGGCCACCTATTTCTGTG<br>CCAGATATGGTACTGATAGTGATTTTTATTATCTCGACTTG<br>TGGGGCCAAGGCACCCTGGTCACCGTCTCCTCA |
| 218 | R166.G2 HCVR | CAGTCGCTGGAGGAGTCCGGGGGTCGCCTGGTCAAGCCT<br>GACGAAACCCTGACAATCACCTGCACAGTCTCTGGAATCG<br>ACCTCAGTAGCGATGCGATGAGCTGGGTCCGCCAGGCTCC<br>AGGGAAGGGGCTGGAATGGATCGGACTCATCAATCGTTA |

-continued

| SEQ ID NO | Description | Sequence |
|---|---|---|
| | | TGGTAACACATACTACGCGAGCTGGGCGAAAGGCCGATT |
| | | TACCATCTCCAAAACCTCGACCACGGTGGATTTGAAAGTG |
| | | ACCAGTCTGACAACCGAGGACACGGCCACCTATTTCTGTG |
| | | CCAGATATGGTACTGATAGTGATTTTTATTTTCTCGACTTG |
| | | TGGGGCCAAGGCACCCTGGTCACCGTCTCCTCA |
| 219 | R166.D1 HCVR | CAGTCGGTGGAGGAGTCCGGCGGTCGCCTGGTAAAGCCT |
| | | GACGAATCCCTGACACTCACCTGCACAGTCTCTGGATTCT |
| | | CCCTCAGCAACTACGACATGATCTGGGTCCGCCAGGCTCC |
| | | AGGGAAGGGGCTGGAATGGATCGGAGTCATTTATCCTACT |
| | | GGTACCACATACTACGCGAACTGGGTGAAAGGCCGATTC |
| | | ACCATCTCCAAAACCTCGACCACGGTGGGTCTGCTCATCA |
| | | CCAGTCCGACGACCGAGGACACGGCCACCTATTTCTGTGC |
| | | CAGAAAACCCATCTTATATGTTGATAGTAGTGGTTGGTAT |
| | | ATCGACTTGTGGGGCCAAGGCACCCTGGTCACCGTCTCCT |
| | | CA |
| 220 | R166.G10 HCVR | CAGTCGGTGGAGGAGTCCGGGGGTCGCCTAGTCACGCCT |
| | | GGGACACCCCTGACACTCACCTGCACAGTCTCTGGATTCT |
| | | CCCTCAGTAGCTCTGCAGTGAGCTGGGTCCGCCAGGCTCC |
| | | AGGGAAGGGGCTGGAATACATCGGAATCATTGGTAGTGG |
| | | TGGTAGCACATACTACGCGAGCTGGGTGAATGGTCGATTC |
| | | ACCATCTCCAAAACCTCGACCACGGTGGATCTGAAAATGA |
| | | CCAGTCTGACAGCCGCGGACACGGCCACCTATTTCTGTGC |
| | | CAGATATGGTGGTAATAGTGGTGGTTATGATTCCTTTAAC |
| | | TTGTGGGGCCAAGGCACCCTGGTCACCGTCTCCTCA |
| 221 | R166.G3 HCVR | CAGTCGGTGGAGGAGTCCGGGGGTCGCCTGGTCACGCCT |
| | | GGGACACCCCTGACACTCACCTGCACAGTCTCTGGAATCG |
| | | ACCTCAGTAGATATGCAATGGGCTGGGTCCGCCAGGCTCC |
| | | AGGGAAGGGGCTGGAATACATCGGAATCATTGGTTATGG |
| | | TGGTAACACAAACTACGCGAACTGGGCGAAAGGCCGATT |
| | | CACCATCTCCAAAACCTCGTCGACCACGGTGGATCTGAAA |
| | | ATGACCAGTCCGACAACCGAGGACACGGCCACCTATTTCT |
| | | GTGCCAGAGATAATAAAAGTGGTGGTAATAATGGTTACC |
| | | CCTACTACGGCTTGGACCTCTGGGGCCCAGGGACCCTCGT |
| | | CACCGTCTCTTCA |
| 222 | R166.E5 HCVR | CAGTCGCTGGAGGAGTCCGGGGGTCGCCTGGTCACGCCTG |
| | | GGACACCCCTGACACTCACCTGCACAGCCTCTGGATTCTC |
| | | CCTCAGTGGCTACTACATGATCTGGGTCCGCCAGGCTCCA |
| | | GGGAAGGGGCTGGAATACATCGGAATCGTTACTAGTAGT |
| | | GGTAGCACACACTACGCGAGCTGGGCGAATGGTCGATTC |
| | | GCCATCTCCAAAACCTCGTCGACCACGGTGGATCTGAAAA |
| | | TGCCCAGTCTGACAACCGAGGACACGGCCACCTATTTCTG |
| | | TGCCAGAGAGGGTGGTTGGGCTTTTGACTTGTGGGGCCAA |
| | | GGCACCCTGGTCACCGTCTCCTCA |
| 223 | R166.E3 HCVR | CAGTCGCTGGAGGAGTCCGGGGGTCGCCTGGTCACGCCTG |
| | | GGACACCCCTGACACTCACCTGCACAGTCTCTGGAATCGA |
| | | CCTCAGTAGCTGTGTGTTGATCTGGGTCCGCCAGGCTCCA |
| | | GAAAAGGGGCTGGAATGGATCGGATTCATTTATGGTAGT |
| | | GGTAACGCATACTACGCGAACTGGGCGAAAGGCCGATTC |
| | | ACCATCTCCAAAACCTCGTCGACCACGGTGGATCTGAAAA |
| | | TCACCAGTCCGACAACCGAGGACACGGCCACCTATTTCTG |
| | | TGCCAGATCCCAAGAGGATGATAGTTTTGGTTATGGCTTT |
| | | AACTTGTGGGGCCAAGGCACCCTGGTCACCGTCTCCTCA |
| 224 | R166.A5 HCVR | CAGTCGGTGGAGGAGTCCGGGGGTCGCCTGGTCACGCCT |
| | | GGGACACCCCTGACACTCACCTGCACAGTCTCTGGATTCT |
| | | CCCTCAATAATTATACTGTCATCTGGGTCCGCCAGGCTCC |
| | | AGGGAAGGGGCTGGAATGGATCGGAATCATTTTTGGTAG |
| | | TGGTGGCACATACTACGCGACCTGGGCGGAAGGCCGATT |
| | | CACCATCTCCAGAACCTCGACCACGGTGGATCTGAAAATG |
| | | ACCAGTCCGACAACCGAGGACACGGCCACCTATTTCTGTG |
| | | CCAGAGGTTATTTTGGTAATACTTTTTGGGCCATGGACCC |
| | | CTGGGGCCCAGGGACCCTCGTCACCGTCTCTTCA |

-continued

| SEQ ID NO | Description | Sequence |
|---|---|---|
| 225 | R166.H10 HCVR | CAGTCGCTGGAGGAGTCCGGGGGTCGCCTGGTCACGCCTG<br>GGACACCCCTGACACTCACCTGCACAGCCTCTGGATTCTC<br>CCTCAGTAGCTACTGGATGAGCTGGGTCCGCCAGGCTCCA<br>GGGAAGGGGCTGGAATATATCGGAATCATTAGTGGCAGT<br>GGTTCCACATACTACGCGACCTGGGCGAAAGGCCGATTCA<br>CCATCTCCAAAACCTCGTCGACCACGGTGGATCTGAAAAT<br>CACCAGTCCGACAACCGAGGACACGGCCACCTATTTCTGT<br>GCCAGAGGAAATCCTCATTATAGTTTTGGTTTTAATATCT<br>GGGGCCCAGGCACCCTGGTCACCGTCTCCTTG |
| 226 | R166.C5 LCVR | ATCGTGATGACCCAGACTCCATCTTCCAAGTCTGTCCCTG<br>TGGGAGACACAGTCACCATCAATTGCCAGGCCAGTGAGA<br>GTGTTTATAGTAATAACCACTTAGCCTGGTTTCAACAGAA<br>ACCAGGGCAGCCTCCCAAGCTCCTGATCTATTCTGCATCC<br>ACTCTGGAATCTGGGGTCCCATCGCGGTTCAAAGGCAGTG<br>GATCTGGGACACAGTTCACTCTCACCATCAGCGGCGTGCA<br>GTGTGACGATGCTGCCACTTACTACTGTGCAGGATACAAA<br>AGTAGCGATACTGATGGTACTTCTTTCGGCGGAGGGACCG<br>AGGTGGTGGTCAAA |
| 227 | R166.H9 LCVR | GCCGTGCTGACCCAGACTCCATCTCCCGTGTCTGCAGCTG<br>TGGGAGGCACAGTCACCATCAATTGCCAGTCCAGTCAGA<br>GTGTTTATCATAACAACTGGTTAGCCTGGTATCAGCAGAA<br>ACCAGGGCAGCCTCCCAAGCTCCTGATCTATGGTGCGGCC<br>ACTCTGGCATCTGGGGTCCCATCGCGGTTTAAAGGCAGTG<br>GATCTGGGACACAGTTCACTTTCACTATCACCGACGTGCA<br>GTGTGACGATGTTGGCACTTACTACTGTCAGGCGTTTAT<br>AATGATGATAGTGAGAATGCTTTCGGCGGAGGGACCGAG<br>GTGGTGGTCAAA |
| 228 | R166.F2 LCVR | GCCTATGATATGACCCAGACTCCAGCCTCTGTGGAGGTAG<br>CTGTGGGAGGCACAGTCACCATCAAGTG<br>CCAGGCCAGTCAGAGCATTTACACCTACTTATCCTGGTAT<br>CAGCAGAAACCAGGGCAGCCTCCCAAGCTCCTGATCTAC<br>AGGGCGTCCACTCTGGCATCTGGGGTCTCATCGCGGTTCA<br>AAGGCAGTGGATCTGGGACAGATTTCACTCTCACCATCAG<br>CGGCGCGCAGTGTGCCGATGCTGCCACTTACTATTGTCAA<br>CAGGGTGCTCTTAGTAGCAATATTCATAACACTTTCGGCG<br>GAGGGACCGAGGTGGTGGTCAAA |
| 229 | R166.H8 LCVR | ATCGTGATGACCCAGACTCCATCTTCCAAGTCTGTCCCTG<br>TGGGAGACACAGTCACCATCAATTGCCAGGCCAGTGAGA<br>GTGTTTATAGTAACAACCACTTAGCCTGGTTTCAACAGAA<br>ACCAGGGCAGCCTCCCAAGCTCCTGATCTATTCTGCGTCC<br>ACTCTGGAATCTGGGGTCCCATCGCGGTTCAAAGGCAGTG<br>GATCTGGGACACAGTTCACTCTCACCATCAGCGGCGTGCA<br>GTGTGACGATGCTGCCACTTACTACTGTCAGGATACAAA<br>AGTAGCGATACTGATGGTACTTCTTTCGGCGGAGGGACCG<br>AGGTGGTGGTCAAA |
| 230 | R166.E7 LCVR | ATCGTGATGACCCAGACTCCATCTTCCAAGTCTGTCCCTG<br>TGGGAGACACAGTCACCATCAATTGCCAGGCCAGTGAGA<br>GTGTTTATAGTAACAACCACTTAGCCTGGTTTCAACAGAA<br>ACCAGGGCAGCCTCCCAAGCTCCTGATCTATTCTGCATCC<br>ACTCTGGAATCTGGGGTCCCATCGCGGTTCAAAGGCAGTG<br>GATCTGGGACACAGTTCACTCTCACCATCAGCGGCGTGCA<br>GTGTGACGATGCTGCCACTTACTACTGTGCAGGATACAAA<br>AGTAGCGATACTGATGGTACTTCTTTCGGCGGAGGGACCG<br>AGGTGGTGGTCAAA |
| 231 | R166.G8 LCVR | CAAGTGCTGACCCAGACTCCATCCTCCGTGTCTGCAGCTG<br>TGGGAGGCACAGTCACCATCAGTTGCCAGTCCAGTGACA<br>GCGTTAATAATGACAACTGGTTAGCCTGGTATCAGCAGAA<br>ACCAGGGCAGCCTCCCAAGCTCCTGATCTACCAGGCATCC<br>AAACTGGCATCTGGGGTCCCATCCCGGTTCAGCGGCAGTG<br>GATCTGGGACACAGTTCACTCTCACCATCAGCGGCGTGCA<br>GTGTGACGATGCTGCCAATTACTACTGTCAAGGCACTGGT<br>TATAGTAGTACTTGGTACGTTGCTTTCGGCGGAGGGACCG<br>AGGTGGTGGTCAAA |
| 232 | R166.F9 LCVR | GCTGACATTGTGATGACCCAGACTCCAGCCTCCGTGTCTG<br>AACCTGTGGGAGGCACAGTCACCATCAAGTGCCAGGCCA<br>GTCAGAACATTTACACCTACTTATCCTGGTATCAGCAGAA<br>ACCAGGGCAGCCTCCCAAGCTCCTGATCTACAAGGCATCC<br>ACTCTGGCATCTGGGGTCTCATCGCGGTTCAAAGGCAGTG<br>GATCTGGGACAGAGTTCACTCTCACCATCAACGACCTGGA |

-continued

| SEQ ID NO | Description | Sequence |
|---|---|---|
| | | GTGTGCCGATGCTGCCACTTACTACTGTCAAAGCGATTGG<br>CTTATTAGTAGTAATGGGAATACTTTCGGCGGAGGGACCG<br>AGGTGGTGGTCACAGGTGATCCAGTTGCA |
| 233 | R166.G2 LCVR | GCTGACATTGTGATGACCCAGACTCCAGCCTCCGTGTCTG<br>AACCTGTGGGAGGCACAGTCACCATCAAGTGCCAGGCCA<br>GTCAGAGCATTTACAGCTACTTATCCTGGTATCAGCAGAA<br>ACCAGGGCAGCGTCCCAAACTCCTGATCTACAAGGCATCC<br>AAACTGGTATCTGGGGTCCCATCGCGGTTCAGAGGCAGTG<br>GATCTGGGACAGAGTTCACTCTCACCATCAGCGACCTGGA<br>GTGTGCCGATGCTGCCTCTTACTACTGTCAAAGCGATTGG<br>CTTATTAGTAGTAATGGGAATACTTTCGGCGGAGGGACCG<br>AGGTGGTGGTCACA |
| 234 | R166.D1 LCVR | GCCTATGATATGACCCAGACTCCATCCTCCGTGTCTGCAG<br>CTGTGGGAGGCACAGTCAGCATCAAGTGCCAGGCCAGTG<br>AGAACATTAACAACTACTTATCCTGGTATCAGCAGAAACC<br>AGGGCAGCCTCCCAAGCTCCTGATCTACCAGGCATCCAGA<br>CTGGCATCTGCGGTCCCATCGCGGTTCAAAGGCAGTGGAT<br>CTGGGACACAGTTCACTCTCACCATCGACGACCTGGAGTG<br>TGCCGATGCTGCCACTTACTACTGTCAACAGGGCCATAGT<br>GTTAGTAATGATGTTGGTAATGTTTTCGGCGGAGGGACCG<br>AGGTGGTGGTCAAA |
| 235 | R166.G10 LCVR | GATGTTGTGATGACCCAGACTCCAGCCTCCGTGTCTGAAC<br>CTGTGGGAGGCACAGTCACCATCAAGTGCCAGGCCAGTC<br>AGAGCATTTACAGCCACTTGTCCTGGTATCAGCAGAAACC<br>AGGGCAGCCTCCCAAGCTCCTGATCCATGGTGCATCCACC<br>CTGGCATCTGGGGCCTCATCGCGGTTTAAAGCCAGTGGAT<br>CTGGGACAGAGTTCACTCTCACCATCAGCGACCTGGAGTG<br>TGCCGATGCTGCCACTTACTACTGTCAATGTACTGCTGGT<br>ACTAGTATTTATGGTAATGCTTTCGGCGGAGGGACCGAGG<br>TGGTGGTCAGA |
| 236 | R166.G3 LCVR | GCCTATGATATGACCCAGACTCCAGCCTCTGTGGAGGTAC<br>CTGTGGGAGGCACAGTCACCATCAATTGCCAGGCCAGTCA<br>GAGCATCAGTAGCCACTTAGCCTGGTATCAGCAGAAACG<br>AGGGCAGCCTCCCAAGGTCCTGATCTATTATGCGTCCACT<br>CTGGCATCTGGGGTCTCATCGCGGTTCAAAGGCAGTGGAT<br>CTGGGACAGAGTACACTCTCACCATTAGCGGCGTGGAGTG<br>TGCCGATGCTGCCACTTACTTTTGTCACCAGTCTTATAGTG<br>GTAGTGATGTTGATAATACTTTCGGCGGAGGGACCGAGGT<br>GGTGGTCAGA |
| 237 | R166.E5 LCVR | CAAGTGCTGACCCAGACTCCATTCTCCGTGTCTACAGCTG<br>TGGGAGGCACAGTCACCATCAATTGCCAGTCCAGTGAGA<br>GTGTTGCTAATAGCAATTGGTTATCCTGGTATCAGCAGAA<br>ACCAGGACAGCCTCCCAAGCTCCTGATCTACTGGGCATCC<br>AAATTGGCATCTGGGGTCCCATCGCGGTTCAGTGGCAGTG<br>GATCTGGGACACAGTTCACTCTCACCATCAGCGGCGTGCA<br>GTGTGCCGATGCTGCCACTTACTACTGTCAAGGCGGCTAT<br>ACTAGTGATCGTCGTGCTTTCGGCGGAGGGACCGAGGTGG<br>TGGTCAAA |
| 238 | R166.E3 LCVR | GCCTATGATATGACCCAGACTCCAGCCTCTGTGGAGGTAG<br>CTGTGGGAGGCACAGTCACCATCAATTGCCAGGCCAGTCA<br>GAGCATTGGTACCTACTTATCCTGGTATCAACAGAAACCA<br>GGGCAGCCTCCCAAGCTCCTGATCTACAGGGCATCCACTC<br>TGACATCTGGGGTCTCATCGCGGTTCAAAGGCAGTGGATC<br>TGGGACACAGTTCACTCTCACCATCAGCGGCGTGGAGTGT<br>GCCGATGCTGCCACTTACTACTGTCAAGAGGGTTATAGTG<br>ATATTAATGTTAATAATATTTTCGGCGGAGGGACCGAGGT<br>GGTGGTCAAA |
| 239 | R166.A5 LCVR | GCCAACATCGTGATGACCCAGACTCCAGCCTCCGTGTCTG<br>GAGCTGTGGGAGGCACAGTCACCATCAAGTGCCAGGCCA<br>GTCAGAGCATTAGTACTTATTTATCCTGGTATCAGCAGAA<br>ACCAGGGCAGCCTCCCAAACTCCTGATTTACCAGGCATCC<br>GAATTGGCATATGGGGTCTCATCGCGGTTCAAAGGCAGTG<br>GATCTGGGACAGAGTTCACTCTCACCATCAGCGGCGTGGA<br>GTGTGCCGATGCTGCCACTTACTATTGTCAGCAGGGTTAT<br>AGTGATATTAATGTCGATAATTTTTTCGGCGGAGGGACCG<br>AGGTGGTGGTCAAA |
| 240 | R166.H10 LCVR | GCTGACATTGTGATGACCCAGACTCCAGCCTCCGTGTCTG<br>AACCTGTGGGAGGCACAGTCACCATCAATTGCCAGGCCA |

-continued

| SEQ ID NO | Description | Sequence |
|---|---|---|
| | | GTGAAAGTATTTATAGTTGGTTATCCTGGTATCAACAGAA |
| | | ACCAGGGCAGCCTCCCAAGCTCCTGATCTATAGTGCATCC |
| | | TATCTGGCATCTGGCGTCCCATCACAATTCAGAGGCAGTG |
| | | GATCTGGGACAGAGTACACTCTCACCATCAGCGACCTGGA |
| | | GTGTGCCGATGCTGCCACTTATTACTGTCAATACAATTAT |
| | | GATAGTGGTGATGGTATTACTAATGGTTTCGGCGGAGGGA |
| | | CCGAGGTGGTGGTCAAA |
| 241 | AS718 VHH | QVQLVESGGGSVQAGGSLRLSCAASGDSPSVNYMGWFRRA |
| | | PEKQREEVASIYPTGGTFYTDSVKGRFTISRDNAKNTLYLQM |
| | | TALKPEDTAMYYCAAGKWGTDYWGQGTQVIVSS |
| 242 | Heavy chain constant region | GQPKAPSVFPLAPCCGDTPSSTVTLGCLVKGYLPEPVTVTWN |
| | | SGTLTNGVRTFPSVRQSSGLYSLSSVVSVTSSSQPVTCNVAH |
| | | PATNTKVDKTVAPSTCSKPTCPPPELLGGPSVFIFPPKPKDTL |
| | | MISRTPEVTCVVVDVSQDDPEVQFTWYINNEQVRTARPPLR |
| | | EQQFNSTIRVVSTLPIAHQDWLRGKEFKCKVHNKALPAPIEK |
| | | TISKARGQPLEPKVYTMGPPREELSSRSVSLTCMINGFYPSDI |
| | | SVEWEKNGKAEDNYKTTPAVLDSDGSYFLYSKLSVPTSEWQ |
| | | RGDVFTCSVMHEALHNHYTQKSISRSPGK |
| 243 | Heavy chain constant region | GGGCAACCTAAGGCTCCATCAGTCTTCCCACTGGCCCCCT |
| | | GCTGCGGGGACACACCCAGCTCCACGGTGACCCTGGGCT |
| | | GCCTGGTCAAAGGCTACCTCCCGGAGCCAGTGACCGTGAC |
| | | CTGGAACTCGGGCACCCTCACCAATGGGGTACGCACCTTC |
| | | CCGTCCGTCCGGCAGTCCTCAGGCCTCTACTCGCTGAGCA |
| | | GCGTGGTGAGCGTGACCTCAAGCAGCCAGCCCGTCACCTG |
| | | CAACGTGGCCCACCCAGCCACCAACACCAAAGTGGACAA |
| | | GACCGTTGCGCCCTCGACATGCAGCAAGCCCACGTGCCCA |
| | | CCCCCTGAACTCCTGGGGGGACCGTCTGTCTTCATCTTCCC |
| | | CCCAAAACCCAAGGACACCCTCATGATCTCACGCACCCCC |
| | | GAGGTCACATGCGTGGTGGTGGACGTGAGCCAGGATGAC |
| | | CCCGAGGTGCAGTTCACATGGTACATAAACAACGAGCAG |
| | | GTGCGCACCGCCCGGCCGCCGCTACGGGAGCAGCAGTTC |
| | | AACAGCACGATCCGCGTGGTCAGCACCCTCCCCATCGCGC |
| | | ACCAGGACTGGCTGAGGGGCAAGGAGTTCAAGTGCAAAG |
| | | TCCACAACAAGGCACTCCCGGCCCCCATCGAGAAAACCA |
| | | TCTCCAAAGCCAGAGGGCAGCCCCTGGAGCCGAAGGTCT |
| | | ACACCATGGGCCCTCCCCGGGAGGAGCTGAGCAGCAGGT |
| | | CGGTCAGCCTGACCTGCATGATCAACGGCTTCTACCCTTC |
| | | CGACATCTCGGTGGAGTGGGAGAAGAACGGGAAGGCAGA |
| | | GGACAACTACAAGACCACGCCGGCCGTGCTGGACAGCGA |
| | | CGGCTCCTACTTCCTCTACAGCAAGCTCTCAGTGCCCACG |
| | | AGTGAGTGGCAGCGGGGCGACGTCTTCACCTGCTCCGTGA |
| | | TGCACGAGGCCTTGCACAACCACTACACGCAGAAGTCCAT |
| | | CTCCCGCTCTCCGGGTAAA |
| 244 | Light chain constant region | GDPVAPTVLIFPPAADQVATGTVTIVCVANKYFPDVTVTWE |
| | | VDGTTQTTGIENSKTPQNSADCTYNLSSTLTLTSTQYNSHKE |
| | | YTCKVTQGTTSVVQSFNRGDC |
| 245 | Light chain constant region | GGTGATCCAGTTGCACCTACTGTCCTCATCTTCCCACCAG |
| | | CTGCTGATCAGGTGGCAACTGGAACAGTCACCATCGTGTG |
| | | TGTGGCGAATAAATACTTTCCCGATGTCACCGTCACCTGG |
| | | GAGGTGGATGGCACCACCCAAACAACTGGCATCGAGAAC |
| | | AGTAAAACACCGCAGAATTCTGCAGATTGTACCTACAACC |
| | | TCAGCAGCACTCTGACACTGACCAGCACACAGTACAACA |
| | | GCCACAAAGAGTACACCTGCAAGGTGACCCAGGGCACGA |
| | | CCTCAGTCGTCCAGAGCTTCAATAGGGGTGACTGT |
| 246 | AS154 VHH | QVQLVESGGGLVQPGGSLRLSCAASGGTLDYYAIGWFRQAP |
| | | GKEREAVSCISSSDGSTYYADSVKGRFTISRDNSKNTLYLQM |
| | | NSLRAEDTAVYHCATDRACGSSWLGAESWAQGTLVTVSS |
| 247 | AS325 VHH | AVQLVESGGGLVQAGGSLRLSCIASGIEFTIGVMGWYRQVP |
| | | GKEREFVAAITNGGRPNYADSVKGRFAISRDNAKNTVYLLM |
| | | NSLKPEDTAVYYCALDRLFKSPDGLVDYWGQGTQVTVSL |
| 248 | AS656 VHH | EVQLVESGGGLVQVGDSLRLSCAASGRSFENYAIGWFRQAP |
| | | GKEREFVATISWIPRTAYSTTYYADSVKGRFTISGDNSKNTV |
| | | YLQMTSLKPEDTAVYYCAAGGATGPLALDSHYGYWGQGT |
| | | QVTVSS |

-continued

| SEQ ID NO | Description | Sequence |
|---|---|---|
| 249 | AS673 VHH | QVQLVESGGGLVQAGGSLRLSCAASGRTFITYAIGWFRQAP<br>GKEREFVSAINWSGSMTSYADSVKGRFTISRDNAKNTVYLQ<br>MNGLKPEDTAVYYCAAHRGAIAPIAQSVYTNWGQGTQVTV<br>SS |
| 250 | AS587 VHH | QVQLVESGGGLVQPGGSLTLSCAASGFTFSTAAMSWVRQVP<br>EEGLEWVASIDSSGSRTYYAGSVKGRFTI SRDNAKNTLYLQL<br>NSLKAEDTAMYYCAKDHMSWLPRGQGTQVTVSS |
| 251 | AS588 VHH | QVQLVESGGGSVQAGGSLRLSCAASGFTDSSYCGAWFRQVP<br>GKEREGVAIIDRYGGTMYKDSVKGRFTISKDTAKNILYLQM<br>NSLKLEDTAMYYCAAAEYRGSSCDAESGYWGQGTQVTVSS |
| 252 | AS200 VHH | EVQLVESGGGLVQAGDSLRLSCAASGRTFLSYAVGWFRQAP<br>GTEREFVAGIRWSGGSTDYADSVKGRFTISRDNAKNTVYLQ<br>MNSLKPEDTAVYYCAAHRTIATVPNKYEYDTWGQGTQVTV<br>SS |
| 253 | AS988 VHH | QVQLAESGGGSVQTGGSLRLSCEASGVAASGYCMAWFRQA<br>PGKERERVAAISSNDLVAYADSVKGRFTISKDNAKTTLYLQ<br>MNNLKPEDTAMYYCAADGGYGGYCGRLRPGTGYWGQGT<br>QVTVSS |
| 254 | AS675 VHH | AVQLVESGGGLVQAGDSLRLSCTASGRTFLTYAVGWFRQAP<br>GTEREFVAGIRWSGGYTDYADSVKGRFTISRDNAKNTVYLQ<br>MNSLKPEDTAVYYCAAHRTIATIPEKYEYEYWGQGTQVTVS<br>S |
| 255 | AS519 VHH | QIQLVESGGGSAQAGGSLRLSCVVSGNIYNRNFMGWFRQAP<br>GKVREGVAAIYTGTSRTYYADSVKGRFTISQDNAKNTVYLQ<br>MNSLKPEDTAMYYCAADLRDGFWDTGVWNTWGQGTQVT<br>VSS |

EXAMPLES

Example 1: Acquisition of Hybridoma Cell Strain of Antibody

1) Animal immunization. The recombinantly expressed His-tag camel-derived nanobody VHH-His (the amino acid sequence thereof is shown in FIG. 1 or SEQ ID NO: 241) was used as an antigen for animal immunization. The nanobody AS718 is an antigen used for animal immunization, has a C-terminal His tag and contains a total of 121 amino acids. The CDR domain and His tag are underlined in FIG. 1.

8 New Zealand rabbits were subcutaneously immunized with a 1:1 emulsion containing 200 μg of VHH-His and 200 μl of Freund's complete adjuvant (Sigma-Aldrich, CAT #: F5881); the 1:1 emulsion containing 200 μg of VHH-His and Freund's incomplete adjuvant (Sigma-Aldrich, CAT #: F5506) was subcutaneously injected 4 times every 2 weeks to boost immunity to New Zealand rabbits; 4 days before myeloma fusion, the serum antibody titer was detected by ELISA (as shown in FIG. 2), and the serum titer of animal was detected. The results showed that all test values of titers at 1:64,000 were greater than 1.0, and 2 rabbits that met the standards received intraperitoneally and intravenously 400 μg of VHH-His (without adjuvant) for boost immunity.

In FIG. 2, by the mode of indirect ELISA, immunogen AS718 VHH-His was used to coat the ELISA detection plate, and the animal serum was diluted at an initial ratio of 1:1,000 and then diluted to 1:512,000 at 2-fold proportional gradient to carry out ELISA detection. The serum titer of two animals for fusion was measured by OD450 reading, wherein S/N represents Signal-to-Noise (equivalent to the signal-to-noise ratio). The judgement criterion of serum effective titer is that the value is 2.1 folds the blank background value. If the detection value is greater than 1.0 when the serum dilution ratio is 1:64,000, the fusion can be performed. The results showed that the detection value of animal #6119 serum was 1.323 at a dilution ratio of 1:64,000, and the detection value was 0.488 at a serum dilution ratio of 1:512,000; and the detection value of animal #563 serum was 1.637 at a dilution ratio of 1:64,000, and the detection value was 0.528 at a serum dilution ratio of 1:512,000. Since the detection values of the two animals at the serum dilution ratio of 1:512,000 were greater than 2.1 folds the blank background value, the serum effective titers of the two animals were both greater than 1:512,000, and the detection values at 1:64,000 were both greater than 1.0, which met the animal fusion standards.

2) Hybridoma Fusion and Screening

The rabbit spleen was extracted and homogenized to produce a single-cell suspension, and a single-cell suspension of myeloma cells was prepared at the same time. $1.0 \times 10^8$ splenocytes were fused with $1.2 \times 10^5$ myeloma cells by electrofusion; the fused cells were resuspended in 100 ml of DMEM/10% FBS culture medium containing hybridoma selective agents, thymidine, hypoxanthine and aminopterin, and transferred to a 150×96-well plate in a volume of 100 μl with a pipette; and the plate was incubated at 37° C. in 6% $CO_2$. After 9 days of incubation, the indirect ELISA was used to evaluate the binding ability of the antibody in the supernatant to VHH-His, indicating the presence of the antibody to VHH-His.

The ELISA plate was coated with 100 μl/well of 0.5 μg/ml VHH-His or His protein in PBS at 4° C. overnight; the plate was washed with PBS-T (0.05% Tween20) and blocked with 200 μl/well of PBST containing 1% BSA at 37° C. for 0.5 hours; the blocking solution was aspirated and discarded, and 100 μl of hybridoma cell culture supernatant was added to each well and then incubated at room temperature for 1 hour; after the incubation, the supernatant was discarded, and the plate was washed three times with PBST and incubated with 100 μl/well of goat anti-rabbit IgG conjugated with horseradish peroxidase (GenScript Goat Anti-Rabbit IgG Antibody (H&L) [HRP], pAb; CAT #: A00098) at 37° C. for 0.5 hours; the plate was washed five times with PBST, and then a TMB color developing solution was added; and the plate was incubated in the dark at room temperature for 15 minutes. The reaction was stopped by adding 50 μl of 1 M HCl stop solution. The plate was read at 450 nm using a microplate reader. In FIG. 3, by the mode of indirect ELISA, immunogen AS718 VHH-His was used to coat the ELISA detection plate, and the titers of the supernatant stock solutions of 15 parent clones were detected by OD450 reading, and the cross-reactions thereof with the His-tag protein were detected at the same time to exclude non-specific combinations. In the experiment, the positive serum was used as a positive control for immunogen AS718 VHH-His, and the Anti-His antibody was used as a positive control for detection target His-tag protein in the reverse screening. The detection value greater than 0.5 was determined to be positive, and the detection value less than 0.2 was determined to be negative. The results showed that: the binding detection values of the positive serum and the VHH-His, the positive serum and the His-tag protein, the Anti-His antibody and the VHH-His, and the Anti-His antibody and the His-tag protein were respectively 2.953, 0.747, 2.906 and 2.858, all of which were greater than 0.5 and determined to be positive, that is, the positive controls were effective, wherein the binding detection value of the positive serum and the His-tag protein was 0.747, indicating that the antibody for the His-tag protein was still produced in the fusion animal. The ELISA reaction detection values of the supernatant stock solutions of 15 parent clones and immunogen AS718 VHH-His were respectively 2.758, 3.060, 2.908, 2.883, 2.893, 2.556, 2.913, 2.655, 2.561, 2.356, 3.059, 2.130, 2.083, 2.454 and 2.428, all of which were greater than 0.5, and the reactions of the supernatants of 15 parent clones to VHH-His were determined to be positive; the ELISA reaction detection values of the supernatant stock solutions of 15 parent clones and the His-tag protein were respectively 0.074, 0.130, 0.091, 0.102, 0.082, 0.100, 0.121, 0.083, 0.091, 0.114, 0.123, 0.085, 0.112, 0.082 and 0.079, all of which were less than 0.2, and the reactions of the supernatant of 15 parent clones to the His-tag protein were determined to be negative, that is, there was no cross-reactions with unrelated His-tag proteins.

3) Hybridoma Subcloning (the Limiting Dilution Method is Used for Subcloning)

The cells were serially diluted in a DMEM/10% FBS culture medium containing hybridoma cell selection agents thymidine, hypoxanthine and aminopterin until the cell density reached 5-15 cells/ml, and then the number of cells were determined by using a hemocytometer; for each hybridoma, 200 μl of cell solutions were transferred to 96 wells at a density of 1-3 cells/well with a pipette; after the culture was cultured at 37° C. in 5% CO$_2$ for 1 week, the supernatant was subjected to the described ELISA binding test to evaluate the presence of the antibody to VHH. The ELISA test data of stable subclones is shown in FIG. 4 (titer detection of supernatant of stable subclones by ELISA): by the mode of indirect ELISA, the ELISA detection plate was coated with immunogen AS718 VHH-His, the positive animal serum diluted at 1:1,000 was used as a positive control, and the titers of cell supernatants of 15 stable parent clones after subcloning were detected by OD450 reading. The cell supernatant stock solution was added to the first well and successively diluted to 1:81 with a 3-fold ratio. If the detection value of the cell supernatant at a dilution ratio of 1:9 was greater than 1.0, antibody production can be carried out. The results showed that the detection values of cell supernatants of 15 clones at a dilution ratio of 1:9 were 2.460, 1.954, 1.945, 2.143, 2.243, 2.047, 2.064, 2.268, 2.197, 1.528, 2.377, 1.530, 2.485, 1.929 and 1.475, all of which were greater than 1.0 and met the standards for stable clones of hybridoma cells, and thus antibody production can be continued.

Example 2: Sequencing of Variable Region of Antibody and Antibody Recombinant Production The total RNA was extracted from $3\times10^6$-$5\times10^6$ hybridoma cells with TRIzol (Ambion, CAT #: 15596-026) and reverse transcribed into cDNA using an antibody sub-type-specific primer and a universal primer (Takara Prime-Script™ 1st Strand cDNA Synthesis Kit, CAT #: 6110A). Subsequently, heavy chain and light chain variable region fragments of rabbit immunoglobulin were amplified by RACE PCR, and the resulting PCR fragments were sub-cloned into a pMD18-T vector system (Takara, CAT #: 6011); and a vector-specific primer was used to sequence the inserted fragments. Finally, nucleotide/protein sequences of heavy chain and light chain variable regions of 15 mono-clonal antibodies were obtained, including clone R166.C5, clone R166.G3, clone R166.F2, clone R166.G8, clone R166.H9, clone R166.D1, clone R166.G10, clone R166.H10, clone R166.F9, clone R166.G2, clone R166.E5, clone R166.E3, clone R166.H8, clone R166.E7, and clone R166.A5.

The antibodies were all produced by recombinant expression, taking a preferred clone as an example.

The DNA fragments encoding a light chain variable region+a constant region (with an amino acid sequence shown in SEQ ID NO: 244 and a nucleotide sequence shown in SEQ ID NO: 245) and a heavy chain variable region+a constant region (with an amino acid sequence shown in SEQ ID NO: 242 and a nucleotide sequence shown in SEQ ID NO: 243) were respectively synthesized and inserted into a pTT5 expression vector to form an expression plasmid; CHO-3E7 cells were co-transfected with the described plasmids and cultured in a shake flask at 37° C. for 6 days, and the supernatant was collected for antibody purification; 0.2 M NaOH was used to remove the pyrogen of pipelines and protein A column, and then the column was re-equilibrated with a buffer containing 0.05 M Tris and 1.5 M NaCl (pH 8.0); and the harvested cell culture supernatant was diluted at 1:1 with 2× the described buffer and sterilized by filtration. The filtered supernatant and protein A column were incubated for 2 hours at room temperature; the column was washed with 1× the described buffer, and then IgG was eluted with sterile 0.1 M sodium citrate (pH 3.5); and the eluate was collected and neutralized with one-ninth volume of sterile 1 M Tris-HCl (pH 9.0); and under sterile conditions, the product buffer was exchanged to PBS (pH 7.4) to remove any elution buffer, and the sample was concentrated. After concentration, the antibodies were quantified by OD280 nm using an extinction coefficient Ec of 1.43 (0.1%). The purified antibodies were analyzed by SDS-PAGE using 10% precast gel (GenScript) and a BioRad electrophoresis system. The gel was stained with eStain2.0 (GenScript), and the molecular size and purity were estimated by comparing the stained band with Protein Ladder (GenScript). The purity identification results of 15 antibodies are shown in FIGS. 5a and 5b. Under non-reducing conditions, the two heavy chains and two light chains of the antibodies still maintained a tetravalent structure by disulfide bonds. Only one band of interest appeared in the electrophoretic staining result, displaying a molecular weight slightly lower than the actual molecular weight and comparable to the 116 kDa marker band. However, under reducing conditions, the disulfide bond structure in the antibodies was destroyed due to the presence of reducing agents; and the heavy and light chains of the antibodies were separated, leading to separate electrophoretic bands during electrophoresis, and the sizes thereof were 55 kDa and 25 kDa, respectively. The results showed that the purity of all 15 antibodies was greater than 90%, which met the standards for antibody production and purification and can be used for subsequent experimental studies.

Example 3: Binding of Antibody to Recombinant Camel Nanobody

The binding ability of the purified antibodies of 15 camel-derived nanobodies to 10 different camel-derived nanobodies VHH (with the amino acid sequences shown in SEQ ID NO: 246-255, respectively) was evaluated by the indirect ELISA method.

The ELISA plate was coated with 10 different VHHs at 0.5 m/ml in 100 μl/well of PBS at 4° C. overnight, respectively; the plate was washed with PBS-T (0.05% Tween) and blocked with 200 μl/well of PBST containing 1% BSA at 37° C. for 0.5 hours; the blocking solution was aspirated and discarded, and 100 μl of 1 μg/ml purified antibodies were added to the first well, diluted in a 3-fold gradient for a total of 11 test concentration gradients and incubated at room temperature for 1 hour; the plate was washed three times with PBST and incubated with 100 μl/well of goat anti-rabbit IgG conjugated with horseradish peroxidase (GenScript Goat Anti-Rabbit IgG Antibody (H&L) [HRP], pAb; CAT #: A00098) at 37° C. for 0.5 hours; the plate was washed five times with PBST, and then a TMB color developing solution was added; and the plate was incubated in the dark at room temperature for 15 minutes. The reaction was stopped by adding 50 μl of 1 M HCl stop solution. The plate was read at 450 nm using a microplate reader; and the binding abilities of 15 clones to VHH-His were obtained (as shown in FIGS. 6a and 6b). The results showed that the affinities of the 15 antibodies of camel-derived nanobodies to different camel-derived nanobodies were different. On one hand, the affinities of the antibody of the same camel-derived nanobody to different camel-derived nanobodies were different; on the other hand, the affinities of different antibodies of camel-derived nanobodies to the same camel-derived nanobody were different. However, on the whole, all the 15 purified antibodies can be recognized with 10 different camel-derived nanobodies. The EC50 calculated according to the ELISA concentration gradient experiment indicated that these antibodies showed a relatively high affinity for antigens.

The sequences of the described 10 different camel-derived nanobodies and the sequence of AS718 nanobody used for the immune animals in Example 1 were analyzed by Kabat to obtain the sequences of framework regions FR1, FR2, FR3 and FR4, and then the sequence identity was analyzed using BioEdit software. The results showed that the sequence identity of FR1 region, FR2 region, FR3 region, FR4 region, and all the framework regions was 53.3%, 35.7%, 50%, 54.5% and 49.4%, respectively, see FIG. 7.

Moreover, the framework regions of the described 10 camel-derived nanobodies and AS718 nanobodies have 74.7% (AS154, AS325), 77.0% (AS587), 79.3% (AS675), 80.5% (AS200, AS519), 81.6% (AS656), 82.8% (AS588, AS988) and 83.9% (AS673) sequence identity, respectively.

Similarly, the full length VHH domains of the described 10 camel-derived nanobodies and AS718 nanobodies have 62.3% (AS154), 62.9% (AS200), 63.6% (AS325), 64.8% (AS656), 66.1% (AS675, AS673), 66.4% (AS587, AS988), 68.0% (AS588), 69.9% (AS519) sequence identity, respectively. All 11 nanobodies have 37.7% identity.

Example 4: Determination of Affinity of Antibody to Multiple Camel-Derived Nanobodies In an exemplary embodiment, the affinity levels of the antibody clone R166.C5 to multiple camel-derived nanobodies were determined using Biacore 8K instrument (GE healthcare) by SPR experimental technique.

Pretreatment of CMS chip: after equilibrating with 10 μl/min of equilibration buffer HBS for 5 minutes, the chip was treated with 10 μl/min of NHS/EDC activators for 7 minutes, and then the coupled anti-His antibody (GenScript, CAT #: A00186) was added at 10 μl/min and reacted for 7 minutes; and the chip was finally blocked with 10 μl/min of aminoethanol. Capture of camel-derived nanobodies: after equilibrating with 10 μl/min of equilibration buffer HBS for 5 minutes, 20 μl/ml of 10 VHH-His antibodies were added respectively at 30 μl/min and fully reacted for 1 minute; the affinity levels of the antibodies were determined in a mobile phase at an antibody concentration of 200 nM and a flow rate of 30 μl/min, wherein the immunogen AS718 was used as a positive control for camel-derived nanobodies. The results showed that the affinity of the cloned antibody to the immunogen AS718 reached a level of 3.47 pmol. At the same time, the affinities of 6 antibodies AS325, AS656, AS673, AS588, AS988 and AS519 in the detected 10 camel-derived nanobodies to the antibody reached 4.04 pmol, 1.34 pmol, 4.36 pmol, 7.09 pmol, 7.08 pmol and 1.66 pmol, respectively. The camel-derived nanobody with the lowest affinity to the cloned antibody was AS587, and the affinity reached 2.2 nmol. The data indicates that all the antibodies of the clone R166.C5 camel-derived nanobodies have high affinities to 10 different camel-derived nanobodies (as shown in FIG. 8).

Example 5: Use of Antibody in Separation of PBMC Specific for Camel-Derived Heavy-Chain Antibody In an exemplary embodiment, the PBMCs specific for heavy-chain antibodies were isolated using fluorescently labeled antibodies of camelid-derived nanobodies by flow cytometry. The PBMC cells of non-immunized camel were used in the present invention.

$5 \times 10^6$ PBMC cells were selected and used for analysis. The cells were washed once with 500 μl of FACS buffer (PBS, 1% BSA) and centrifuged at 1000 rpm for 5 minutes, and the supernatant was discarded; The PBMC cells were resuspended in 200 μl of FACS buffer, and 2 μg of fluorescein phycoerythrin (PE)-labeled antibodies of camel-derived nanobodies, R166.C5, R166.H8, R166.H9, R166.E7 and R166.G8, were added; under dark conditions, the cells were incubated in an ice bath for 15 minutes, then washed once with 500 μl of FACS buffer and centrifuged at 1000 rpm for 5 minutes, and the supernatant was discarded; the cells were fixed with 2% paraformaldehyde solution for 30 minutes, washed once with 500 μl of FACS buffer and centrifuged at 1000 rpm for 5 minutes, and the supernatant was discarded; the cells were resuspended in 200 μl of FACS buffer, and the PBMC cells specific for heavy-chain antibodies were subjected to flow cytometric sorting. FACS detection results are shown in FIG. 12. The proportions of PBMC cells specific for 5 PE-labeled heavy-chain antibodies obtained by FACS sorting of different clonal antibodies were 22.83%, 23.58%, 24.24%, 23.33% and 17.24%, respectively, which met the theoretical value (about 20%-30%) and showed that all the 5 antibodies have good specificity for heavy-chain antibodies.

Example 6: Use of Antibody in Purification of Camel-Derived Heavy-Chain Antibody In an exemplary embodiment, the antibody of the present invention was used to purify heavy-chain antibodies in the serum of *Lama glama* or *Vicugna pacos*, and the serum of a non-immunized alpaca was used in the present invention.

The antibodies of camel-derived nanobodies (exemplary anti-VHH antibodies) were coupled to NETS-activated magnetic beads at the following mass/volume ratios (antibody:magnetic bead=3:1; 4:1; 5:1; 6:1; 7:1; 8:1) to obtain purification mediums of VHH nanobodies. 1 ml of alpaca serum was selected, diluted by adding 4 ml of PBS and mixed thoroughly; 1 ml of magnetic bead purification medium was added, and the mixture was incubated at 4° C. for 1 hour; after the magnetic beads were adsorbed using a magnetic stand, the supernatant was discarded, and the magnetic beads were washed 3 times with PBST; heavy-chain antibodies were eluted with sterile 0.1 M sodium citrate (pH 3.5); and the eluate was collected and neutralized with one-ninth volume of sterile 1 M Tris-HCl (pH 9.0); and under sterile conditions, the product buffer was exchanged to PBS (pH 7.4) to remove any elution buffer, and the sample was concentrated. After concentration, the antibodies were quantified by OD280 nm using an extinction coefficient Ec of 1.43 (0.1%).

The purified antibodies (including the serum supernatant before magnetic bead purification, the eluate after magnetic bead purification, and the eluted sample after purification) were analyzed by SDS-PAGE using 10% precast gel (GenScript, CAT #: M00665) and a BioRad electrophoresis system. The gel was stained with eStain® L1 Protein Staining System (GenScript), and the molecular size and purity were estimated by comparing the stained band with Protein Ladder. As shown in FIG. 13, the molecular weights of the labeled Camelidae IgG2 and IgG3 antibodies were 46 KD and 43 KD, respectively, and the obtained magnetic beads can be used to specifically purify heavy-chain antibodies. After purification, the overall purity of heavy-chain antibodies IgG2 and IgG3 were respectively 77.4%, 78.3%, 71.6%, 80.1%, 81.1% and 73.8%.

Example 7: Use of Antibodies in CART Cell Therapy-Flow Cytometric Identification of CART Cells When a camel-derived nanobody is used to construct a chimeric receptor in CART cell therapy, the antibody of the present invention can be used for flow cytometric identification of CART cells.

CART cells that meet the described conditions were mixed with naïve T cells at the following proportions (0%, 10%, 20%, 40%, 80% and 95%) to prepare cell samples to be detected; $5 \times 10^5$ cells were selected in each sample. The cells were washed once with 500 μl of FACS buffer (PBS, 1% BSA) and centrifuged at 1000 rpm for 5 minutes, and the supernatant was discarded; the cells were resuspended in selected 400 μl of FACS buffer, and 4.5 μg of biotin-labeled antibody clone R166.A5 of camel-derived nanobodies was added; the cells were incubated in an ice bath for 45 minutes, then washed once with 500 μl of FACS buffer and centrifuged at 1000 rpm for 5 minutes, and the supernatant was discarded; the cells were resuspended in selected 500 μl of FACS buffer, and 0.2 μg of PE-labeled streptavidin (Biolegend, CAT #: 740452) was added; the cells were incubated at room temperature for 15 minutes, then washed once with 500 μl of FACS buffer and centrifuged at 1000 rpm for 5 minutes, and the supernatant was discarded; the cells were fixed with 2% paraformaldehyde solution for 30 minutes, washed once with 500 μl of FACS buffer and centrifuged at 1000 rpm for 5 minutes, and the supernatant was discarded; The cells were resuspended in 200 μl of FACS buffer and subjected to flow cytometric analysis. The analysis results are shown in FIG. 9. The CART cells were mixed with naïve T cells at different fixed ratios of 0%, 10%, 20%, 40%, 80% and 95%. The flow cytometry staining identification was performed by the biotin-labeled clone R166.A5 antibody and PE-labeled streptavidin. The results showed that the proportions of CAR-positive cells were respectively 0.01%, 9.72%, 20.9%, 39.3%, 80.5% and 93.7%, and the deviations between the results and the premix proportions were less than ±1.5%. The data showed that the antibody can be well used in the detection of CART cells using a camel-derived nanobody to construct a chimeric receptor. The antibody can well recognize CAR-positive T cells.

Example 8: Use of Antibodies in CART Cell Therapy-Magnetic Separation of CART Cells When a camel-derived nanobody is used to construct a chimeric receptor in CART cell therapy, the antibody of the present invention can be used for magnetic separation of CART cells.

The cells were counted, and in an exemplary embodiment, the number of CART cells to be separated was $1 \times 10^7$; the cells were centrifuged at 1000 rpm for 10 minutes, and the supernatant was discarded; the cells were fully resuspended in 100 μl of PBE buffer (PBS, pH 7.2, 0.5% BSA, 2 mM EDTA); 2 μg of antibody clone R166.A5 of biotin-labeled camel-derived nanobodies was added and mixed thoroughly, and then the mixture were incubated at 4° C. for 10 minutes; the cells were washed once with 2 ml of PBE buffer, and the cells were fully resuspended in 100 μl of PBE buffer; 20 μl of anti-biotin magnetic beads (Miltenyi) were added and mixed thoroughly, and then the mixture was incubated at 4° C. for 10 minutes; the cells were separated using a magnetic stand, and the obtained cells were subjected to flow cytometric analysis to verify the effect of magnetic separation; as shown in FIG. 10, naïve T cells were used as CAR-negative cell control, and a mixture of 10% CAR-positive T cells and naïve T cells was used as a positive sample to be separated; $1 \times 10^7$ cells were taken respectively and subjected to the magnetic separation of CART cells by biotin-labeled clone R166.A5 antibody and anti-biotin magnetic beads; and the effect of magnetic separation of CART cells was detected by flow cytometry. The results showed that the proportion of CAR-negative cells detected to be CAR-positive was less than 0.5% both before and after magnetic separation, which is a background noise signal; and after the magnetic separation of CAR-positive cells, the proportion of CAR-positive cells increased from 10% (premix) to 88.6% (after separation). The data showed that the antibody can be well used in the magnetic separation of CART cells. The results showed that the antibody can be well used in the magnetic separation of CART cells.

What is claimed is:

1. An antibody or antigen-binding fragment thereof, wherein the antibody contains a heavy chain variable region and a light chain variable region, wherein (A) the heavy chain variable region comprises heavy chain complementarity determining region (HCDR) 1, HCDR2 and HCDR3, and (B) the light chain variable region comprises light chain complementarity determining region (LCDR) 1, LCDR2, and LCDR3, wherein the antibody contains (1) HCDR1 shown in SEQ ID NO: 14, HCDR2 shown in SEQ ID NO: 29, HCDR3 shown in SEQ ID NO: 44, LCDR1 shown in SEQ ID NO: 59, LCDR2 shown in SEQ ID NO: 74 and LCDR3 shown in SEQ ID NO: 89;

(2) HCDR1 shown in SEQ ID NO: 4, HCDR2 shown in SEQ ID NO: 19, HCDR3 shown in SEQ ID NO: 34, LCDR1 shown in SEQ ID NO: 49, LCDR2 shown in SEQ ID NO: 64 and LCDR3 shown in SEQ ID NO: 79;

(3) HCDR1 shown in SEQ ID NO: 15, HCDR2 shown in SEQ ID NO: 30, HCDR3 shown in SEQ ID NO: 45, LCDR1 shown in SEQ ID NO: 60, LCDR2 shown in SEQ ID NO: 75 and LCDR3 shown in SEQ ID NO: 90;

(4) HCDR1 shown in SEQ ID NO: 1, HCDR2 shown in SEQ ID NO: 16, HCDR3 shown in SEQ ID NO: 31, LCDR1 shown in SEQ ID NO: 46, LCDR2 shown in SEQ ID NO: 61 and LCDR3 shown in SEQ ID NO: 76;

(5) HCDR1 shown in SEQ ID NO: 2, HCDR2 shown in SEQ ID NO: 17, HCDR3 shown in SEQ ID NO: 32, LCDR1 shown in SEQ ID NO: 47, LCDR2 shown in SEQ ID NO: 62 and LCDR3 shown in SEQ ID NO: 77;

(6) HCDR1 shown in SEQ ID NO: 3, HCDR2 shown in SEQ ID NO: 18, HCDR3 shown in SEQ ID NO: 33, LCDR1 shown in SEQ ID NO: 48, LCDR2 shown in SEQ ID NO: 63 and LCDR3 shown in SEQ ID NO: 78;

(7) HCDR1 shown in SEQ ID NO: 5, HCDR2 shown in SEQ ID NO: 20, HCDR3 shown in SEQ ID NO: 35, LCDR1 shown in SEQ ID NO: 50, LCDR2 shown in SEQ ID NO: 65 and LCDR3 shown in SEQ ID NO: 80;

(8) HCDR1 shown in SEQ ID NO: 6, HCDR2 shown in SEQ ID NO: 21, HCDR3 shown in SEQ ID NO: 36, LCDR1 shown in SEQ ID NO: 66 and LCDR3 shown in SEQ ID NO: 81;

(9) HCDR1 shown in SEQ ID NO: 7, HCDR2 shown in SEQ ID NO: 22, HCDR3 shown in SEQ ID NO: 37, LCDR1 shown in SEQ ID NO: 52, LCDR2 shown in SEQ ID NO: 67 and LCDR3 shown in SEQ ID NO: 82;

(10) HCDR1 shown in SEQ ID NO: 8, HCDR2 shown in SEQ ID NO: 23, HCDR3 shown in SEQ ID NO: 38, LCDR1 shown in SEQ ID NO: 53, LCDR2 shown in SEQ ID NO: 68 and LCDR3 shown in SEQ ID NO: 83;

(11) HCDR1 shown in SEQ ID NO: 9, HCDR2 shown in SEQ ID NO: 24, HCDR3 shown in SEQ ID NO: 39, LCDR1 shown in SEQ ID NO: 54, LCDR2 shown in SEQ ID NO: 69 and LCDR3 shown in SEQ ID NO: 84;

(12) HCDR1 shown in SEQ ID NO: 10, HCDR2 shown in SEQ ID NO: 25, HCDR3 shown in SEQ ID NO: 40, LCDR1 shown in SEQ ID NO: 55, LCDR2 shown in SEQ ID NO: 70 and LCDR3 shown in SEQ ID NO: 85;

(13) HCDR1 shown in SEQ ID NO: 11, HCDR2 shown in SEQ ID NO: 26, HCDR3 shown in SEQ ID NO: 41, LCDR1 shown in SEQ ID NO: 56, LCDR2 shown in SEQ ID NO: 71 and LCDR3 shown in SEQ ID NO: 86;

(14) HCDR1 shown in SEQ ID NO: 12, HCDR2 shown in SEQ ID NO: 27, HCDR3 shown in SEQ ID NO: 42, LCDR 1 shown in SEQ ID NO: 57, LCDR2 shown in SEQ ID NO: 72 and LCDR3 shown in SEQ ID NO: 87; or

(15) HCDR1 shown in SEQ ID NO: 13, HCDR2 shown in SEQ ID NO: 28, HCDR3 shown in SEQ ID NO: 43, LCDR1 shown in SEQ ID NO: 58, LCDR2 shown in SEQ ID NO: 73 and LCDR3 shown in SEQ ID NO: 88.

2. The antibody or the antigen-binding fragment thereof of claim 1, wherein the amino acid sequence of the heavy chain variable region is selected from an amino acid sequence shown in SEQ ID NO: 91, 92, 93, 94, 95, 96, 97, 98, 99, 100, 101, 102, 103, 104 or 105 or an amino acid sequence having at least 90% identity thereto.

3. The antibody or the antigen-binding fragment thereof of claim 1, wherein the amino acid sequence of the light chain variable region is selected from an amino acid sequence shown in SEQ ID NO: 106, 107, 108, 109, 110, 111, 112, 113, 114, 115, 116, 117, 118, 119 or 120 or an amino acid sequence having at least 90% identity thereto.

4. The antibody or the antigen-binding fragment thereof of claim 1, wherein the antibody contains (1) a heavy chain variable region shown in SEQ ID NO: 104 and a light chain variable region shown in SEQ ID NO: 119;

(2) a heavy chain variable region shown in SEQ ID NO: 94 and a light chain variable region shown in SEQ ID NO: 109;

(3) a heavy chain variable region shown in SEQ ID NO: 105 and a light chain variable region shown in SEQ ID NO: 120;

(4) a heavy chain variable region shown in SEQ ID NO: 91 and a light chain variable region shown in SEQ ID NO: 106;

(5) a heavy chain variable region shown in SEQ ID NO: 92 and a light chain variable region shown in SEQ ID NO: 107;

(6) a heavy chain variable region shown in SEQ ID NO: 93 and a light chain variable region shown in SEQ ID NO: 108;

(7) a heavy chain variable region shown in SEQ ID NO: 95 and a light chain variable region shown in SEQ ID NO: 110;

(8) a heavy chain variable region shown in SEQ ID NO: 96 and a light chain variable region shown in SEQ ID NO: 111;

(9) a heavy chain variable region shown in SEQ ID NO: 97 and a light chain variable region shown in SEQ ID NO: 112;

(10) a heavy chain variable region shown in SEQ ID NO: 98 and a light chain variable region shown in SEQ ID NO: 113;

(11) a heavy chain variable region shown in SEQ ID NO: 99 and a light chain variable region shown in SEQ ID NO: 114;

(12) a heavy chain variable region shown in SEQ ID NO: 100 and a light chain variable region shown in SEQ ID NO: 115;

(13) a heavy chain variable region shown in SEQ ID NO: 101 and a light chain variable region shown in SEQ ID NO: 116;

(14) a heavy chain variable region shown in SEQ ID NO: 102 and a light chain variable region shown in SEQ ID NO: 117; or

(15) a heavy chain variable region shown in SEQ ID NO: 103 and a light chain variable region shown in SEQ ID NO: 118.

5. The antibody or the antigen-binding fragment thereof of claim 1, specifically binding to a VHH domain.

6. The antibody or the antigen-binding fragment thereof of claim 5, wherein the VHH domain is a VHH domain of a camel-derived antibody.

7. The antibody or the antigen-binding fragment thereof of claim 6, wherein the camel-derived antibody is a single-domain antibody or a heavy-chain antibody derived from *Camelus dromedarius, Camelus bactrianus, Vicugna* pacos or *Lama glama.*

8. The antibody or the antigen-binding fragment thereof of claim 5, specifically binding to a VHH domain shown in SEQ ID NO: 241 or a VHH domain having at least 60% amino acid sequence identity to SEQ ID NO: 241.

9. The antibody or the antigen-binding fragment thereof of claim 5, binding to the VHH domain at a conformational epitope in a framework region.

10. The antibody or the antigen-binding fragment thereof of claim 5, specifically binding to a framework region of the VHH domain shown in SEQ ID NO: 241 or a framework region having at least 70% amino acid sequence identity to the framework region of the VHH domain shown in SEQ ID NO: 241.

11. The antibody or the antigen-binding fragment thereof of claim 1, selected from Fab, $F(ab')_2$, scFv, a chimeric antibody, a humanized antibody, a diabody and a multispecific antibody.

12. One or more polynucleotides, encoding the antibody or the antigen-binding fragment thereof of claim 1.

13. One or more vectors, comprising the one or more polynucleotides of claim 12.

14. A host cell, comprising the one or more polynucleotides of claim 12.

15. A method for detecting a VHH domain, comprising adding the antibody or the antigen-binding fragment thereof of claim 1 to a sample that is known or suspected to contain the VHH domain and detecting a complex formed between the antibody or the antigen-binding fragment thereof and the VHH domain.

16. A method for separating a VHH domain, comprising adding the antibody or the antigen-binding fragment thereof of claim 1 to a sample that is known or suspected to contain the VHH domain and separating a complex formed between the antibody or the antigen-binding fragment thereof and the VHH domain.

17. The method of claim 15, wherein the VHH domain is in a camel-derived antibody and/or a chimeric antigen receptor.

18. The method of claim 17, wherein the chimeric antigen receptor is on an immune cell.

* * * * *

SEQUENCE LISTING

<160> NUMBER OF SEQ ID NOS: 255

<210> SEQ ID NO 1
<211> LENGTH: 5
<212> TYPE: PRT
<213> ORGANISM: Artificial sequence
<220> FEATURE:
<223> OTHER INFORMATION: R166.C5 HCDR1

<400> SEQUENCE: 1

Asn Phe Ala Met Ser
1               5

<210> SEQ ID NO 2
<211> LENGTH: 5
<212> TYPE: PRT
<213> ORGANISM: Artificial sequence
<220> FEATURE:
<223> OTHER INFORMATION: R166.H9 HCDR1

<400> SEQUENCE: 2

Asn Tyr Asn Met Ile
1               5

<210> SEQ ID NO 3
<211> LENGTH: 5
<212> TYPE: PRT
<213> ORGANISM: Artificial sequence
<220> FEATURE:
<223> OTHER INFORMATION: R166.F2 HCDR1

<400> SEQUENCE: 3

Ser His Asp Met Ser
1               5

<210> SEQ ID NO 4
<211> LENGTH: 5
<212> TYPE: PRT
<213> ORGANISM: Artificial sequence
<220> FEATURE:
<223> OTHER INFORMATION: R166.H8 HCDR1

<400> SEQUENCE: 4

Ser Phe Ala Met Ser
1               5

<210> SEQ ID NO 5
<211> LENGTH: 5
<212> TYPE: PRT
<213> ORGANISM: Artificial sequence
<220> FEATURE:
<223> OTHER INFORMATION: R166.E7 HCDR1

<400> SEQUENCE: 5

Ser Phe Ala Met Ser
1               5

<210> SEQ ID NO 6
<211> LENGTH: 6
<212> TYPE: PRT
<213> ORGANISM: Artificial sequence
<220> FEATURE:
<223> OTHER INFORMATION: R166.G8 HCDR1

<400> SEQUENCE: 6

Asn Ile Tyr Trp Ile Cys
1               5

```
<210> SEQ ID NO 7
<211> LENGTH: 5
<212> TYPE: PRT
<213> ORGANISM: Artificial sequence
<220> FEATURE:
<223> OTHER INFORMATION: R166.F9 HCDR1

<400> SEQUENCE: 7

Ser Asn Ala Met Gly
1               5

<210> SEQ ID NO 8
<211> LENGTH: 5
<212> TYPE: PRT
<213> ORGANISM: Artificial sequence
<220> FEATURE:
<223> OTHER INFORMATION: R166.G2 HCDR1

<400> SEQUENCE: 8

Ser Asp Ala Met Ser
1               5

<210> SEQ ID NO 9
<211> LENGTH: 5
<212> TYPE: PRT
<213> ORGANISM: Artificial sequence
<220> FEATURE:
<223> OTHER INFORMATION: R166.D1 HCDR1

<400> SEQUENCE: 9

Asn Tyr Asp Met Ile
1               5

<210> SEQ ID NO 10
<211> LENGTH: 5
<212> TYPE: PRT
<213> ORGANISM: Artificial sequence
<220> FEATURE:
<223> OTHER INFORMATION: R166.G10 HCDR1

<400> SEQUENCE: 10

Ser Ser Ala Val Ser
1               5

<210> SEQ ID NO 11
<211> LENGTH: 5
<212> TYPE: PRT
<213> ORGANISM: Artificial sequence
<220> FEATURE:
<223> OTHER INFORMATION: R166.G3 HCDR1

<400> SEQUENCE: 11

Arg Tyr Ala Met Gly
1               5

<210> SEQ ID NO 12
<211> LENGTH: 5
<212> TYPE: PRT
<213> ORGANISM: Artificial sequence
<220> FEATURE:
<223> OTHER INFORMATION: R166.E5 HCDR1

<400> SEQUENCE: 12

Gly Tyr Tyr Met Ile
1               5
```

-continued

```
<210> SEQ ID NO 13
<211> LENGTH: 5
<212> TYPE: PRT
<213> ORGANISM: Artificial sequence
<220> FEATURE:
<223> OTHER INFORMATION: R166.E3 HCDR1

<400> SEQUENCE: 13

Ser Cys Val Leu Ile
1               5

<210> SEQ ID NO 14
<211> LENGTH: 5
<212> TYPE: PRT
<213> ORGANISM: Artificial sequence
<220> FEATURE:
<223> OTHER INFORMATION: R166.A5 HCDR1

<400> SEQUENCE: 14

Asn Tyr Thr Val Ile
1               5

<210> SEQ ID NO 15
<211> LENGTH: 5
<212> TYPE: PRT
<213> ORGANISM: Artificial sequence
<220> FEATURE:
<223> OTHER INFORMATION: R166.H10 HCDR1

<400> SEQUENCE: 15

Ser Tyr Trp Met Ser
1               5

<210> SEQ ID NO 16
<211> LENGTH: 16
<212> TYPE: PRT
<213> ORGANISM: Artificial sequence
<220> FEATURE:
<223> OTHER INFORMATION: R166.C5 HCDR2

<400> SEQUENCE: 16

Ile Ile Tyr Ser Gly Gly Thr Arg Asp Tyr Ala Thr Trp Ala Lys Gly
1               5                   10                  15

<210> SEQ ID NO 17
<211> LENGTH: 17
<212> TYPE: PRT
<213> ORGANISM: Artificial sequence
<220> FEATURE:
<223> OTHER INFORMATION: R166.H9 HCDR2

<400> SEQUENCE: 17

Met Ile Gly Asp Gly Asp Asp Ala Ala Trp Tyr Ala Ser Trp Ala Lys
1               5                   10                  15

Gly

<210> SEQ ID NO 18
<211> LENGTH: 17
<212> TYPE: PRT
<213> ORGANISM: Artificial sequence
<220> FEATURE:
<223> OTHER INFORMATION: R166.F2 HCDR2

<400> SEQUENCE: 18

Tyr Ile Tyr Tyr Gly Ser Gly Ser Thr Asp Tyr Ala Ser Trp Ala Glu
1               5                   10                  15
```

Gly

```
<210> SEQ ID NO 19
<211> LENGTH: 17
<212> TYPE: PRT
<213> ORGANISM: Artificial sequence
<220> FEATURE:
<223> OTHER INFORMATION: R166.H8 HCDR2

<400> SEQUENCE: 19

Ile Ile Tyr Ala Thr Gly Gly Thr Arg Asp Tyr Ala Thr Trp Ala Ala
1               5                   10                  15

Gly

<210> SEQ ID NO 20
<211> LENGTH: 16
<212> TYPE: PRT
<213> ORGANISM: Artificial sequence
<220> FEATURE:
<223> OTHER INFORMATION: R166.E7 HCDR2

<400> SEQUENCE: 20

Ile Ile Tyr Thr Gly Gly Thr Arg Asp Tyr Ala Thr Trp Ala Lys Gly
1               5                   10                  15

<210> SEQ ID NO 21
<211> LENGTH: 18
<212> TYPE: PRT
<213> ORGANISM: Artificial sequence
<220> FEATURE:
<223> OTHER INFORMATION: R166.G8 HCDR2

<400> SEQUENCE: 21

Cys Ile Asn Ser Gly Ser Asn Ser Tyr Thr Tyr Tyr Ala Asn Trp Val
1               5                   10                  15

Asp Gly

<210> SEQ ID NO 22
<211> LENGTH: 16
<212> TYPE: PRT
<213> ORGANISM: Artificial sequence
<220> FEATURE:
<223> OTHER INFORMATION: R166.F9 HCDR2

<400> SEQUENCE: 22

Leu Ile Asn Ile Tyr Asp Asn Thr Tyr Tyr Ala Ser Trp Ala Lys Gly
1               5                   10                  15

<210> SEQ ID NO 23
<211> LENGTH: 16
<212> TYPE: PRT
<213> ORGANISM: Artificial sequence
<220> FEATURE:
<223> OTHER INFORMATION: R166.G2 HCDR2

<400> SEQUENCE: 23

Leu Ile Asn Arg Tyr Gly Asn Thr Tyr Tyr Ala Ser Trp Ala Lys Gly
1               5                   10                  15

<210> SEQ ID NO 24
<211> LENGTH: 16
<212> TYPE: PRT
<213> ORGANISM: Artificial sequence
<220> FEATURE:
<223> OTHER INFORMATION: R166.D1 HCDR2
```

<400> SEQUENCE: 24

Val Ile Tyr Pro Thr Gly Thr Thr Tyr Tyr Ala Asn Trp Val Lys Gly
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: R166.G10 HCDR2

<400> SEQUENCE: 25

Ile Ile Gly Ser Gly Gly Ser Thr Tyr Tyr Ala Ser Trp Val Asn Gly
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: R166.G3 HCDR2

<400> SEQUENCE: 26

Ile Ile Gly Tyr Gly Gly Asn Thr Asn Tyr Ala Asn Trp Ala Lys Gly
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: R166.E5 HCDR2

<400> SEQUENCE: 27

Ile Val Thr Ser Ser Gly Ser Thr His Tyr Ala Ser Trp Ala Asn Gly
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: R166.E3 HCDR2

<400> SEQUENCE: 28

Phe Ile Tyr Gly Ser Gly Asn Ala Tyr Tyr Ala Asn Trp Ala Lys Gly
1               5                   10                  15

<210> SEQ ID NO 29
<211> LENGTH: 16
<212> TYPE: PRT
<213> ORGANISM: Artificial sequence
<220> FEATURE:
<223> OTHER INFORMATION: R166.A5 HCDR2

<400> SEQUENCE: 29

Ile Ile Phe Gly Ser Gly Gly Thr Tyr Tyr Ala Thr Trp Ala Glu Gly
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: R166.H10 HCDR2

-continued

```
<400> SEQUENCE: 30

Ile Ile Ser Gly Ser Gly Ser Thr Tyr Tyr Ala Thr Trp Ala Lys Gly
1               5                   10                  15

<210> SEQ ID NO 31
<211> LENGTH: 12
<212> TYPE: PRT
<213> ORGANISM: Artificial sequence
<220> FEATURE:
<223> OTHER INFORMATION: R166.C5 HCDR3

<400> SEQUENCE: 31

Asp Arg Ser Pro Asp Tyr Ser Ala Ala Phe Leu Leu
1               5                   10

<210> SEQ ID NO 32
<211> LENGTH: 9
<212> TYPE: PRT
<213> ORGANISM: Artificial sequence
<220> FEATURE:
<223> OTHER INFORMATION: R166.H9 HCDR3

<400> SEQUENCE: 32

Tyr Leu Ser Phe Thr Arg Leu Asp Leu
1               5

<210> SEQ ID NO 33
<211> LENGTH: 13
<212> TYPE: PRT
<213> ORGANISM: Artificial sequence
<220> FEATURE:
<223> OTHER INFORMATION: R166.F2 HCDR3

<400> SEQUENCE: 33

Gly Gly Tyr Val Gly Gly Gly Val Asp Ala Phe Asp Pro
1               5                   10

<210> SEQ ID NO 34
<211> LENGTH: 12
<212> TYPE: PRT
<213> ORGANISM: Artificial sequence
<220> FEATURE:
<223> OTHER INFORMATION: R166.H8 HCDR3

<400> SEQUENCE: 34

Asp Arg Ser Pro Asp Tyr Ser Ala Ala Phe Asn Leu
1               5                   10

<210> SEQ ID NO 35
<211> LENGTH: 12
<212> TYPE: PRT
<213> ORGANISM: Artificial sequence
<220> FEATURE:
<223> OTHER INFORMATION: R166.E7 HCDR3

<400> SEQUENCE: 35

Asp Arg Ser Pro Asp Tyr Ser Ala Ala Phe Asn Leu
1               5                   10

<210> SEQ ID NO 36
<211> LENGTH: 14
<212> TYPE: PRT
<213> ORGANISM: Artificial sequence
<220> FEATURE:
<223> OTHER INFORMATION: R166.G8 HCDR3

<400> SEQUENCE: 36
```

-continued

```
Asp Arg Asp Ala Ala Asp Thr Ser Asp Trp Ser Leu Asn Phe
1               5                   10

<210> SEQ ID NO 37
<211> LENGTH: 12
<212> TYPE: PRT
<213> ORGANISM: Artificial sequence
<220> FEATURE:
<223> OTHER INFORMATION: R166.F9 HCDR3

<400> SEQUENCE: 37

Tyr Gly Thr Asp Ser Asp Phe Tyr Tyr Leu Asp Leu
1               5                   10

<210> SEQ ID NO 38
<211> LENGTH: 12
<212> TYPE: PRT
<213> ORGANISM: Artificial sequence
<220> FEATURE:
<223> OTHER INFORMATION: R166.G2 HCDR3

<400> SEQUENCE: 38

Tyr Gly Thr Asp Ser Asp Phe Tyr Phe Leu Asp Leu
1               5                   10

<210> SEQ ID NO 39
<211> LENGTH: 15
<212> TYPE: PRT
<213> ORGANISM: Artificial sequence
<220> FEATURE:
<223> OTHER INFORMATION: R166.D1 HCDR3

<400> SEQUENCE: 39

Lys Pro Ile Leu Tyr Val Asp Ser Ser Gly Trp Tyr Ile Asp Leu
1               5                   10                  15

<210> SEQ ID NO 40
<211> LENGTH: 13
<212> TYPE: PRT
<213> ORGANISM: Artificial sequence
<220> FEATURE:
<223> OTHER INFORMATION: R166.G10 HCDR3

<400> SEQUENCE: 40

Tyr Gly Gly Asn Ser Gly Gly Tyr Asp Ser Phe Asn Leu
1               5                   10

<210> SEQ ID NO 41
<211> LENGTH: 17
<212> TYPE: PRT
<213> ORGANISM: Artificial sequence
<220> FEATURE:
<223> OTHER INFORMATION: R166.G3 HCDR3

<400> SEQUENCE: 41

Asp Asn Lys Ser Gly Gly Asn Asn Gly Tyr Pro Tyr Tyr Gly Leu Asp
1               5                   10                  15

Leu

<210> SEQ ID NO 42
<211> LENGTH: 8
<212> TYPE: PRT
<213> ORGANISM: Artificial sequence
<220> FEATURE:
<223> OTHER INFORMATION: R166.E5 HCDR3
```

```
<400> SEQUENCE: 42

Glu Gly Gly Trp Ala Phe Asp Leu
1               5

<210> SEQ ID NO 43
<211> LENGTH: 13
<212> TYPE: PRT
<213> ORGANISM: Artificial sequence
<220> FEATURE:
<223> OTHER INFORMATION: R166.E3 HCDR3

<400> SEQUENCE: 43

Ser Gln Glu Asp Asp Ser Phe Gly Tyr Gly Phe Asn Leu
1               5                   10

<210> SEQ ID NO 44
<211> LENGTH: 12
<212> TYPE: PRT
<213> ORGANISM: Artificial sequence
<220> FEATURE:
<223> OTHER INFORMATION: R166.A5 HCDR3

<400> SEQUENCE: 44

Gly Tyr Phe Gly Asn Thr Phe Trp Ala Met Asp Pro
1               5                   10

<210> SEQ ID NO 45
<211> LENGTH: 11
<212> TYPE: PRT
<213> ORGANISM: Artificial sequence
<220> FEATURE:
<223> OTHER INFORMATION: R166.H10 HCDR3

<400> SEQUENCE: 45

Gly Asn Pro His Tyr Ser Phe Gly Phe Asn Ile
1               5                   10

<210> SEQ ID NO 46
<211> LENGTH: 13
<212> TYPE: PRT
<213> ORGANISM: Artificial sequence
<220> FEATURE:
<223> OTHER INFORMATION: R166.C5 LCDR1

<400> SEQUENCE: 46

Gln Ala Ser Glu Ser Val Tyr Ser Asn Asn His Leu Ala
1               5                   10

<210> SEQ ID NO 47
<211> LENGTH: 13
<212> TYPE: PRT
<213> ORGANISM: Artificial sequence
<220> FEATURE:
<223> OTHER INFORMATION: R166.H9 LCDR1

<400> SEQUENCE: 47

Gln Ser Ser Gln Ser Val Tyr His Asn Asn Trp Leu Ala
1               5                   10

<210> SEQ ID NO 48
<211> LENGTH: 11
<212> TYPE: PRT
<213> ORGANISM: Artificial sequence
<220> FEATURE:
<223> OTHER INFORMATION: R166.F2 LCDR1

<400> SEQUENCE: 48
```

-continued

```
Gln Ala Ser Gln Ser Ile Tyr Thr Tyr Leu Ser
1               5                   10

<210> SEQ ID NO 49
<211> LENGTH: 13
<212> TYPE: PRT
<213> ORGANISM: Artificial sequence
<220> FEATURE:
<223> OTHER INFORMATION: R166.H8 LCDR1

<400> SEQUENCE: 49

Gln Ala Ser Glu Ser Val Tyr Ser Asn Asn His Leu Ala
1               5                   10

<210> SEQ ID NO 50
<211> LENGTH: 13
<212> TYPE: PRT
<213> ORGANISM: Artificial sequence
<220> FEATURE:
<223> OTHER INFORMATION: R166.E7 LCDR1

<400> SEQUENCE: 50

Gln Ala Ser Glu Ser Val Tyr Ser Asn Asn His Leu Ala
1               5                   10

<210> SEQ ID NO 51
<211> LENGTH: 13
<212> TYPE: PRT
<213> ORGANISM: Artificial sequence
<220> FEATURE:
<223> OTHER INFORMATION: R166.G8 LCDR1

<400> SEQUENCE: 51

Gln Ser Ser Asp Ser Val Asn Asn Asp Asn Trp Leu Ala
1               5                   10

<210> SEQ ID NO 52
<211> LENGTH: 11
<212> TYPE: PRT
<213> ORGANISM: Artificial sequence
<220> FEATURE:
<223> OTHER INFORMATION: R166.F9 LCDR1

<400> SEQUENCE: 52

Gln Ala Ser Gln Asn Ile Tyr Thr Tyr Leu Ser
1               5                   10

<210> SEQ ID NO 53
<211> LENGTH: 11
<212> TYPE: PRT
<213> ORGANISM: Artificial sequence
<220> FEATURE:
<223> OTHER INFORMATION: R166.G2 LCDR1

<400> SEQUENCE: 53

Gln Ala Ser Gln Ser Ile Tyr Ser Tyr Leu Ser
1               5                   10

<210> SEQ ID NO 54
<211> LENGTH: 11
<212> TYPE: PRT
<213> ORGANISM: Artificial sequence
<220> FEATURE:
<223> OTHER INFORMATION: R166.D1 LCDR1

<400> SEQUENCE: 54
```

```
Gln Ala Ser Glu Asn Ile Asn Asn Tyr Leu Ser
1               5                   10

<210> SEQ ID NO 55
<211> LENGTH: 11
<212> TYPE: PRT
<213> ORGANISM: Artificial sequence
<220> FEATURE:
<223> OTHER INFORMATION: R166.G10 LCDR1

<400> SEQUENCE: 55

Gln Ala Ser Gln Ser Ile Tyr Ser His Leu Ser
1               5                   10

<210> SEQ ID NO 56
<211> LENGTH: 11
<212> TYPE: PRT
<213> ORGANISM: Artificial sequence
<220> FEATURE:
<223> OTHER INFORMATION: R166.G3 LCDR1

<400> SEQUENCE: 56

Gln Ala Ser Gln Ser Ile Ser Ser His Leu Ala
1               5                   10

<210> SEQ ID NO 57
<211> LENGTH: 13
<212> TYPE: PRT
<213> ORGANISM: Artificial sequence
<220> FEATURE:
<223> OTHER INFORMATION: R166.E5 LCDR1

<400> SEQUENCE: 57

Gln Ser Ser Glu Ser Val Ala Asn Ser Asn Trp Leu Ser
1               5                   10

<210> SEQ ID NO 58
<211> LENGTH: 11
<212> TYPE: PRT
<213> ORGANISM: Artificial sequence
<220> FEATURE:
<223> OTHER INFORMATION: R166.E3 LCDR1

<400> SEQUENCE: 58

Gln Ala Ser Gln Ser Ile Gly Thr Tyr Leu Ser
1               5                   10

<210> SEQ ID NO 59
<211> LENGTH: 11
<212> TYPE: PRT
<213> ORGANISM: Artificial sequence
<220> FEATURE:
<223> OTHER INFORMATION: R166.A5 LCDR1

<400> SEQUENCE: 59

Gln Ala Ser Gln Ser Ile Ser Thr Tyr Leu Ser
1               5                   10

<210> SEQ ID NO 60
<211> LENGTH: 11
<212> TYPE: PRT
<213> ORGANISM: Artificial sequence
<220> FEATURE:
<223> OTHER INFORMATION: R166.H10 LCDR1

<400> SEQUENCE: 60

Gln Ala Ser Glu Ser Ile Tyr Ser Trp Leu Ser
```

```
1               5                    10
```

<210> SEQ ID NO 61
<211> LENGTH: 7
<212> TYPE: PRT
<213> ORGANISM: Artificial sequence
<220> FEATURE:
<223> OTHER INFORMATION: R166.C5 LCDR2

<400> SEQUENCE: 61

Ser Ala Ser Thr Leu Glu Ser
1               5

<210> SEQ ID NO 62
<211> LENGTH: 7
<212> TYPE: PRT
<213> ORGANISM: Artificial sequence
<220> FEATURE:
<223> OTHER INFORMATION: R166.H9 LCDR2

<400> SEQUENCE: 62

Gly Ala Ala Thr Leu Ala Ser
1               5

<210> SEQ ID NO 63
<211> LENGTH: 7
<212> TYPE: PRT
<213> ORGANISM: Artificial sequence
<220> FEATURE:
<223> OTHER INFORMATION: R166.F2 LCDR2

<400> SEQUENCE: 63

Arg Ala Ser Thr Leu Ala Ser
1               5

<210> SEQ ID NO 64
<211> LENGTH: 7
<212> TYPE: PRT
<213> ORGANISM: Artificial sequence
<220> FEATURE:
<223> OTHER INFORMATION: R166.H8 LCDR2

<400> SEQUENCE: 64

Ser Ala Ser Thr Leu Glu Ser
1               5

<210> SEQ ID NO 65
<211> LENGTH: 7
<212> TYPE: PRT
<213> ORGANISM: Artificial sequence
<220> FEATURE:
<223> OTHER INFORMATION: R166.E7 LCDR2

<400> SEQUENCE: 65

Ser Ala Ser Thr Leu Glu Ser
1               5

<210> SEQ ID NO 66
<211> LENGTH: 7
<212> TYPE: PRT
<213> ORGANISM: Artificial sequence
<220> FEATURE:
<223> OTHER INFORMATION: R166.G8 LCDR2

<400> SEQUENCE: 66

Gln Ala Ser Lys Leu Ala Ser
1               5

```
<210> SEQ ID NO 67
<211> LENGTH: 7
<212> TYPE: PRT
<213> ORGANISM: Artificial sequence
<220> FEATURE:
<223> OTHER INFORMATION: R166.F9 LCDR2

<400> SEQUENCE: 67

Lys Ala Ser Thr Leu Ala Ser
1               5

<210> SEQ ID NO 68
<211> LENGTH: 7
<212> TYPE: PRT
<213> ORGANISM: Artificial sequence
<220> FEATURE:
<223> OTHER INFORMATION: R166.G2 LCDR2

<400> SEQUENCE: 68

Lys Ala Ser Lys Leu Val Ser
1               5

<210> SEQ ID NO 69
<211> LENGTH: 7
<212> TYPE: PRT
<213> ORGANISM: Artificial sequence
<220> FEATURE:
<223> OTHER INFORMATION: R166.D1 LCDR2

<400> SEQUENCE: 69

Gln Ala Ser Arg Leu Ala Ser
1               5

<210> SEQ ID NO 70
<211> LENGTH: 7
<212> TYPE: PRT
<213> ORGANISM: Artificial sequence
<220> FEATURE:
<223> OTHER INFORMATION: R166.G10 LCDR2

<400> SEQUENCE: 70

Gly Ala Ser Thr Leu Ala Ser
1               5

<210> SEQ ID NO 71
<211> LENGTH: 7
<212> TYPE: PRT
<213> ORGANISM: Artificial sequence
<220> FEATURE:
<223> OTHER INFORMATION: R166.G3 LCDR2

<400> SEQUENCE: 71

Tyr Ala Ser Thr Leu Ala Ser
1               5

<210> SEQ ID NO 72
<211> LENGTH: 7
<212> TYPE: PRT
<213> ORGANISM: Artificial sequence
<220> FEATURE:
<223> OTHER INFORMATION: R166.E5 LCDR2

<400> SEQUENCE: 72

Trp Ala Ser Lys Leu Ala Ser
1               5
```

```
<210> SEQ ID NO 73
<211> LENGTH: 7
<212> TYPE: PRT
<213> ORGANISM: Artificial sequence
<220> FEATURE:
<223> OTHER INFORMATION: R166.E3 LCDR2

<400> SEQUENCE: 73

Arg Ala Ser Thr Leu Thr Ser
1               5

<210> SEQ ID NO 74
<211> LENGTH: 7
<212> TYPE: PRT
<213> ORGANISM: Artificial sequence
<220> FEATURE:
<223> OTHER INFORMATION: R166.A5 LCDR2

<400> SEQUENCE: 74

Gln Ala Ser Glu Leu Ala Tyr
1               5

<210> SEQ ID NO 75
<211> LENGTH: 7
<212> TYPE: PRT
<213> ORGANISM: Artificial sequence
<220> FEATURE:
<223> OTHER INFORMATION: R166.H10 LCDR2

<400> SEQUENCE: 75

Ser Ala Ser Tyr Leu Ala Ser
1               5

<210> SEQ ID NO 76
<211> LENGTH: 12
<212> TYPE: PRT
<213> ORGANISM: Artificial sequence
<220> FEATURE:
<223> OTHER INFORMATION: R166.C5 LCDR3

<400> SEQUENCE: 76

Ala Gly Tyr Lys Ser Ser Asp Thr Asp Gly Thr Ser
1               5                   10

<210> SEQ ID NO 77
<211> LENGTH: 11
<212> TYPE: PRT
<213> ORGANISM: Artificial sequence
<220> FEATURE:
<223> OTHER INFORMATION: R166.H9 LCDR3

<400> SEQUENCE: 77

Ala Gly Val Tyr Asn Asp Asp Ser Glu Asn Ala
1               5                   10

<210> SEQ ID NO 78
<211> LENGTH: 12
<212> TYPE: PRT
<213> ORGANISM: Artificial sequence
<220> FEATURE:
<223> OTHER INFORMATION: R166.F2 LCDR3

<400> SEQUENCE: 78

Gln Gln Gly Ala Leu Ser Ser Asn Ile His Asn Thr
1               5                   10
```

```
<210> SEQ ID NO 79
<211> LENGTH: 12
<212> TYPE: PRT
<213> ORGANISM: Artificial sequence
<220> FEATURE:
<223> OTHER INFORMATION: R166.H8 LCDR3

<400> SEQUENCE: 79

Ala Gly Tyr Lys Ser Ser Asp Thr Asp Gly Thr Ser
1               5                   10

<210> SEQ ID NO 80
<211> LENGTH: 12
<212> TYPE: PRT
<213> ORGANISM: Artificial sequence
<220> FEATURE:
<223> OTHER INFORMATION: R166.E7 LCDR3

<400> SEQUENCE: 80

Ala Gly Tyr Lys Ser Ser Asp Thr Asp Gly Thr Ser
1               5                   10

<210> SEQ ID NO 81
<211> LENGTH: 12
<212> TYPE: PRT
<213> ORGANISM: Artificial sequence
<220> FEATURE:
<223> OTHER INFORMATION: R166.G8 LCDR3

<400> SEQUENCE: 81

Gln Gly Thr Gly Tyr Ser Ser Thr Trp Tyr Val Ala
1               5                   10

<210> SEQ ID NO 82
<211> LENGTH: 12
<212> TYPE: PRT
<213> ORGANISM: Artificial sequence
<220> FEATURE:
<223> OTHER INFORMATION: R166.F9 LCDR3

<400> SEQUENCE: 82

Gln Ser Asp Trp Leu Ile Ser Ser Asn Gly Asn Thr
1               5                   10

<210> SEQ ID NO 83
<211> LENGTH: 12
<212> TYPE: PRT
<213> ORGANISM: Artificial sequence
<220> FEATURE:
<223> OTHER INFORMATION: R166.G2 LCDR3

<400> SEQUENCE: 83

Gln Ser Asp Trp Leu Ile Ser Ser Asn Gly Asn Thr
1               5                   10

<210> SEQ ID NO 84
<211> LENGTH: 13
<212> TYPE: PRT
<213> ORGANISM: Artificial sequence
<220> FEATURE:
<223> OTHER INFORMATION: R166.D1 LCDR3

<400> SEQUENCE: 84

Gln Gln Gly His Ser Val Ser Asn Asp Val Gly Asn Val
1               5                   10

<210> SEQ ID NO 85
```

-continued

<211> LENGTH: 12
<212> TYPE: PRT
<213> ORGANISM: Artificial sequence
<220> FEATURE:
<223> OTHER INFORMATION: R166.G10 LCDR3

<400> SEQUENCE: 85

Gln Cys Thr Ala Gly Thr Ser Ile Tyr Gly Asn Ala
1               5                   10

<210> SEQ ID NO 86
<211> LENGTH: 12
<212> TYPE: PRT
<213> ORGANISM: Artificial sequence
<220> FEATURE:
<223> OTHER INFORMATION: R166.G3 LCDR3

<400> SEQUENCE: 86

His Gln Ser Tyr Ser Gly Ser Asp Val Asp Asn Thr
1               5                   10

<210> SEQ ID NO 87
<211> LENGTH: 10
<212> TYPE: PRT
<213> ORGANISM: Artificial sequence
<220> FEATURE:
<223> OTHER INFORMATION: R166.E5 LCDR3

<400> SEQUENCE: 87

Gln Gly Gly Tyr Thr Ser Asp Arg Arg Ala
1               5                   10

<210> SEQ ID NO 88
<211> LENGTH: 12
<212> TYPE: PRT
<213> ORGANISM: Artificial sequence
<220> FEATURE:
<223> OTHER INFORMATION: R166.E3 LCDR3

<400> SEQUENCE: 88

Gln Glu Gly Tyr Ser Asp Ile Asn Val Asn Asn Ile
1               5                   10

<210> SEQ ID NO 89
<211> LENGTH: 12
<212> TYPE: PRT
<213> ORGANISM: Artificial sequence
<220> FEATURE:
<223> OTHER INFORMATION: R166.A5 LCDR3

<400> SEQUENCE: 89

Gln Gln Gly Tyr Ser Asp Ile Asn Val Asp Asn Phe
1               5                   10

<210> SEQ ID NO 90
<211> LENGTH: 13
<212> TYPE: PRT
<213> ORGANISM: Artificial sequence
<220> FEATURE:
<223> OTHER INFORMATION: R166.H10 LCDR3

<400> SEQUENCE: 90

Gln Tyr Asn Tyr Asp Ser Gly Asp Gly Ile Thr Asn Gly
1               5                   10

<210> SEQ ID NO 91
<211> LENGTH: 117

-continued

```
<212> TYPE: PRT
<213> ORGANISM: Artificial sequence
<220> FEATURE:
<223> OTHER INFORMATION: R166.C5 HCVR

<400> SEQUENCE: 91

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Arg Asn Phe Ala
            20                  25                  30

Met Ser Trp Val Arg Gln Ala Pro Gly Lys Gly Leu Glu Trp Ile Gly
        35                  40                  45

Ile Ile Tyr Ser Gly Gly Thr Arg Asp Tyr Ala Thr Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Asp Arg
                85                  90                  95

Ser Pro Asp Tyr Ser Ala Ala Phe Leu Leu Trp Gly Gln Gly Thr Leu
            100                 105                 110

Val Thr Val Ser Ser
        115

<210> SEQ ID NO 92
<211> LENGTH: 115
<212> TYPE: PRT
<213> ORGANISM: Artificial sequence
<220> FEATURE:
<223> OTHER INFORMATION: R166.H9 HCVR

<400> SEQUENCE: 92

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn Asn Tyr Asn
            20                  25                  30

Met Ile Trp Val Arg Gln Ala Pro Gly Glu Gly Leu Glu Trp Ile Gly
        35                  40                  45

Met Ile Gly Asp Gly Asp Asp Ala Ala Trp Tyr Ala Ser Trp Ala Lys
    50                  55                  60

Gly Arg Phe Thr Ile Ser Lys Thr Ser Thr Thr Val Asp Leu Glu Val
65                  70                  75                  80

Thr Ser Leu Thr Thr Glu Asp Thr Ala Ile Tyr Phe Cys Ala Arg Tyr
                85                  90                  95

Leu Ser Phe Thr Arg Leu Asp Leu Trp Gly Gln Gly Thr Leu Val Thr
            100                 105                 110

Val Ser Ser
        115

<210> SEQ ID NO 93
<211> LENGTH: 121
<212> TYPE: PRT
<213> ORGANISM: Artificial sequence
<220> FEATURE:
<223> OTHER INFORMATION: R166.F2 HCVR

<400> SEQUENCE: 93

Gln Ser Val Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser His Asp
```

-continued

```
                20                  25                  30

Met Ser Trp Val Arg Gln Ala Pro Gly Lys Gly Leu Glu Trp Ile Gly
            35                  40                  45

Tyr Ile Tyr Tyr Gly Ser Gly Ser Thr Asp Tyr Ala Ser Trp Ala Glu
    50                  55                  60

Gly Arg Phe Thr Ile Thr Arg Asn Thr Asn Glu Asn Thr Val Thr Leu
65                  70                  75                  80

Lys Met Thr Ser Leu Thr Thr Glu Asp Thr Ala Thr Tyr Phe Cys Ala
                85                  90                  95

Arg Gly Gly Tyr Val Gly Gly Gly Val Asp Ala Phe Asp Pro Trp Gly
                100                 105                 110

Pro Gly Thr Val Val Thr Val Ser Ser
            115                 120

<210> SEQ ID NO 94
<211> LENGTH: 118
<212> TYPE: PRT
<213> ORGANISM: Artificial sequence
<220> FEATURE:
<223> OTHER INFORMATION: R166.H8 HCVR

<400> SEQUENCE: 94

Gln Ser Val Glu Glu Ser Gly Gly Arg Leu Val Thr Pro Gly Thr Pro
1                   5                   10                  15

Leu Thr Leu Thr Cys Thr Val Ser Gly Phe Ser Leu Ser Ser Phe Ala
                20                  25                  30

Met Ser Trp Val Arg Gln Ala Pro Gly Lys Gly Leu Glu Trp Ile Gly
            35                  40                  45

Ile Ile Tyr Ala Thr Gly Gly Thr Arg Asp Tyr Ala Thr Trp Ala Ala
    50                  55                  60

Gly Arg Phe Thr Ile Ser Lys Thr Ser Thr Thr Val Gly Leu Lys Met
65                  70                  75                  80

Thr Ser Pro Thr Thr Glu Asp Thr Ala Thr Tyr Phe Cys Ala Arg Asp
                85                  90                  95

Arg Ser Pro Asp Tyr Ser Ala Ala Phe Asn Leu Trp Gly Gln Gly Thr
                100                 105                 110

Leu Val Thr Val Ser Ser
            115

<210> SEQ ID NO 95
<211> LENGTH: 117
<212> TYPE: PRT
<213> ORGANISM: Artificial sequence
<220> FEATURE:
<223> OTHER INFORMATION: R166.E7 HCVR

<400> SEQUENCE: 95

Gln Ser Val Glu Glu Ser Gly Gly Arg Leu Val Thr Pro Gly Thr Pro
1                   5                   10                  15

Leu Thr Leu Thr Cys Thr Val Ser Gly Phe Ser Leu Ser Ser Phe Ala
                20                  25                  30

Met Ser Trp Val Arg Gln Ala Pro Gly Lys Gly Leu Glu Trp Ile Gly
            35                  40                  45

Ile Ile Tyr Thr Gly Gly Thr Arg Asp Tyr Ala Thr Trp Ala Lys Gly
    50                  55                  60

Arg Phe Thr Ile Ser Lys Thr Ser Thr Thr Val Asp Leu Lys Met Thr
65                  70                  75                  80
```

-continued

```
Ser Pro Thr Thr Glu Asp Thr Ala Thr Tyr Phe Cys Ala Arg Asp Arg
            85              90                  95

Ser Pro Asp Tyr Ser Ala Ala Phe Asn Leu Trp Gly Gln Gly Thr Leu
            100             105                 110

Val Thr Val Ser Ser
        115

<210> SEQ ID NO 96
<211> LENGTH: 128
<212> TYPE: PRT
<213> ORGANISM: Artificial sequence
<220> FEATURE:
<223> OTHER INFORMATION: R166.G8 HCVR

<400> SEQUENCE: 96

Gln Leu Leu Glu Gln Ser Gly Gly Gly Ala Glu Gly Gly Leu Val Lys
1               5               10                  15

Pro Gly Gly Ser Leu Glu Leu Cys Cys Lys Ala Ser Gly Phe Ser Leu
            20              25                  30

Ser Asn Ile Tyr Trp Ile Cys Trp Val Arg Gln Ala Pro Gly Thr Gly
        35              40                  45

Leu Glu Trp Ile Gly Cys Ile Asn Ser Gly Ser Asn Ser Tyr Thr Tyr
    50              55                  60

Tyr Ala Asn Trp Val Asp Gly Arg Phe Thr Leu Ser Arg Asp Ile Asp
65              70                  75                  80

Gln Ser Thr Gly Cys Leu Gln Leu Asn Ser Leu Thr Ala Ala Asp Thr
            85              90                  95

Ala Met Tyr Tyr Cys Ala Arg Asp Arg Asp Ala Ala Asp Thr Ser Asp
            100             105                 110

Trp Ser Leu Asn Phe Trp Gly Gln Gly Thr Leu Val Thr Val Ser Ser
        115             120                 125

<210> SEQ ID NO 97
<211> LENGTH: 117
<212> TYPE: PRT
<213> ORGANISM: Artificial sequence
<220> FEATURE:
<223> OTHER INFORMATION: R166.F9 HCVR

<400> SEQUENCE: 97

Gln Ser Leu Glu Glu Ser Gly Gly Arg Leu Val Lys Pro Asp Glu Thr
1               5               10                  15

Leu Thr Ile Thr Cys Thr Val Ser Gly Ile Asp Leu Ser Ser Asn Ala
            20              25                  30

Met Gly Trp Val Arg Gln Ala Pro Gly Lys Gly Leu Glu Trp Ile Gly
        35              40                  45

Leu Ile Asn Ile Tyr Asp Asn Thr Tyr Tyr Ala Ser Trp Ala Lys Gly
    50              55                  60

Arg Phe Thr Ile Ser Lys Thr Ser Thr Thr Val Asp Leu Lys Val Thr
65              70                  75                  80

Ser Leu Thr Thr Glu Asp Thr Ala Thr Tyr Phe Cys Ala Arg Tyr Gly
            85              90                  95

Thr Asp Ser Asp Phe Tyr Tyr Leu Asp Leu Trp Gly Gln Gly Thr Leu
            100             105                 110

Val Thr Val Ser Ser
        115

<210> SEQ ID NO 98
```

<211> LENGTH: 117
<212> TYPE: PRT
<213> ORGANISM: Artificial sequence
<220> FEATURE:
<223> OTHER INFORMATION: R166.G2 HCVR

<400> SEQUENCE: 98

Gln Ser Leu Glu Glu Ser Gly Gly Arg Leu Val Lys Pro Asp Glu Thr
1               5                   10                  15

Leu Thr Ile Thr Cys Thr Val Ser Gly Ile Asp Leu Ser Ser Asp Ala
            20                  25                  30

Met Ser Trp Val Arg Gln Ala Pro Gly Lys Gly Leu Glu Trp Ile Gly
        35                  40                  45

Leu Ile Asn Arg Tyr Gly Asn Thr Tyr Tyr Ala Ser Trp Ala Lys Gly
    50                  55                  60

Arg Phe Thr Ile Ser Lys Thr Ser Thr Thr Val Asp Leu Lys Val Thr
65                  70                  75                  80

Ser Leu Thr Thr Glu Asp Thr Ala Thr Tyr Phe Cys Ala Arg Tyr Gly
                85                  90                  95

Thr Asp Ser Asp Phe Tyr Phe Leu Asp Leu Trp Gly Gln Gly Thr Leu
            100                 105                 110

Val Thr Val Ser Ser
        115

<210> SEQ ID NO 99
<211> LENGTH: 120
<212> TYPE: PRT
<213> ORGANISM: Artificial sequence
<220> FEATURE:
<223> OTHER INFORMATION: R166.D1 HCVR

<400> SEQUENCE: 99

Gln Ser Val Glu Glu Ser Gly Gly Arg Leu Val Lys Pro Asp Glu Ser
1               5                   10                  15

Leu Thr Leu Thr Cys Thr Val Ser Gly Phe Ser Leu Ser Asn Tyr Asp
            20                  25                  30

Met Ile Trp Val Arg Gln Ala Pro Gly Lys Gly Leu Glu Trp Ile Gly
        35                  40                  45

Val Ile Tyr Pro Thr Gly Thr Thr Tyr Tyr Ala Asn Trp Val Lys Gly
    50                  55                  60

Arg Phe Thr Ile Ser Lys Thr Ser Thr Thr Val Gly Leu Leu Ile Thr
65                  70                  75                  80

Ser Pro Thr Thr Glu Asp Thr Ala Thr Tyr Phe Cys Ala Arg Lys Pro
                85                  90                  95

Ile Leu Tyr Val Asp Ser Ser Gly Trp Tyr Ile Asp Leu Trp Gly Gln
            100                 105                 110

Gly Thr Leu Val Thr Val Ser Ser
        115                 120

<210> SEQ ID NO 100
<211> LENGTH: 118
<212> TYPE: PRT
<213> ORGANISM: Artificial sequence
<220> FEATURE:
<223> OTHER INFORMATION: R166.G10 HCVR

<400> SEQUENCE: 100

Gln Ser Val Glu Glu Ser Gly Gly Arg Leu Val Thr Pro Gly Thr Pro
1               5                   10                  15

-continued

```
Leu Thr Leu Thr Cys Thr Val Ser Gly Phe Ser Leu Ser Ser Ser Ala
            20                  25                  30

Val Ser Trp Val Arg Gln Ala Pro Gly Lys Gly Leu Glu Tyr Ile Gly
            35                  40                  45

Ile Ile Gly Ser Gly Gly Ser Thr Tyr Tyr Ala Ser Trp Val Asn Gly
            50                  55                  60

Arg Phe Thr Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Tyr Gly
                85                  90                  95

Gly Asn Ser Gly Gly Tyr Asp Ser Phe Asn Leu Trp Gly Gln Gly Thr
            100                 105                 110

Leu Val Thr Val Ser Ser
        115
```

```
<210> SEQ ID NO 101
<211> LENGTH: 123
<212> TYPE: PRT
<213> ORGANISM: Artificial sequence
<220> FEATURE:
<223> OTHER INFORMATION: R166.G3 HCVR

<400> SEQUENCE: 101

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Tyr Ala
            20                  25                  30

Met Gly Trp Val Arg Gln Ala Pro Gly Lys Gly Leu Glu Tyr Ile Gly
            35                  40                  45

Ile Ile Gly Tyr Gly Gly Asn Thr Asn Tyr Ala Asn Trp Ala Lys Gly
            50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Asn Lys Ser Gly Gly Asn Asn Gly Tyr Pro Tyr Tyr Gly Leu Asp Leu
            100                 105                 110

Trp Gly Pro Gly Thr Leu Val Thr Val Ser Ser
        115                 120
```

```
<210> SEQ ID NO 102
<211> LENGTH: 114
<212> TYPE: PRT
<213> ORGANISM: Artificial sequence
<220> FEATURE:
<223> OTHER INFORMATION: R166.E5 HCVR

<400> SEQUENCE: 102

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Tyr Tyr
            20                  25                  30

Met Ile Trp Val Arg Gln Ala Pro Gly Lys Gly Leu Glu Tyr Ile Gly
            35                  40                  45

Ile Val Thr Ser Ser Gly Ser Thr His Tyr Ala Ser Trp Ala Asn Gly
            50                  55                  60

Arg Phe Ala Ile Ser Lys Thr Ser Ser Thr Thr Val Asp Leu Lys Met
65                  70                  75                  80
```

-continued

```
Pro Ser Leu Thr Thr Glu Asp Thr Ala Thr Tyr Phe Cys Ala Arg Glu
                85                  90                  95

Gly Gly Trp Ala Phe Asp Leu Trp Gly Gln Gly Thr Leu Val Thr Val
            100                 105                 110

Ser Ser

<210> SEQ ID NO 103
<211> LENGTH: 119
<212> TYPE: PRT
<213> ORGANISM: Artificial sequence
<220> FEATURE:
<223> OTHER INFORMATION: R166.E3 HCVR

<400> SEQUENCE: 103

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Cys Val
                20                  25                  30

Leu Ile Trp Val Arg Gln Ala Pro Glu Lys Gly Leu Glu Trp Ile Gly
            35                  40                  45

Phe Ile Tyr Gly Ser Gly Asn Ala Tyr Tyr Ala Asn Trp Ala Lys Gly
        50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Gln Glu Asp Asp Ser Phe Gly Tyr Gly Phe Asn Leu Trp Gly Gln Gly
            100                 105                 110

Thr Leu Val Thr Val Ser Ser
        115

<210> SEQ ID NO 104
<211> LENGTH: 117
<212> TYPE: PRT
<213> ORGANISM: Artificial sequence
<220> FEATURE:
<223> OTHER INFORMATION: R166.A5 HCVR

<400> SEQUENCE: 104

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Thr
                20                  25                  30

Val Ile Trp Val Arg Gln Ala Pro Gly Lys Gly Leu Glu Trp Ile Gly
            35                  40                  45

Ile Ile Phe Gly Ser Gly Gly Thr Tyr Tyr Ala Thr Trp Ala Glu Gly
        50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Gly Tyr
                85                  90                  95

Phe Gly Asn Thr Phe Trp Ala Met Asp Pro Trp Gly Pro Gly Thr Leu
            100                 105                 110

Val Thr Val Ser Ser
        115

<210> SEQ ID NO 105
```

```
<211> LENGTH: 117
<212> TYPE: PRT
<213> ORGANISM: Artificial sequence
<220> FEATURE:
<223> OTHER INFORMATION: R166.H10 HCVR

<400> SEQUENCE: 105

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Ser Trp Val Arg Gln Ala Pro Gly Lys Gly Leu Glu Tyr Ile Gly
        35                  40                  45

Ile Ile Ser Gly Ser Gly Ser Thr Tyr Tyr Ala Thr Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Asn Pro His Tyr Ser Phe Gly Phe Asn Ile Trp Gly Pro Gly Thr Leu
            100                 105                 110

Val Thr Val Ser Leu
        115

<210> SEQ ID NO 106
<211> LENGTH: 111
<212> TYPE: PRT
<213> ORGANISM: Artificial sequence
<220> FEATURE:
<223> OTHER INFORMATION: R166.C5 LCVR

<400> SEQUENCE: 106

Ile Val Met Thr Gln Thr Pro Ser Ser Lys Ser Val Pro Val Gly Asp
1               5                   10                  15

Thr Val Thr Ile Asn Cys Gln Ala Ser Glu Ser Val Tyr Ser Asn Asn
            20                  25                  30

His Leu Ala Trp Phe Gln Gln Lys Pro Gly Gln Pro Pro Lys Leu Leu
        35                  40                  45

Ile Tyr Ser Ala Ser Thr Leu Glu Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Tyr Lys Ser Ser Asp
                85                  90                  95

Thr Asp Gly Thr Ser Phe Gly Gly Gly Thr Glu Val Val Val Lys
            100                 105                 110

<210> SEQ ID NO 107
<211> LENGTH: 110
<212> TYPE: PRT
<213> ORGANISM: Artificial sequence
<220> FEATURE:
<223> OTHER INFORMATION: R166.H9 LCVR

<400> SEQUENCE: 107

Ala Val Leu Thr Gln Thr Pro Ser Pro Val Ser Ala Ala Val Gly Gly
1               5                   10                  15

Thr Val Thr Ile Asn Cys Gln Ser Ser Gln Ser Val Tyr His Asn Asn
            20                  25                  30
```

-continued

```
Trp Leu Ala Trp Tyr Gln Gln Lys Pro Gly Gln Pro Pro Lys Leu Leu
        35                  40                  45

Ile Tyr Gly Ala Ala Thr Leu Ala Ser Gly Val Pro Ser Arg Phe Lys
    50                  55                  60

Gly Ser Gly Ser Gly Thr Gln Phe Thr Phe Thr Ile Thr Asp Val Gln
65                  70                  75                  80

Cys Asp Asp Val Gly Thr Tyr Tyr Cys Ala Gly Val Tyr Asn Asp Asp
                85                  90                  95

Ser Glu Asn Ala Phe Gly Gly Gly Thr Glu Val Val Val Lys
            100                 105                 110

<210> SEQ ID NO 108
<211> LENGTH: 110
<212> TYPE: PRT
<213> ORGANISM: Artificial sequence
<220> FEATURE:
<223> OTHER INFORMATION: R166.F2 LCVR

<400> SEQUENCE: 108

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Thr Tyr
                20                  25                  30

Leu Ser Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Asp Phe Thr Leu Thr Ile Ser Gly Ala Gln Cys
65                  70                  75                  80

Ala Asp Ala Ala Thr Tyr Tyr Cys Gln Gln Gly Ala Leu Ser Ser Asn
                85                  90                  95

Ile His Asn Thr Phe Gly Gly Gly Thr Glu Val Val Val Lys
            100                 105                 110

<210> SEQ ID NO 109
<211> LENGTH: 111
<212> TYPE: PRT
<213> ORGANISM: Artificial sequence
<220> FEATURE:
<223> OTHER INFORMATION: R166.H8 LCVR

<400> SEQUENCE: 109

Ile Val Met Thr Gln Thr Pro Ser Ser Lys Ser Val Pro Val Gly Asp
1               5                   10                  15

Thr Val Thr Ile Asn Cys Gln Ala Ser Glu Ser Val Tyr Ser Asn Asn
                20                  25                  30

His Leu Ala Trp Phe Gln Gln Lys Pro Gly Gln Pro Pro Lys Leu Leu
        35                  40                  45

Ile Tyr Ser Ala Ser Thr Leu Glu Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Tyr Lys Ser Ser Asp
                85                  90                  95

Thr Asp Gly Thr Ser Phe Gly Gly Gly Thr Glu Val Val Val Lys
            100                 105                 110

<210> SEQ ID NO 110
```

```
<211> LENGTH: 111
<212> TYPE: PRT
<213> ORGANISM: Artificial sequence
<220> FEATURE:
<223> OTHER INFORMATION: R166.E7 LCVR

<400> SEQUENCE: 110

Ile Val Met Thr Gln Thr Pro Ser Ser Lys Ser Val Pro Val Gly Asp
1               5                   10                  15

Thr Val Thr Ile Asn Cys Gln Ala Ser Glu Ser Val Tyr Ser Asn Asn
            20                  25                  30

His Leu Ala Trp Phe Gln Gln Lys Pro Gly Gln Pro Pro Lys Leu Leu
        35                  40                  45

Ile Tyr Ser Ala Ser Thr Leu Glu Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Tyr Lys Ser Ser Asp
                85                  90                  95

Thr Asp Gly Thr Ser Phe Gly Gly Gly Thr Glu Val Val Val Lys
            100                 105                 110

<210> SEQ ID NO 111
<211> LENGTH: 111
<212> TYPE: PRT
<213> ORGANISM: Artificial sequence
<220> FEATURE:
<223> OTHER INFORMATION: R166.G8 LCVR

<400> SEQUENCE: 111

Gln Val Leu Thr Gln Thr Pro Ser Ser Val Ser Ala Ala Val Gly Gly
1               5                   10                  15

Thr Val Thr Ile Ser Cys Gln Ser Ser Asp Ser Val Asn Asn Asp Asn
            20                  25                  30

Trp Leu Ala Trp Tyr Gln Gln Lys Pro Gly Gln Pro Pro Lys Leu Leu
        35                  40                  45

Ile Tyr Gln Ala Ser Lys Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Asn Tyr Tyr Cys Gln Gly Thr Gly Tyr Ser Ser
                85                  90                  95

Thr Trp Tyr Val Ala Phe Gly Gly Gly Thr Glu Val Val Val Lys
            100                 105                 110

<210> SEQ ID NO 112
<211> LENGTH: 116
<212> TYPE: PRT
<213> ORGANISM: Artificial sequence
<220> FEATURE:
<223> OTHER INFORMATION: R166.F9 LCVR

<400> SEQUENCE: 112

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Asn Ile Tyr Thr
            20                  25                  30

Tyr Leu Ser Trp Tyr Gln Gln Lys Pro Gly Gln Pro Pro Lys Leu Leu
        35                  40                  45
```

```
Ile Tyr Lys Ala Ser Thr Leu Ala Ser Gly Val Ser Ser Arg Phe Lys
    50                  55                  60

Gly Ser Gly Ser Gly Thr Glu Phe Thr Leu Thr Ile Asn Asp Leu Glu
65                  70                  75                  80

Cys Ala Asp Ala Ala Thr Tyr Tyr Cys Gln Ser Asp Trp Leu Ile Ser
                85                  90                  95

Ser Asn Gly Asn Thr Phe Gly Gly Gly Thr Glu Val Val Val Thr Gly
                100                 105                 110

Asp Pro Val Ala
        115

<210> SEQ ID NO 113
<211> LENGTH: 111
<212> TYPE: PRT
<213> ORGANISM: Artificial sequence
<220> FEATURE:
<223> OTHER INFORMATION: R166.G2 LCVR

<400> SEQUENCE: 113

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Ser Ile Tyr Ser
                20                  25                  30

Tyr Leu Ser Trp Tyr Gln Gln Lys Pro Gly Gln Arg Pro Lys Leu Leu
        35                  40                  45

Ile Tyr Lys Ala Ser Lys Leu Val Ser Gly Val Pro Ser Arg Phe Arg
    50                  55                  60

Gly Ser Gly Ser Gly Thr Glu Phe Thr Leu Thr Ile Ser Asp Leu Glu
65                  70                  75                  80

Cys Ala Asp Ala Ala Ser Tyr Tyr Cys Gln Ser Asp Trp Leu Ile Ser
                85                  90                  95

Ser Asn Gly Asn Thr Phe Gly Gly Gly Thr Glu Val Val Val Thr
                100                 105                 110

<210> SEQ ID NO 114
<211> LENGTH: 111
<212> TYPE: PRT
<213> ORGANISM: Artificial sequence
<220> FEATURE:
<223> OTHER INFORMATION: R166.D1 LCVR

<400> SEQUENCE: 114

Ala Tyr Asp Met Thr Gln Thr Pro Ser Ser Val Ser Ala Ala Val Gly
1               5                   10                  15

Gly Thr Val Ser Ile Lys Cys Gln Ala Ser Glu Asn Ile Asn Asn Tyr
                20                  25                  30

Leu Ser Trp Tyr Gln Gln Lys Pro Gly Gln Pro Pro Lys Leu Leu Ile
        35                  40                  45

Tyr Gln Ala Ser Arg Leu Ala Ser Ala Val Pro Ser Arg Phe Lys Gly
    50                  55                  60

Ser Gly Ser Gly Thr Gln Phe Thr Leu Thr Ile Asp Asp Leu Glu Cys
65                  70                  75                  80

Ala Asp Ala Ala Thr Tyr Tyr Cys Gln Gln Gly His Ser Val Ser Asn
                85                  90                  95

Asp Val Gly Asn Val Phe Gly Gly Gly Thr Glu Val Val Val Lys
                100                 105                 110

<210> SEQ ID NO 115
```

<211> LENGTH: 110
<212> TYPE: PRT
<213> ORGANISM: Artificial sequence
<220> FEATURE:
<223> OTHER INFORMATION: R166.G10 LCVR

<400> SEQUENCE: 115

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser His
            20                  25                  30

Leu Ser Trp Tyr Gln Gln Lys Pro Gly Gln Pro Pro Lys Leu Leu Ile
        35                  40                  45

His Gly Ala Ser Thr Leu Ala Ser Gly Ala Ser Ser Arg Phe Lys Ala
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Ala Gly Thr Ser Ile
                85                  90                  95

Tyr Gly Asn Ala Phe Gly Gly Gly Thr Glu Val Val Val Arg
            100                 105                 110

<210> SEQ ID NO 116
<211> LENGTH: 110
<212> TYPE: PRT
<213> ORGANISM: Artificial sequence
<220> FEATURE:
<223> OTHER INFORMATION: R166.G3 LCVR

<400> SEQUENCE: 116

Ala Tyr Asp Met Thr Gln Thr Pro Ala Ser Val Glu Val Pro Val Gly
1               5                   10                  15

Gly Thr Val Thr Ile Asn Cys Gln Ala Ser Gln Ser Ile Ser Ser His
            20                  25                  30

Leu Ala Trp Tyr Gln Gln Lys Arg Gly Gln Pro Pro Lys Val Leu Ile
        35                  40                  45

Tyr Tyr Ala Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Glu Cys
65                  70                  75                  80

Ala Asp Ala Ala Thr Tyr Phe Cys His Gln Ser Tyr Ser Gly Ser Asp
                85                  90                  95

Val Asp Asn Thr Phe Gly Gly Gly Thr Glu Val Val Val Arg
            100                 105                 110

<210> SEQ ID NO 117
<211> LENGTH: 109
<212> TYPE: PRT
<213> ORGANISM: Artificial sequence
<220> FEATURE:
<223> OTHER INFORMATION: R166.E5 LCVR

<400> SEQUENCE: 117

Gln Val Leu Thr Gln Thr Pro Phe Ser Val Ser Thr Ala Val Gly Gly
1               5                   10                  15

Thr Val Thr Ile Asn Cys Gln Ser Ser Glu Ser Val Ala Asn Ser Asn
            20                  25                  30

Trp Leu Ser Trp Tyr Gln Gln Lys Pro Gly Gln Pro Pro Lys Leu Leu
        35                  40                  45

```
Ile Tyr Trp Ala Ser Lys Leu Ala Ser Gly Val Pro Ser Arg Phe Ser
    50              55              60

Gly Ser Gly Ser Gly Thr Gln Phe Thr Leu Thr Ile Ser Gly Val Gln
65              70              75              80

Cys Ala Asp Ala Ala Thr Tyr Tyr Cys Gln Gly Gly Tyr Thr Ser Asp
                85              90              95

Arg Arg Ala Phe Gly Gly Gly Thr Glu Val Val Val Lys
            100             105
```

<210> SEQ ID NO 118
<211> LENGTH: 110
<212> TYPE: PRT
<213> ORGANISM: Artificial sequence
<220> FEATURE:
<223> OTHER INFORMATION: R166.E3 LCVR

<400> SEQUENCE: 118

```
Ala Tyr Asp Met Thr Gln Thr Pro Ala Ser Val Glu Val Ala Val Gly
1               5               10              15

Gly Thr Val Thr Ile Asn Cys Gln Ala Ser Gln Ser Ile Gly Thr Tyr
            20              25              30

Leu Ser Trp Tyr Gln Gln Lys Pro Gly Gln Pro Pro Lys Leu Leu Ile
        35              40              45

Tyr Arg Ala Ser Thr Leu Thr Ser Gly Val Ser Ser Arg Phe Lys Gly
    50              55              60

Ser Gly Ser Gly Thr Gln Phe Thr Leu Thr Ile Ser Gly Val Glu Cys
65              70              75              80

Ala Asp Ala Ala Thr Tyr Tyr Cys Gln Glu Gly Tyr Ser Asp Ile Asn
                85              90              95

Val Asn Asn Ile Phe Gly Gly Gly Thr Glu Val Val Val Lys
            100             105             110
```

<210> SEQ ID NO 119
<211> LENGTH: 111
<212> TYPE: PRT
<213> ORGANISM: Artificial sequence
<220> FEATURE:
<223> OTHER INFORMATION: R166.A5 LCVR

<400> SEQUENCE: 119

```
Ala Asn Ile Val Met Thr Gln Thr Pro Ala Ser Val Ser Gly Ala Val
1               5               10              15

Gly Gly Thr Val Thr Ile Lys Cys Gln Ala Ser Gln Ser Ile Ser Thr
            20              25              30

Tyr Leu Ser Trp Tyr Gln Gln Lys Pro Gly Gln Pro Pro Lys Leu Leu
        35              40              45

Ile Tyr Gln Ala Ser Glu Leu Ala Tyr Gly Val Ser Ser Arg Phe Lys
    50              55              60

Gly Ser Gly Ser Gly Thr Glu Phe Thr Leu Thr Ile Ser Gly Val Glu
65              70              75              80

Cys Ala Asp Ala Ala Thr Tyr Tyr Cys Gln Gln Gly Tyr Ser Asp Ile
                85              90              95

Asn Val Asp Asn Phe Phe Gly Gly Gly Thr Glu Val Val Val Lys
            100             105             110
```

<210> SEQ ID NO 120
<211> LENGTH: 112
<212> TYPE: PRT
<213> ORGANISM: Artificial sequence

```
<220> FEATURE:
<223> OTHER INFORMATION: R166.H10 LCVR

<400> SEQUENCE: 120

Ala Asp Ile Val Met Thr Gln Thr Pro Ala Ser Val Ser Glu Pro Val
1               5                   10                  15

Gly Gly Thr Val Thr Ile Asn Cys Gln Ala Ser Glu Ser Ile Tyr Ser
            20                  25                  30

Trp Leu Ser Trp Tyr Gln Gln Lys Pro Gly Gln Pro Pro Lys Leu Leu
        35                  40                  45

Ile Tyr Ser Ala Ser Tyr Leu Ala Ser Gly Val Pro Ser Gln Phe Arg
    50                  55                  60

Gly Ser Gly Ser Gly Thr Glu Tyr Thr Leu Thr Ile Ser Asp Leu Glu
65                  70                  75                  80

Cys Ala Asp Ala Ala Thr Tyr Tyr Cys Gln Tyr Asn Tyr Asp Ser Gly
                85                  90                  95

Asp Gly Ile Thr Asn Gly Phe Gly Gly Gly Thr Glu Val Val Val Lys
            100                 105                 110

<210> SEQ ID NO 121
<211> LENGTH: 15
<212> TYPE: DNA
<213> ORGANISM: Artificial sequence
<220> FEATURE:
<223> OTHER INFORMATION: R166.C5 HCDR1

<400> SEQUENCE: 121
aactttgcaa tgagc                                                    15

<210> SEQ ID NO 122
<211> LENGTH: 15
<212> TYPE: DNA
<213> ORGANISM: Artificial sequence
<220> FEATURE:
<223> OTHER INFORMATION: R166.H9 HCDR1

<400> SEQUENCE: 122
aactacaaca tgatc                                                    15

<210> SEQ ID NO 123
<211> LENGTH: 15
<212> TYPE: DNA
<213> ORGANISM: Artificial sequence
<220> FEATURE:
<223> OTHER INFORMATION: R166.F2 HCDR1

<400> SEQUENCE: 123
agccacgaca tgagt                                                    15

<210> SEQ ID NO 124
<211> LENGTH: 15
<212> TYPE: DNA
<213> ORGANISM: Artificial sequence
<220> FEATURE:
<223> OTHER INFORMATION: R166.H8 HCDR1

<400> SEQUENCE: 124
agctttgcaa tgagc                                                    15

<210> SEQ ID NO 125
<211> LENGTH: 15
<212> TYPE: DNA
<213> ORGANISM: Artificial sequence
```

```
<220> FEATURE:
<223> OTHER INFORMATION: R166.E7 HCDR1

<400> SEQUENCE: 125
agctttgcaa tgagc                                                          15

<210> SEQ ID NO 126
<211> LENGTH: 18
<212> TYPE: DNA
<213> ORGANISM: Artificial sequence
<220> FEATURE:
<223> OTHER INFORMATION: R166.G8 HCDR1

<400> SEQUENCE: 126
aatatctact ggatatgt                                                       18

<210> SEQ ID NO 127
<211> LENGTH: 15
<212> TYPE: DNA
<213> ORGANISM: Artificial sequence
<220> FEATURE:
<223> OTHER INFORMATION: R166.F9 HCDR1

<400> SEQUENCE: 127
agcaatgcaa tgggc                                                          15

<210> SEQ ID NO 128
<211> LENGTH: 15
<212> TYPE: DNA
<213> ORGANISM: Artificial sequence
<220> FEATURE:
<223> OTHER INFORMATION: R166.G2 HCDR1

<400> SEQUENCE: 128
agcgatgcga tgagc                                                          15

<210> SEQ ID NO 129
<211> LENGTH: 15
<212> TYPE: DNA
<213> ORGANISM: Artificial sequence
<220> FEATURE:
<223> OTHER INFORMATION: R166.D1 HCDR1

<400> SEQUENCE: 129
aactacgaca tgatc                                                          15

<210> SEQ ID NO 130
<211> LENGTH: 15
<212> TYPE: DNA
<213> ORGANISM: Artificial sequence
<220> FEATURE:
<223> OTHER INFORMATION: R166.G10 HCDR1

<400> SEQUENCE: 130
agctctgcag tgagc                                                          15

<210> SEQ ID NO 131
<211> LENGTH: 15
<212> TYPE: DNA
<213> ORGANISM: Artificial sequence
<220> FEATURE:
<223> OTHER INFORMATION: R166.G3 HCDR1

<400> SEQUENCE: 131
agatatgcaa tgggc                                                          15
```

-continued

```
<210> SEQ ID NO 132
<211> LENGTH: 15
<212> TYPE: DNA
<213> ORGANISM: Artificial sequence
<220> FEATURE:
<223> OTHER INFORMATION: R166.E5 HCDR1

<400> SEQUENCE: 132
ggctactaca tgatc                                                    15

<210> SEQ ID NO 133
<211> LENGTH: 15
<212> TYPE: DNA
<213> ORGANISM: Artificial sequence
<220> FEATURE:
<223> OTHER INFORMATION: R166.E3 HCDR1

<400> SEQUENCE: 133
agctgtgtgt tgatc                                                    15

<210> SEQ ID NO 134
<211> LENGTH: 15
<212> TYPE: DNA
<213> ORGANISM: Artificial sequence
<220> FEATURE:
<223> OTHER INFORMATION: R166.A5 HCDR1

<400> SEQUENCE: 134
aattatactg tcatc                                                    15

<210> SEQ ID NO 135
<211> LENGTH: 15
<212> TYPE: DNA
<213> ORGANISM: Artificial sequence
<220> FEATURE:
<223> OTHER INFORMATION: R166.H10 HCDR1

<400> SEQUENCE: 135
agctactgga tgagc                                                    15

<210> SEQ ID NO 136
<211> LENGTH: 48
<212> TYPE: DNA
<213> ORGANISM: Artificial sequence
<220> FEATURE:
<223> OTHER INFORMATION: R166.C5 HCDR2

<400> SEQUENCE: 136
atcatttatt ctggtggtac cagggactac gcgacctggg cgaaaggc               48

<210> SEQ ID NO 137
<211> LENGTH: 51
<212> TYPE: DNA
<213> ORGANISM: Artificial sequence
<220> FEATURE:
<223> OTHER INFORMATION: R166.H9 HCDR2

<400> SEQUENCE: 137
atgattggtg atggtgatga tgcagcatgg tacgcgagct gggcgaaagg c           51

<210> SEQ ID NO 138
<211> LENGTH: 51
<212> TYPE: DNA
<213> ORGANISM: Artificial sequence
<220> FEATURE:
<223> OTHER INFORMATION: R166.F2 HCDR2
```

-continued

```
<400> SEQUENCE: 138
tacatttatt atggtagtgg tagcacggac tacgcgagct gggcggaagg c          51

<210> SEQ ID NO 139
<211> LENGTH: 51
<212> TYPE: DNA
<213> ORGANISM: Artificial sequence
<220> FEATURE:
<223> OTHER INFORMATION: R166.H8 HCDR2

<400> SEQUENCE: 139
atcatttatg ctactggtgg taccagggac tacgcgacct gggcggcagg c          51

<210> SEQ ID NO 140
<211> LENGTH: 48
<212> TYPE: DNA
<213> ORGANISM: Artificial sequence
<220> FEATURE:
<223> OTHER INFORMATION: R166.E7 HCDR2

<400> SEQUENCE: 140
atcatttata ctggtggtac cagggactac gcgacctggg cgaaaggc             48

<210> SEQ ID NO 141
<211> LENGTH: 54
<212> TYPE: DNA
<213> ORGANISM: Artificial sequence
<220> FEATURE:
<223> OTHER INFORMATION: R166.G8 HCDR2

<400> SEQUENCE: 141
tgcattaatt ctggtagtaa ttcttatact tactacgcga actgggtgga tggc       54

<210> SEQ ID NO 142
<211> LENGTH: 48
<212> TYPE: DNA
<213> ORGANISM: Artificial sequence
<220> FEATURE:
<223> OTHER INFORMATION: R166.F9 HCDR2

<400> SEQUENCE: 142
ctcatcaata tttatgataa cacatactac gcgagctggg cgaaaggc             48

<210> SEQ ID NO 143
<211> LENGTH: 48
<212> TYPE: DNA
<213> ORGANISM: Artificial sequence
<220> FEATURE:
<223> OTHER INFORMATION: R166.G2 HCDR2

<400> SEQUENCE: 143
ctcatcaatc gttatggtaa cacatactac gcgagctggg cgaaaggc             48

<210> SEQ ID NO 144
<211> LENGTH: 48
<212> TYPE: DNA
<213> ORGANISM: Artificial sequence
<220> FEATURE:
<223> OTHER INFORMATION: R166.D1 HCDR2

<400> SEQUENCE: 144
gtcatttatc ctactggtac cacatactac gcgaactggg tgaaaggc             48

<210> SEQ ID NO 145
```

-continued

```
<211> LENGTH: 48
<212> TYPE: DNA
<213> ORGANISM: Artificial sequence
<220> FEATURE:
<223> OTHER INFORMATION: R166.G10 HCDR2

<400> SEQUENCE: 145
atcattggta gtggtggtag cacatactac gcgagctggg tgaatggt                       48

<210> SEQ ID NO 146
<211> LENGTH: 48
<212> TYPE: DNA
<213> ORGANISM: Artificial sequence
<220> FEATURE:
<223> OTHER INFORMATION: R166.G3 HCDR2

<400> SEQUENCE: 146
atcattggtt atggtggtaa cacaaactac gcgaactggg cgaaaggc                       48

<210> SEQ ID NO 147
<211> LENGTH: 48
<212> TYPE: DNA
<213> ORGANISM: Artificial sequence
<220> FEATURE:
<223> OTHER INFORMATION: R166.E5 HCDR2

<400> SEQUENCE: 147
atcgttacta gtagtggtag cacacactac gcgagctggg cgaatggt                       48

<210> SEQ ID NO 148
<211> LENGTH: 48
<212> TYPE: DNA
<213> ORGANISM: Artificial sequence
<220> FEATURE:
<223> OTHER INFORMATION: R166.E3 HCDR2

<400> SEQUENCE: 148
ttcatttatg gtagtggtaa cgcatactac gcgaactggg cgaaaggc                       48

<210> SEQ ID NO 149
<211> LENGTH: 48
<212> TYPE: DNA
<213> ORGANISM: Artificial sequence
<220> FEATURE:
<223> OTHER INFORMATION: R166.A5 HCDR2

<400> SEQUENCE: 149
atcatttttg gtagtggtgg cacatactac gcgacctggg cggaaggc                       48

<210> SEQ ID NO 150
<211> LENGTH: 48
<212> TYPE: DNA
<213> ORGANISM: Artificial sequence
<220> FEATURE:
<223> OTHER INFORMATION: R166.H10 HCDR2

<400> SEQUENCE: 150
atcattagtg gcagtggttc cacatactac gcgacctggg cgaaaggc                       48

<210> SEQ ID NO 151
<211> LENGTH: 36
<212> TYPE: DNA
<213> ORGANISM: Artificial sequence
<220> FEATURE:
<223> OTHER INFORMATION: R166.C5 HCDR3

<400> SEQUENCE: 151
```

-continued

```
gatcgtagtc ctgattatag tgccgccttt ctcttg                                   36

<210> SEQ ID NO 152
<211> LENGTH: 27
<212> TYPE: DNA
<213> ORGANISM: Artificial sequence
<220> FEATURE:
<223> OTHER INFORMATION: R166.H9 HCDR3

<400> SEQUENCE: 152
tatcttagtt tcactcggtt ggatctc                                             27

<210> SEQ ID NO 153
<211> LENGTH: 39
<212> TYPE: DNA
<213> ORGANISM: Artificial sequence
<220> FEATURE:
<223> OTHER INFORMATION: R166.F2 HCDR3

<400> SEQUENCE: 153
ggtggttatg ttggtggtgg tgttgatgct tttgatccc                                39

<210> SEQ ID NO 154
<211> LENGTH: 36
<212> TYPE: DNA
<213> ORGANISM: Artificial sequence
<220> FEATURE:
<223> OTHER INFORMATION: R166.H8 HCDR3

<400> SEQUENCE: 154
gatcgtagtc ctgattatag tgccgccttt aacttg                                   36

<210> SEQ ID NO 155
<211> LENGTH: 36
<212> TYPE: DNA
<213> ORGANISM: Artificial sequence
<220> FEATURE:
<223> OTHER INFORMATION: R166.E7 HCDR3

<400> SEQUENCE: 155
gatcgtagtc ctgattatag tgccgccttt aacttg                                   36

<210> SEQ ID NO 156
<211> LENGTH: 42
<212> TYPE: DNA
<213> ORGANISM: Artificial sequence
<220> FEATURE:
<223> OTHER INFORMATION: R166.G8 HCDR3

<400> SEQUENCE: 156
gatcgggatg ctgctgatac tagtgattgg tcacttaact tc                            42

<210> SEQ ID NO 157
<211> LENGTH: 36
<212> TYPE: DNA
<213> ORGANISM: Artificial sequence
<220> FEATURE:
<223> OTHER INFORMATION: R166.F9 HCDR3

<400> SEQUENCE: 157
tatggtactg atagtgattt ttattatctc gacttg                                   36

<210> SEQ ID NO 158
<211> LENGTH: 36
<212> TYPE: DNA
```

<213> ORGANISM: Artificial sequence
<220> FEATURE:
<223> OTHER INFORMATION: R166.G2 HCDR3

<400> SEQUENCE: 158
tatggtactg atagtgattt ttattttctc gacttg                                    36

<210> SEQ ID NO 159
<211> LENGTH: 45
<212> TYPE: DNA
<213> ORGANISM: Artificial sequence
<220> FEATURE:
<223> OTHER INFORMATION: R166.D1 HCDR3

<400> SEQUENCE: 159
aaacccatct tatatgttga tagtagtggt tggtatatcg acttg                          45

<210> SEQ ID NO 160
<211> LENGTH: 39
<212> TYPE: DNA
<213> ORGANISM: Artificial sequence
<220> FEATURE:
<223> OTHER INFORMATION: R166.G10 HCDR3

<400> SEQUENCE: 160
tatggtggta atagtggtgg ttatgattcc tttaacttg                                 39

<210> SEQ ID NO 161
<211> LENGTH: 51
<212> TYPE: DNA
<213> ORGANISM: Artificial sequence
<220> FEATURE:
<223> OTHER INFORMATION: R166.G3 HCDR3

<400> SEQUENCE: 161
gataataaaa gtggtggtaa taatggttac ccctactacg gcttggacct c                   51

<210> SEQ ID NO 162
<211> LENGTH: 24
<212> TYPE: DNA
<213> ORGANISM: Artificial sequence
<220> FEATURE:
<223> OTHER INFORMATION: R166.E5 HCDR3

<400> SEQUENCE: 162
gagggtggtt gggcttttga cttg                                                 24

<210> SEQ ID NO 163
<211> LENGTH: 39
<212> TYPE: DNA
<213> ORGANISM: Artificial sequence
<220> FEATURE:
<223> OTHER INFORMATION: R166.E3 HCDR3

<400> SEQUENCE: 163
tcccaagagg atgatagttt tggttatggc tttaacttg                                 39

<210> SEQ ID NO 164
<211> LENGTH: 36
<212> TYPE: DNA
<213> ORGANISM: Artificial sequence
<220> FEATURE:
<223> OTHER INFORMATION: R166.A5 HCDR3

<400> SEQUENCE: 164
ggttattttg gtaatacttt ttgggccatg gacccc                                    36

```
<210> SEQ ID NO 165
<211> LENGTH: 33
<212> TYPE: DNA
<213> ORGANISM: Artificial sequence
<220> FEATURE:
<223> OTHER INFORMATION: R166.H10 HCDR3

<400> SEQUENCE: 165
ggaaatcctc attatagttt tggttttaat atc                               33

<210> SEQ ID NO 166
<211> LENGTH: 39
<212> TYPE: DNA
<213> ORGANISM: Artificial sequence
<220> FEATURE:
<223> OTHER INFORMATION: R166.C5 LCDR1

<400> SEQUENCE: 166
caggccagtg agagtgttta tagtaataac cacttagcc                         39

<210> SEQ ID NO 167
<211> LENGTH: 39
<212> TYPE: DNA
<213> ORGANISM: Artificial sequence
<220> FEATURE:
<223> OTHER INFORMATION: R166.H9 LCDR1

<400> SEQUENCE: 167
cagtccagtc agagtgttta tcataacaac tggttagcc                         39

<210> SEQ ID NO 168
<211> LENGTH: 33
<212> TYPE: DNA
<213> ORGANISM: Artificial sequence
<220> FEATURE:
<223> OTHER INFORMATION: R166.F2 LCDR1

<400> SEQUENCE: 168
caggccagtc agagcattta cacctactta tcc                               33

<210> SEQ ID NO 169
<211> LENGTH: 39
<212> TYPE: DNA
<213> ORGANISM: Artificial sequence
<220> FEATURE:
<223> OTHER INFORMATION: R166.H8 LCDR1

<400> SEQUENCE: 169
caggccagtg agagtgttta tagtaacaac cacttagcc                         39

<210> SEQ ID NO 170
<211> LENGTH: 39
<212> TYPE: DNA
<213> ORGANISM: Artificial sequence
<220> FEATURE:
<223> OTHER INFORMATION: R166.E7 LCDR1

<400> SEQUENCE: 170
caggccagtg agagtgttta tagtaacaac cacttagcc                         39

<210> SEQ ID NO 171
<211> LENGTH: 39
<212> TYPE: DNA
<213> ORGANISM: Artificial sequence
<220> FEATURE:
```

-continued

<223> OTHER INFORMATION: R166.G8 LCDR1

<400> SEQUENCE: 171
cagtccagtg acagcgttaa taatgacaac tggttagcc                                    39

<210> SEQ ID NO 172
<211> LENGTH: 33
<212> TYPE: DNA
<213> ORGANISM: Artificial sequence
<220> FEATURE:
<223> OTHER INFORMATION: R166.F9 LCDR1

<400> SEQUENCE: 172
caggccagtc agaacattta cacctactta tcc                                          33

<210> SEQ ID NO 173
<211> LENGTH: 33
<212> TYPE: DNA
<213> ORGANISM: Artificial sequence
<220> FEATURE:
<223> OTHER INFORMATION: R166.G2 LCDR1

<400> SEQUENCE: 173
caggccagtc agagcattta cagctactta tcc                                          33

<210> SEQ ID NO 174
<211> LENGTH: 33
<212> TYPE: DNA
<213> ORGANISM: Artificial sequence
<220> FEATURE:
<223> OTHER INFORMATION: R166.D1 LCDR1

<400> SEQUENCE: 174
caggccagtg agaacattaa caactactta tcc                                          33

<210> SEQ ID NO 175
<211> LENGTH: 33
<212> TYPE: DNA
<213> ORGANISM: Artificial sequence
<220> FEATURE:
<223> OTHER INFORMATION: R166.G10 LCDR1

<400> SEQUENCE: 175
caggccagtc agagcattta cagccacttg tcc                                          33

<210> SEQ ID NO 176
<211> LENGTH: 33
<212> TYPE: DNA
<213> ORGANISM: Artificial sequence
<220> FEATURE:
<223> OTHER INFORMATION: R166.G3 LCDR1

<400> SEQUENCE: 176
caggccagtc agagcatcag tagccactta gcc                                          33

<210> SEQ ID NO 177
<211> LENGTH: 39
<212> TYPE: DNA
<213> ORGANISM: Artificial sequence
<220> FEATURE:
<223> OTHER INFORMATION: R166.E5 LCDR1

<400> SEQUENCE: 177
cagtccagtg agagtgttgc taatagcaat tggttatcc                                    39

-continued

```
<210> SEQ ID NO 178
<211> LENGTH: 33
<212> TYPE: DNA
<213> ORGANISM: Artificial sequence
<220> FEATURE:
<223> OTHER INFORMATION: R166.E3 LCDR1

<400> SEQUENCE: 178
caggccagtc agagcattgg tacctactta tcc                                  33

<210> SEQ ID NO 179
<211> LENGTH: 33
<212> TYPE: DNA
<213> ORGANISM: Artificial sequence
<220> FEATURE:
<223> OTHER INFORMATION: R166.A5 LCDR1

<400> SEQUENCE: 179
caggccagtc agagcattag tacttattta tcc                                  33

<210> SEQ ID NO 180
<211> LENGTH: 33
<212> TYPE: DNA
<213> ORGANISM: Artificial sequence
<220> FEATURE:
<223> OTHER INFORMATION: R166.H10 LCDR1

<400> SEQUENCE: 180
caggccagtg aaagtattta tagttggtta tcc                                  33

<210> SEQ ID NO 181
<211> LENGTH: 21
<212> TYPE: DNA
<213> ORGANISM: Artificial sequence
<220> FEATURE:
<223> OTHER INFORMATION: R166.C5 LCDR2

<400> SEQUENCE: 181
tctgcatcca ctctggaatc t                                               21

<210> SEQ ID NO 182
<211> LENGTH: 21
<212> TYPE: DNA
<213> ORGANISM: Artificial sequence
<220> FEATURE:
<223> OTHER INFORMATION: R166.H9 LCDR2

<400> SEQUENCE: 182
ggtgcggcca ctctggcatc t                                               21

<210> SEQ ID NO 183
<211> LENGTH: 21
<212> TYPE: DNA
<213> ORGANISM: Artificial sequence
<220> FEATURE:
<223> OTHER INFORMATION: R166.F2 LCDR2

<400> SEQUENCE: 183
agggcgtcca ctctggcatc t                                               21

<210> SEQ ID NO 184
<211> LENGTH: 21
<212> TYPE: DNA
<213> ORGANISM: Artificial sequence
<220> FEATURE:
<223> OTHER INFORMATION: R166.H8 LCDR2
```

-continued

```
<400> SEQUENCE: 184
tctgcgtcca ctctggaatc t                                              21

<210> SEQ ID NO 185
<211> LENGTH: 21
<212> TYPE: DNA
<213> ORGANISM: Artificial sequence
<220> FEATURE:
<223> OTHER INFORMATION: R166.E7 LCDR2

<400> SEQUENCE: 185
tctgcatcca ctctggaatc t                                              21

<210> SEQ ID NO 186
<211> LENGTH: 21
<212> TYPE: DNA
<213> ORGANISM: Artificial sequence
<220> FEATURE:
<223> OTHER INFORMATION: R166.G8 LCDR2

<400> SEQUENCE: 186
caggcatcca aactggcatc t                                              21

<210> SEQ ID NO 187
<211> LENGTH: 21
<212> TYPE: DNA
<213> ORGANISM: Artificial sequence
<220> FEATURE:
<223> OTHER INFORMATION: R166.F9 LCDR2

<400> SEQUENCE: 187
aaggcatcca ctctggcatc t                                              21

<210> SEQ ID NO 188
<211> LENGTH: 21
<212> TYPE: DNA
<213> ORGANISM: Artificial sequence
<220> FEATURE:
<223> OTHER INFORMATION: R166.G2 LCDR2

<400> SEQUENCE: 188
aaggcatcca aactggtatc t                                              21

<210> SEQ ID NO 189
<211> LENGTH: 21
<212> TYPE: DNA
<213> ORGANISM: Artificial sequence
<220> FEATURE:
<223> OTHER INFORMATION: R166.D1 LCDR2

<400> SEQUENCE: 189
caggcatcca gactggcatc t                                              21

<210> SEQ ID NO 190
<211> LENGTH: 21
<212> TYPE: DNA
<213> ORGANISM: Artificial sequence
<220> FEATURE:
<223> OTHER INFORMATION: R166.G10 LCDR2

<400> SEQUENCE: 190
ggtgcatcca ccctggcatc t                                              21

<210> SEQ ID NO 191
<211> LENGTH: 21
```

```
<212> TYPE: DNA
<213> ORGANISM: Artificial sequence
<220> FEATURE:
<223> OTHER INFORMATION: R166.G3 LCDR2

<400> SEQUENCE: 191
tatgcgtcca ctctggcatc t                                         21

<210> SEQ ID NO 192
<211> LENGTH: 21
<212> TYPE: DNA
<213> ORGANISM: Artificial sequence
<220> FEATURE:
<223> OTHER INFORMATION: R166.E5 LCDR2

<400> SEQUENCE: 192
tgggcatcca aattggcatc t                                         21

<210> SEQ ID NO 193
<211> LENGTH: 21
<212> TYPE: DNA
<213> ORGANISM: Artificial sequence
<220> FEATURE:
<223> OTHER INFORMATION: R166.E3 LCDR2

<400> SEQUENCE: 193
agggcatcca ctctgacatc t                                         21

<210> SEQ ID NO 194
<211> LENGTH: 21
<212> TYPE: DNA
<213> ORGANISM: Artificial sequence
<220> FEATURE:
<223> OTHER INFORMATION: R166.A5 LCDR2

<400> SEQUENCE: 194
caggcatccg aattggcata t                                         21

<210> SEQ ID NO 195
<211> LENGTH: 21
<212> TYPE: DNA
<213> ORGANISM: Artificial sequence
<220> FEATURE:
<223> OTHER INFORMATION: R166.H10 LCDR2

<400> SEQUENCE: 195
agtgcatcct atctggcatc t                                         21

<210> SEQ ID NO 196
<211> LENGTH: 36
<212> TYPE: DNA
<213> ORGANISM: Artificial sequence
<220> FEATURE:
<223> OTHER INFORMATION: R166.C5 LCDR3

<400> SEQUENCE: 196
gcaggataca aaagtagcga tactgatggt acttct                         36

<210> SEQ ID NO 197
<211> LENGTH: 33
<212> TYPE: DNA
<213> ORGANISM: Artificial sequence
<220> FEATURE:
<223> OTHER INFORMATION: R166.H9 LCDR3

<400> SEQUENCE: 197
```

-continued

```
gcaggcgttt ataatgatga tagtgagaat gct                                    33

<210> SEQ ID NO 198
<211> LENGTH: 36
<212> TYPE: DNA
<213> ORGANISM: Artificial sequence
<220> FEATURE:
<223> OTHER INFORMATION: R166.F2 LCDR3

<400> SEQUENCE: 198
caacagggtg ctcttagtag caatattcat aacact                                 36

<210> SEQ ID NO 199
<211> LENGTH: 36
<212> TYPE: DNA
<213> ORGANISM: Artificial sequence
<220> FEATURE:
<223> OTHER INFORMATION: R166.H8 LCDR3

<400> SEQUENCE: 199
gcaggataca aaagtagcga tactgatggt acttct                                 36

<210> SEQ ID NO 200
<211> LENGTH: 36
<212> TYPE: DNA
<213> ORGANISM: Artificial sequence
<220> FEATURE:
<223> OTHER INFORMATION: R166.E7 LCDR3

<400> SEQUENCE: 200
gcaggataca aaagtagcga tactgatggt acttct                                 36

<210> SEQ ID NO 201
<211> LENGTH: 36
<212> TYPE: DNA
<213> ORGANISM: Artificial sequence
<220> FEATURE:
<223> OTHER INFORMATION: R166.G8 LCDR3

<400> SEQUENCE: 201
caaggcactg gttatagtag tacttggtac gttgct                                 36

<210> SEQ ID NO 202
<211> LENGTH: 36
<212> TYPE: DNA
<213> ORGANISM: Artificial sequence
<220> FEATURE:
<223> OTHER INFORMATION: R166.F9 LCDR3

<400> SEQUENCE: 202
caaagcgatt ggcttattag tagtaatggg aatact                                 36

<210> SEQ ID NO 203
<211> LENGTH: 36
<212> TYPE: DNA
<213> ORGANISM: Artificial sequence
<220> FEATURE:
<223> OTHER INFORMATION: R166.G2 LCDR3

<400> SEQUENCE: 203
caaagcgatt ggcttattag tagtaatggg aatact                                 36

<210> SEQ ID NO 204
<211> LENGTH: 39
<212> TYPE: DNA
<213> ORGANISM: Artificial sequence
```

<220> FEATURE:
<223> OTHER INFORMATION: R166.D1 LCDR3

<400> SEQUENCE: 204
caacagggcc atagtgttag taatgatgtt ggtaatgtt                          39

<210> SEQ ID NO 205
<211> LENGTH: 36
<212> TYPE: DNA
<213> ORGANISM: Artificial sequence
<220> FEATURE:
<223> OTHER INFORMATION: R166.G10 LCDR3

<400> SEQUENCE: 205
caatgtactg ctggtactag tatttatggt aatgct                            36

<210> SEQ ID NO 206
<211> LENGTH: 36
<212> TYPE: DNA
<213> ORGANISM: Artificial sequence
<220> FEATURE:
<223> OTHER INFORMATION: R166.G3 LCDR3

<400> SEQUENCE: 206
caccagtctt atagtggtag tgatgttgat aatact                            36

<210> SEQ ID NO 207
<211> LENGTH: 30
<212> TYPE: DNA
<213> ORGANISM: Artificial sequence
<220> FEATURE:
<223> OTHER INFORMATION: R166.E5 LCDR3

<400> SEQUENCE: 207
caaggcggct atactagtga tcgtcgtgct                                   30

<210> SEQ ID NO 208
<211> LENGTH: 36
<212> TYPE: DNA
<213> ORGANISM: Artificial sequence
<220> FEATURE:
<223> OTHER INFORMATION: R166.E3 LCDR3

<400> SEQUENCE: 208
caagagggtt atagtgatat taatgttaat aatatt                            36

<210> SEQ ID NO 209
<211> LENGTH: 36
<212> TYPE: DNA
<213> ORGANISM: Artificial sequence
<220> FEATURE:
<223> OTHER INFORMATION: R166.A5 LCDR3

<400> SEQUENCE: 209
cagcagggtt atagtgatat taatgtcgat aatttt                            36

<210> SEQ ID NO 210
<211> LENGTH: 39
<212> TYPE: DNA
<213> ORGANISM: Artificial sequence
<220> FEATURE:
<223> OTHER INFORMATION: R166.H10 LCDR3

<400> SEQUENCE: 210
caatacaatt atgatagtgg tgatggtatt actaatggt                          39

```
<210> SEQ ID NO 211
<211> LENGTH: 351
<212> TYPE: DNA
<213> ORGANISM: Artificial sequence
<220> FEATURE:
<223> OTHER INFORMATION: R166.C5 HCVR

<400> SEQUENCE: 211
cagtcggtgg aggagtccgg gggtcgcctg gtcacgcctg ggacacccct gacactcacc      60
tgcacagtct ctggattctc cctaaggaac tttgcaatga gctgggtccg ccaggctcca     120
gggaagggcc tggaatggat cggaatcatt tattctggtg gtaccaggga ctacgcgacc     180
tgggcgaaag gccgattcac catctccaaa acctcgacca cggtggatct gaaaatgacc     240
agtccgacaa ctgaggacac ggccacctat ttctgtgcca gagatcgtag tcctgattat     300
agtgccgcct ttctcttgtg gggccaaggc accctggtca ccgtctcctc a              351

<210> SEQ ID NO 212
<211> LENGTH: 345
<212> TYPE: DNA
<213> ORGANISM: Artificial sequence
<220> FEATURE:
<223> OTHER INFORMATION: R166.H9 HCVR

<400> SEQUENCE: 212
cagtccctgg aggagtccgg gggtcgcctg gtcacgcctg ggacacccct gacactcacc      60
tgcacagcct ctggattctc cctcaataac tacaacatga tctgggtccg ccaggctcca     120
ggggaggggc tggaatggat cggaatgatt ggtgatggtg atgatgcagc atggtacgcg     180
agctgggcga aaggccgatt caccatctcc aaaacctcga ccacggtgga tctggaagtg     240
accagtctga caaccgagga cacggccatt tattttgtgt ccagatatct tagtttcact     300
cggttggatc tctggggcca gggcaccctg gtcaccgtct cctca                     345

<210> SEQ ID NO 213
<211> LENGTH: 363
<212> TYPE: DNA
<213> ORGANISM: Artificial sequence
<220> FEATURE:
<223> OTHER INFORMATION: R166.F2 HCVR

<400> SEQUENCE: 213
cagtcggtgg aggagtccgg gggtcgcctg gtcacgcctg ggacacccct gacactcacc      60
tgcacagcct ctggattcac catcagtagc cacgacatga gttgggtccg ccaggctcca     120
gggaaggggc tggaatggat cggatacatt tattatggta gtggtagcac ggactacgcg     180
agctgggcgg aaggccgatt caccatcacc agaaacacca cgagaacac ggtgactctg      240 aaaatgacca gtctgacaac cgaggacacg gccacctatt tctgtgccag aggtggttat     300
gttggtggtg gtgttgatgc ttttgatccc tggggcccag gcaccgtggt caccgtctcc     360
tca                                                                   363

<210> SEQ ID NO 214
<211> LENGTH: 354
<212> TYPE: DNA
<213> ORGANISM: Artificial sequence
<220> FEATURE:
<223> OTHER INFORMATION: R166.H8 HCVR

<400> SEQUENCE: 214
cagtcggtgg aggagtccgg gggtcgcctg gtcacgcctg ggacacccct gacactcacc      60
```

-continued

```
tgcacagtct ctggattctc cctaagtagc tttgcaatga gctgggtccg ccaggctcca      120
gggaagggcc tggaatggat cggaatcatt tatgctactg gtggtaccag ggactacgcg      180
acctgggcgg caggccgttt caccatctcc aaaacctcga ccacggtggg tctgaaaatg      240
accagtccga caactgagga cacggccacc tatttctgtg ccagagatcg tagtcctgat      300
tatagtgccg cctttaactt gtggggccaa ggcaccctgg tcaccgtctc ctca           354

<210> SEQ ID NO 215
<211> LENGTH: 351
<212> TYPE: DNA
<213> ORGANISM: Artificial sequence
<220> FEATURE:
<223> OTHER INFORMATION: R166.E7 HCVR

<400> SEQUENCE: 215
cagtcggtgg aggagtccgg gggtcgcctg gtcacgcctg ggacacccct gacactcacc       60
tgcacagtct ctggattctc cctaagtagc tttgcaatga gctgggtccg ccaggctcca      120
gggaagggcc tggaatggat cggaatcatt tatactggtg gtaccaggga ctacgcgacc      180
tgggcgaaag gccgattcac catctccaaa acctcgacca cggtggatct gaaaatgacc      240
agtccgacaa ctgaggacac ggccacctat ttctgtgcca gagatcgtag tcctgattat      300
agtgccgcct ttaacttgtg gggccaaggc accctggtca ccgtctcctc a               351

<210> SEQ ID NO 216
<211> LENGTH: 384
<212> TYPE: DNA
<213> ORGANISM: Artificial sequence
<220> FEATURE:
<223> OTHER INFORMATION: R166.G8 HCVR

<400> SEQUENCE: 216
cagctgctgg agcagtccgg aggaggagcc gaaggaggcc tggtcaagcc tggggggatcc      60 ctggaactct gctgcaaagc ctctggattc tcccttagta atatctactg gatatgttgg      120
gtccgccagg ctccagggac ggggctggag tggattggat gcattaattc tggtagtaat      180
tcttatactt actacgcgaa ctgggtggat ggccgattca ctctctccag agacatcgac      240
cagagcacag gttgcctaca actgaacagt ctgacagccg cggacacggc catgtattat      300
tgtgcgagag atcgggatgc tgctgatact agtgattggt cacttaactt ctggggccaa      360
ggcaccctgg tcaccgtctc ctcg                                             384

<210> SEQ ID NO 217
<211> LENGTH: 351
<212> TYPE: DNA
<213> ORGANISM: Artificial sequence
<220> FEATURE:
<223> OTHER INFORMATION: R166.F9 HCVR

<400> SEQUENCE: 217
cagtcgctgg aggagtccgg gggtcgcctg gtcaagcctg acgagaccct gacaatcacc       60
tgcacagtct ctggaatcga cctcagtagc aatgcaatgg gctgggtccg ccaggctcca      120
gggaaggggc tggagtggat cggactcatc aatatttatg ataacacata ctacgcgagc      180
tgggcgaaag gccgattcac catctccaaa acctcgacca cggtggattt gaaagtgacc      240
agtctgacaa ccgaggacac ggccacctat ttctgtgcca gatatggtac tgatagtgat      300
ttttattatc tcgacttgtg gggccaaggc accctggtca ccgtctcctc a               351
```

```
<210> SEQ ID NO 218
<211> LENGTH: 351
<212> TYPE: DNA
<213> ORGANISM: Artificial sequence
<220> FEATURE:
<223> OTHER INFORMATION: R166.G2 HCVR

<400> SEQUENCE: 218
cagtcgctgg aggagtccgg gggtcgcctg gtcaagcctg acgaaaccct gacaatcacc      60
tgcacagtct ctggaatcga cctcagtagc gatgcgatga gctgggtccg ccaggctcca     120
gggaaggggc tggaatggat cggactcatc aatcgttatg gtaacacata ctacgcgagc     180
tgggcgaaag gccgatttac catctccaaa acctcgacca cggtggattt gaaagtgacc     240
agtctgacaa ccgaggacac ggccacctat ttctgtgcca gatatggtac tgatagtgat     300
ttttattttc tcgacttgtg gggccaaggc accctggtca ccgtctcctc a              351

<210> SEQ ID NO 219
<211> LENGTH: 360
<212> TYPE: DNA
<213> ORGANISM: Artificial sequence
<220> FEATURE:
<223> OTHER INFORMATION: R166.D1 HCVR

<400> SEQUENCE: 219
cagtcggtgg aggagtccgg cggtcgcctg gtaaagcctg acgaatccct gacactcacc      60
tgcacagtct ctggattctc cctcagcaac tacgacatga tctgggtccg ccaggctcca     120
gggaaggggc tggaatggat cggagtcatt tatcctactg gtaccacata ctacgcgaac     180
tgggtgaaag gccgattcac catctccaaa acctcgacca cggtgggtct gctcatcacc     240
agtccgacga ccgaggacac ggccacctat ttctgtgcca gaaaacccat cttatatgtt     300
gatagtagtg gttggtatat cgacttgtgg ggccaaggca ccctggtcac cgtctcctca     360

<210> SEQ ID NO 220
<211> LENGTH: 354
<212> TYPE: DNA
<213> ORGANISM: Artificial sequence
<220> FEATURE:
<223> OTHER INFORMATION: R166.G10 HCVR

<400> SEQUENCE: 220
cagtcggtgg aggagtccgg gggtcgccta gtcacgcctg ggacacccct gacactcacc      60
tgcacagtct ctggattctc cctcagtagc tctgcagtga gctgggtccg ccaggctcca     120
gggaaggggc tggaatacat cggaatcatt ggtagtggtg gtagcacata ctacgcgagc     180
tgggtgaatg gtcgattcac catctccaaa acctcgacca cggtggatct gaaaatgacc     240
agtctgacag ccgcggacac ggccacctat ttctgtgcca gatatggtgg taatagtggt     300
ggttatgatt cctttaactt gtggggccaa ggcaccctgg tcaccgtctc ctca           354

<210> SEQ ID NO 221
<211> LENGTH: 369
<212> TYPE: DNA
<213> ORGANISM: Artificial sequence
<220> FEATURE:
<223> OTHER INFORMATION: R166.G3 HCVR

<400> SEQUENCE: 221
cagtcggtgg aggagtccgg gggtcgcctg gtcacgcctg ggacacccct gacactcacc      60
tgcacagtct ctggaatcga cctcagtaga tatgcaatgg gctgggtccg ccaggctcca     120
```

-continued

```
gggaaggggc tggaatacat cggaatcatt ggttatggtg gtaacacaaa ctacgcgaac      180
tgggcgaaag gccgattcac catctccaaa acctcgtcga ccacggtgga tctgaaaatg      240
accagtccga caaccgagga cacggccacc tatttctgtg ccagagataa taaaagtggt      300
ggtaataatg gttacccccta ctacggcttg gacctctggg gcccagggac cctcgtcacc      360
gtctcttca                                                             369
```

```
<210> SEQ ID NO 222
<211> LENGTH: 342
<212> TYPE: DNA
<213> ORGANISM: Artificial sequence
<220> FEATURE:
<223> OTHER INFORMATION: R166.E5 HCVR

<400> SEQUENCE: 222
cagtcgctgg aggagtccgg gggtcgcctg gtcacgcctg ggacacccct gacactcacc       60
tgcacagcct ctggattctc cctcagtggc tactacatga tctgggtccg ccaggctcca      120
gggaaggggc tggaatacat cggaatcgtt actagtagtg gtagcacaca ctacgcgagc      180
tgggcgaatg gtcgattcgc catctccaaa acctcgtcga ccacggtgga tctgaaaatg      240
cccagtctga caaccgagga cacggccacc tatttctgtg ccagagaggg tggttgggct      300
tttgacttgt ggggccaagg caccctggtc accgtctcct ca                        342
```

```
<210> SEQ ID NO 223
<211> LENGTH: 357
<212> TYPE: DNA
<213> ORGANISM: Artificial sequence
<220> FEATURE:
<223> OTHER INFORMATION: R166.E3 HCVR

<400> SEQUENCE: 223
cagtcgctgg aggagtccgg gggtcgcctg gtcacgcctg ggacacccct gacactcacc       60
tgcacagtct ctggaatcga cctcagtagc tgtgtgttga tctgggtccg ccaggctcca      120
gaaaaggggc tggaatggat cggattcatt tatggtagtg gtaacgcata ctacgcgaac      180
tgggcgaaag gccgattcac catctccaaa acctcgtcga ccacggtgga tctgaaaatc      240
accagtccga caaccgagga cacggccacc tatttctgtg ccagatccca agaggatgat      300
agttttggtt atggctttaa cttgtggggc caaggcaccc tggtcaccgt ctcctca         357
```

```
<210> SEQ ID NO 224
<211> LENGTH: 351
<212> TYPE: DNA
<213> ORGANISM: Artificial sequence
<220> FEATURE:
<223> OTHER INFORMATION: R166.A5 HCVR

<400> SEQUENCE: 224
cagtcggtgg aggagtccgg gggtcgcctg gtcacgcctg ggacacccct gacactcacc       60
tgcacagtct ctggattctc cctcaataat tatactgtca tctgggtccg ccaggctcca      120
gggaaggggc tggaatggat cggaatcatt tttggtagtg gtggcacata ctacgcgacc      180
tgggcggaag gccgattcac catctccaga acctcgacca cggtggatct gaaaatgacc      240
agtccgacaa ccgaggacac ggccacctat ttctgtgcca gaggttattt tggtaatact      300
ttttgggcca tggacccctg gggcccaggg accctcgtca ccgtctcttc a               351
```

```
<210> SEQ ID NO 225
```

-continued

```
<211> LENGTH: 351
<212> TYPE: DNA
<213> ORGANISM: Artificial sequence
<220> FEATURE:
<223> OTHER INFORMATION: R166.H10 HCVR

<400> SEQUENCE: 225
cagtcgctgg aggagtccgg gggtcgcctg gtcacgcctg ggacacccct gacactcacc      60
tgcacagcct ctggattctc cctcagtagc tactggatga gctgggtccg ccaggctcca     120
gggaaggggc tggaatatat cggaatcatt agtggcagtg gttccacata ctacgcgacc     180
tgggcgaaag gccgattcac catctccaaa acctcgtcga ccacggtgga tctgaaaatc     240
accagtccga caaccgagga cacggccacc tatttctgtg ccagaggaaa tcctcattat     300
agttttggtt ttaatatctg gggcccaggc accctggtca ccgtctcctt g             351

<210> SEQ ID NO 226
<211> LENGTH: 333
<212> TYPE: DNA
<213> ORGANISM: Artificial sequence
<220> FEATURE:
<223> OTHER INFORMATION: R166.C5 LCVR

<400> SEQUENCE: 226
atcgtgatga cccagactcc atcttccaag tctgtccctg tgggagacac agtcaccatc      60
aattgccagg ccagtgagag tgtttatagt aataaccact tagcctggtt tcaacagaaa     120
ccagggcagc ctcccaagct cctgatctat tctgcatcca ctctggaatc tggggtccca     180
tcgcggttca aaggcagtgg atctgggaca cagttcactc tcaccatcag cggcgtgcag     240
tgtgacgatg ctgccactta ctactgtgca ggatacaaaa gtagcgatac tgatggtact     300
tctttcggcg agggaccgga ggtggtggtc aaa                                  333

<210> SEQ ID NO 227
<211> LENGTH: 330
<212> TYPE: DNA
<213> ORGANISM: Artificial sequence
<220> FEATURE:
<223> OTHER INFORMATION: R166.H9 LCVR

<400> SEQUENCE: 227
gccgtgctga cccagactcc atctcccgtg tctgcagctg tgggaggcac agtcaccatc      60
aattgccagt ccagtcagag tgtttatcat aacaactggt tagcctggta tcagcagaaa     120
ccagggcagc ctcccaagct cctgatctat ggtgcggcca ctctggcatc tggggtccca     180
tcgcggttta aaggcagtgg atctgggaca cagttcactt tcactatcac cgacgtgcag     240
tgtgacgatg ttggcactta ctactgtgca ggcgtttata atgatgatag tgagaatgct     300
ttcggcggag ggaccgaggt ggtggtcaaa                                      330

<210> SEQ ID NO 228
<211> LENGTH: 330
<212> TYPE: DNA
<213> ORGANISM: Artificial sequence
<220> FEATURE:
<223> OTHER INFORMATION: R166.F2 LCVR

<400> SEQUENCE: 228
gcctatgata tgacccagac tccagcctct gtggaggtag ctgtgggagg cacagtcacc      60
atcaagtgcc aggccagtca gagcatttac acctacttat cctggtatca gcagaaacca     120
gggcagcctc ccaagctcct gatctacagg gcgtccactc tggcatctgg ggtctcatcg     180
```

```
cggttcaaag gcagtggatc tgggacagat ttcactctca ccatcagcgg cgcgcagtgt    240
gccgatgctg ccacttacta ttgtcaacag ggtgctctta gtagcaatat tcataacact    300
ttcggcggag ggaccgaggt ggtggtcaaa                                     330

<210> SEQ ID NO 229
<211> LENGTH: 333
<212> TYPE: DNA
<213> ORGANISM: Artificial sequence
<220> FEATURE:
<223> OTHER INFORMATION: R166.H8 LCVR

<400> SEQUENCE: 229
atcgtgatga cccagactcc atcttccaag tctgtccctg tgggagacac agtcaccatc     60
aattgccagg ccagtgagag tgtttatagt aacaaccact tagcctggtt tcaacagaaa    120
ccagggcagc ctcccaagct cctgatctat tctgcgtcca ctctggaatc tggggtccca    180
tcgcggttca aaggcagtgg atctgggaca cagttcactc tcaccatcag cggcgtgcag    240
tgtgacgatg ctgccactta ctactgtgca ggatacaaaa gtagcgatac tgatggtact    300
tctttcggcg agggaccgga ggtggtggtc aaa                                 333

<210> SEQ ID NO 230
<211> LENGTH: 333
<212> TYPE: DNA
<213> ORGANISM: Artificial sequence
<220> FEATURE:
<223> OTHER INFORMATION: R166.E7 LCVR

<400> SEQUENCE: 230
atcgtgatga cccagactcc atcttccaag tctgtccctg tgggagacac agtcaccatc     60
aattgccagg ccagtgagag tgtttatagt aacaaccact tagcctggtt tcaacagaaa    120
ccagggcagc ctcccaagct cctgatctat tctgcatcca ctctggaatc tggggtccca    180
tcgcggttca aaggcagtgg atctgggaca cagttcactc tcaccatcag cggcgtgcag    240
tgtgacgatg ctgccactta ctactgtgca ggatacaaaa gtagcgatac tgatggtact    300
tctttcggcg agggaccgga ggtggtggtc aaa                                 333

<210> SEQ ID NO 231
<211> LENGTH: 333
<212> TYPE: DNA
<213> ORGANISM: Artificial sequence
<220> FEATURE:
<223> OTHER INFORMATION: R166.G8 LCVR

<400> SEQUENCE: 231
caagtgctga cccagactcc atcctccgtg tctgcagctg tgggaggcac agtcaccatc     60
agttgccagt ccagtgacag cgttaataat gacaactggt tagcctggta tcagcagaaa    120
ccagggcagc ctcccaagct cctgatctac caggcatcca aactggcatc tggggtccca    180
tcccggttca gcggcagtgg atctgggaca cagttcactc tcaccatcag cggcgtgcag    240
tgtgacgatg ctgccaatta ctactgtcaa ggcactggtt atagtagtac ttggtacgtt    300
gctttcggcg agggaccgga ggtggtggtc aaa                                 333

<210> SEQ ID NO 232
<211> LENGTH: 348
<212> TYPE: DNA
<213> ORGANISM: Artificial sequence
<220> FEATURE:
```

-continued

<223> OTHER INFORMATION: R166.F9 LCVR

<400> SEQUENCE: 232
gctgacattg tgatgaccca gactccagcc tccgtgtctg aacctgtggg aggcacagtc      60
accatcaagt gccaggccag tcagaacatt tacacctact tatcctggta tcagcagaaa     120
ccagggcagc ctcccaagct cctgatctac aaggcatcca ctctggcatc tggggtctca     180
tcgcggttca aaggcagtgg atctgggaca gagttcactc tcaccatcaa cgacctggag     240
tgtgccgatg ctgccactta ctactgtcaa agcgattggc ttattagtag taatgggaat     300
actttcggcg gagggaccga ggtggtggtc acaggtgatc cagttgca                 348

<210> SEQ ID NO 233
<211> LENGTH: 333
<212> TYPE: DNA
<213> ORGANISM: Artificial sequence
<220> FEATURE:
<223> OTHER INFORMATION: R166.G2 LCVR

<400> SEQUENCE: 233
gctgacattg tgatgaccca gactccagcc tccgtgtctg aacctgtggg aggcacagtc      60
accatcaagt gccaggccag tcagagcatt tacagctact tatcctggta tcagcagaaa     120
ccagggcagc gtcccaaact cctgatctac aaggcatcca aactggtatc tggggtccca     180
tcgcggttca gaggcagtgg atctgggaca gagttcactc tcaccatcag cgacctggag     240
tgtgccgatg ctgcctctta ctactgtcaa agcgattggc ttattagtag taatgggaat     300
actttcggcg gagggaccga ggtggtggtc aca                                  333

<210> SEQ ID NO 234
<211> LENGTH: 333
<212> TYPE: DNA
<213> ORGANISM: Artificial sequence
<220> FEATURE:
<223> OTHER INFORMATION: R166.D1 LCVR

<400> SEQUENCE: 234
gcctatgata tgacccagac tccatcctcc gtgtctgcag ctgtgggagg cacagtcagc      60
atcaagtgcc aggccagtga gaacattaac aactacttat cctggtatca gcagaaacca     120
gggcagcctc ccaagctcct gatctaccag gcatccagac tggcatctgc ggtcccatcg     180
cggttcaaag gcagtggatc tgggacacag ttcactctca ccatcgacga cctggagtgt     240
gccgatgctg ccacttacta ctgtcaacag ggccatagtg ttagtaatga tgttggtaat     300
gttttcggcg gagggaccga ggtggtggtc aaa                                  333

<210> SEQ ID NO 235
<211> LENGTH: 330
<212> TYPE: DNA
<213> ORGANISM: Artificial sequence
<220> FEATURE:
<223> OTHER INFORMATION: R166.G10 LCVR

<400> SEQUENCE: 235
gatgttgtga tgacccagac tccagcctcc gtgtctgaac tgtgggagg cacagtcacc       60 atcaagtgcc aggccagtca gagcatttac agccacttgt cctggtatca gcagaaacca     120
gggcagcctc ccaagctcct gatccatggt gcatccaccc tggcatctgg ggcctcatcg     180
cggtttaaag ccagtggatc tgggacagag ttcactctca ccatcagcga cctggagtgt     240
gccgatgctg ccacttacta ctgtcaatgt actgctggta ctagtattta tggtaatgct     300

-continued

```
ttcggcggag ggaccgaggt ggtggtcaga                                          330

<210> SEQ ID NO 236
<211> LENGTH: 330
<212> TYPE: DNA
<213> ORGANISM: Artificial sequence
<220> FEATURE:
<223> OTHER INFORMATION: R166.G3 LCVR

<400> SEQUENCE: 236
gcctatgata tgacccagac tccagcctct gtggaggtac ctgtgggagg cacagtcacc         60
atcaattgcc aggccagtca gagcatcagt agccacttag cctggtatca gcagaaacga        120
gggcagcctc ccaaggtcct gatctattat gcgtccactc tggcatctgg ggtctcatcg        180
cggttcaaag gcagtggatc tgggacagag tacactctca ccattagcgg cgtggagtgt        240
gccgatgctg ccacttactt ttgtcaccag tcttatagtg gtagtgatgt tgataatact        300
ttcggcggag ggaccgaggt ggtggtcaga                                          330

<210> SEQ ID NO 237
<211> LENGTH: 327
<212> TYPE: DNA
<213> ORGANISM: Artificial sequence
<220> FEATURE:
<223> OTHER INFORMATION: R166.E5 LCVR

<400> SEQUENCE: 237
caagtgctga cccagactcc attctccgtg tctacagctg tgggaggcac agtcaccatc         60
aattgccagt ccagtgagag tgttgctaat agcaattggt tatcctggta tcagcagaaa        120
ccaggacagc ctcccaagct cctgatctac tgggcatcca aattggcatc tggggtccca        180
tcgcggttca gtggcagtgg atctgggaca cagttcactc tcaccatcag cggcgtgcag        240
tgtgccgatg ctgccactta ctactgtcaa ggcggctata ctagtgatcg tcgtgctttc        300
ggcggaggga ccgaggtggt ggtcaaa                                             327

<210> SEQ ID NO 238
<211> LENGTH: 330
<212> TYPE: DNA
<213> ORGANISM: Artificial sequence
<220> FEATURE:
<223> OTHER INFORMATION: R166.E3 LCVR

<400> SEQUENCE: 238
gcctatgata tgacccagac tccagcctct gtggaggtag ctgtgggagg cacagtcacc         60
atcaattgcc aggccagtca gagcattggt acctacttat cctggtatca acagaaacca        120
gggcagcctc ccaagctcct gatctacagg gcatccactc tgacatctgg ggtctcatcg        180
cggttcaaag gcagtggatc tgggacacag ttcactctca ccatcagcgg cgtggagtgt        240
gccgatgctg ccacttacta ctgtcaagag ggttatagtg atattaatgt taataatatt        300
ttcggcggag ggaccgaggt ggtggtcaaa                                          330

<210> SEQ ID NO 239
<211> LENGTH: 333
<212> TYPE: DNA
<213> ORGANISM: Artificial sequence
<220> FEATURE:
<223> OTHER INFORMATION: R166.A5 LCVR

<400> SEQUENCE: 239
```

-continued

```
gccaacatcg tgatgaccca gactccagcc tccgtgtctg agctgtgggg aggcacagtc       60
accatcaagt gccaggccag tcagagcatt agtacttatt tatcctggta tcagcagaaa      120
ccagggcagc ctcccaaact cctgatttac caggcatccg aattggcata tggggtctca      180
tcgcggttca aaggcagtgg atctgggaca gagttcactc tcaccatcag cggcgtggag      240
tgtgccgatg ctgccactta ctattgtcag cagggttata gtgatattaa tgtcgataat      300
tttttcggcg gagggaccga ggtggtggtc aaa                                   333
```

```
<210> SEQ ID NO 240
<211> LENGTH: 336
<212> TYPE: DNA
<213> ORGANISM: Artificial sequence
<220> FEATURE:
<223> OTHER INFORMATION: R166.H10 LCVR

<400> SEQUENCE: 240
```

```
gctgacattg tgatgaccca gactccagcc tccgtgtctg aacctgtggg aggcacagtc       60
accatcaatt gccaggccag tgaaagtatt tatagttggt tatcctggta tcaacagaaa      120
ccagggcagc ctcccaagct cctgatctat agtgcatcct atctggcatc tggcgtccca      180
tcacaattca gaggcagtgg atctgggaca gagtacactc tcaccatcag cgacctggag      240
tgtgccgatg ctgccactta ttactgtcaa tacaattatg atagtggtga tggtattact      300
aatggtttcg gcggagggac cgaggtggtg gtcaaa                                336
```

```
<210> SEQ ID NO 241
<211> LENGTH: 115
<212> TYPE: PRT
<213> ORGANISM: Artificial sequence
<220> FEATURE:
<223> OTHER INFORMATION: AS718 VHH

<400> SEQUENCE: 241
```

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Asp Ser Pro Ser Val Asn
            20                  25                  30

Tyr Met Gly Trp Phe Arg Arg Ala Pro Glu Lys Gln Arg Glu Glu Val
        35                  40                  45

Ala Ser Ile Tyr Pro Thr Gly Gly Thr Phe Tyr Thr Asp Ser Val Lys
    50                  55                  60

Gly Arg Phe Thr Ile Ser Arg Asp Asn Ala Lys Asn Thr Leu Tyr Leu
65                  70                  75                  80

Gln Met Thr Ala Leu Lys Pro Glu Asp Thr Ala Met Tyr Tyr Cys Ala
                85                  90                  95

Ala Gly Lys Trp Gly Thr Asp Tyr Trp Gly Gln Gly Thr Gln Val Ile
            100                 105                 110

Val Ser Ser
        115
```

```
<210> SEQ ID NO 242
<211> LENGTH: 323
<212> TYPE: PRT
<213> ORGANISM: Artificial sequence
<220> FEATURE:
<223> OTHER INFORMATION: HCCR

<400> SEQUENCE: 242
```

```
Gly Gln Pro Lys Ala Pro Ser Val Phe Pro Leu Ala Pro Cys Cys Gly
```

```
1                 5                10               15

Asp Thr Pro Ser Ser Thr Val Thr Leu Gly Cys Leu Val Lys Gly Tyr
              20               25               30

Leu Pro Glu Pro Val Thr Val Thr Trp Asn Ser Gly Thr Leu Thr Asn
              35               40               45

Gly Val Arg Thr Phe Pro Ser Val Arg Gln Ser Ser Gly Leu Tyr Ser
              50               55               60

Leu Ser Ser Val Val Ser Val Thr Ser Ser Ser Gln Pro Val Thr Cys
65                70               75               80

Asn Val Ala His Pro Ala Thr Asn Thr Lys Val Asp Lys Thr Val Ala
              85               90               95

Pro Ser Thr Cys Ser Lys Pro Thr Cys Pro Pro Pro Glu Leu Leu Gly
              100              105              110

Gly Pro Ser Val Phe Ile Phe Pro Pro Lys Pro Lys Asp Thr Leu Met
              115              120              125

Ile Ser Arg Thr Pro Glu Val Thr Cys Val Val Val Asp Val Ser Gln
              130              135              140

Asp Asp Pro Glu Val Gln Phe Thr Trp Tyr Ile Asn Asn Glu Gln Val
145              150              155              160

Arg Thr Ala Arg Pro Pro Leu Arg Glu Gln Gln Phe Asn Ser Thr Ile
              165              170              175

Arg Val Val Ser Thr Leu Pro Ile Ala His Gln Asp Trp Leu Arg Gly
              180              185              190

Lys Glu Phe Lys Cys Lys Val His Asn Lys Ala Leu Pro Ala Pro Ile
              195              200              205

Glu Lys Thr Ile Ser Lys Ala Arg Gly Gln Pro Leu Glu Pro Lys Val
              210              215              220

Tyr Thr Met Gly Pro Pro Arg Glu Glu Leu Ser Ser Arg Ser Val Ser
225              230              235              240

Leu Thr Cys Met Ile Asn Gly Phe Tyr Pro Ser Asp Ile Ser Val Glu
              245              250              255

Trp Glu Lys Asn Gly Lys Ala Glu Asp Asn Tyr Lys Thr Thr Pro Ala
              260              265              270

Val Leu Asp Ser Asp Gly Ser Tyr Phe Leu Tyr Ser Lys Leu Ser Val
              275              280              285

Pro Thr Ser Glu Trp Gln Arg Gly Asp Val Phe Thr Cys Ser Val Met
              290              295              300

His Glu Ala Leu His Asn His Tyr Thr Gln Lys Ser Ile Ser Arg Ser
305              310              315              320

Pro Gly Lys
```

```
<210> SEQ ID NO 243
<211> LENGTH: 969
<212> TYPE: DNA
<213> ORGANISM: Artificial sequence
<220> FEATURE:
<223> OTHER INFORMATION: HCCR

<400> SEQUENCE: 243
gggcaaccta aggctccatc agtcttccca ctggccccct gctgcgggga cacacccagc      60
tccacggtga ccctgggctg cctggtcaaa ggctacctcc cggagccagt gaccgtgacc     120
tggaactcgg gcaccctcac caatgggggta cgcaccttcc cgtccgtccg gcagtcctca     180
ggcctctact cgctgagcag cgtggtgagc gtgacctcaa gcagccagcc cgtcacctgc     240
```

```
aacgtggccc acccagccac caacaccaaa gtggacaaga ccgttgcgcc ctcgacatgc      300
agcaagccca cgtgcccacc ccctgaactc ctggggggac cgtctgtctt catcttcccc      360
ccaaaaccca aggacaccct catgatctca cgcaccccg aggtcacatg cgtggtggtg      420
gacgtgagcc aggatgaccc cgaggtgcag ttcacatggt acataaacaa cgagcaggtg      480
cgcaccgccc ggccgccgct acgggagcag cagttcaaca gcacgatccg cgtggtcagc      540
accctcccca tcgcgcacca ggactggctg aggggcaagg agttcaagtg caaagtccac      600
aacaaggcac tcccggcccc catcgagaaa accatctcca aagccagagg gcagcccctg      660
gagccgaagg tctacaccat gggccctccc cgggaggagc tgagcagcag gtcggtcagc      720
ctgacctgca tgatcaacgg cttctaccct tccgacatct cggtggagtg ggagaagaac      780
gggaaggcag aggacaacta caagaccacg ccggccgtgc tggacagcga cggctcctac      840
ttcctctaca gcaagctctc agtgcccacg agtgagtggc agcggggcga cgtcttcacc      900
tgctccgtga tgcacgaggc cttgcacaac cactacacgc agaagtccat ctcccgctct      960
ccgggtaaa                                                              969
```

<210> SEQ ID NO 244
<211> LENGTH: 104
<212> TYPE: PRT
<213> ORGANISM: Artificial sequence
<220> FEATURE:
<223> OTHER INFORMATION: LCCR

<400> SEQUENCE: 244

```
Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100
```

<210> SEQ ID NO 245
<211> LENGTH: 312
<212> TYPE: DNA
<213> ORGANISM: Artificial sequence
<220> FEATURE:
<223> OTHER INFORMATION: LCCR

<400> SEQUENCE: 245

```
ggtgatccag ttgcacctac tgtcctcatc ttcccaccag ctgctgatca ggtggcaact       60
ggaacagtca ccatcgtgtg tgtggcgaat aaatactttc cgatgtcac cgtcacctgg      120 gaggtggatg gcaccaccca aacaactggc atcgagaaca gtaaaacacc gcagaattct      180
gcagattgta cctacaacct cagcagcact ctgacactga ccagcacaca gtacaacagc      240
cacaaagagt acacctgcaa ggtgacccag ggcacgacct cagtcgtcca gagcttcaat      300
aggggtgact gt                                                          312
```

```
<210> SEQ ID NO 246
<211> LENGTH: 122
<212> TYPE: PRT
<213> ORGANISM: Artificial sequence
<220> FEATURE:
<223> OTHER INFORMATION: AS154 VHH

<400> SEQUENCE: 246

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser
        115                 120

<210> SEQ ID NO 247
<211> LENGTH: 121
<212> TYPE: PRT
<213> ORGANISM: Artificial sequence
<220> FEATURE:
<223> OTHER INFORMATION: AS325 VHH

<400> SEQUENCE: 247

Ala Val Gln Leu Val Glu Ser Gly Gly Gly Leu Val Gln Ala Gly Gly
1               5                   10                  15

Ser Leu Arg Leu Ser Cys Ile Ala Ser Gly Ile Glu Phe Thr Ile Gly
            20                  25                  30

Val Met Gly Trp Tyr Arg Gln Val Pro Gly Lys Glu Arg Glu Phe Val
        35                  40                  45

Ala Ala Ile Thr Asn Gly Gly Arg Pro Asn Tyr Ala Asp Ser Val Lys
    50                  55                  60

Gly Arg Phe Ala Ile Ser Arg Asp Asn Ala Lys Asn Thr Val Tyr Leu
65                  70                  75                  80

Leu Met Asn Ser Leu Lys Pro Glu Asp Thr Ala Val Tyr Tyr Cys Ala
                85                  90                  95

Leu Asp Arg Leu Phe Lys Ser Pro Asp Gly Leu Val Asp Tyr Trp Gly
            100                 105                 110

Gln Gly Thr Gln Val Thr Val Ser Leu
        115                 120

<210> SEQ ID NO 248
<211> LENGTH: 128
<212> TYPE: PRT
<213> ORGANISM: Artificial sequence
<220> FEATURE:
<223> OTHER INFORMATION: AS656 VHH

<400> SEQUENCE: 248

Glu Val Gln Leu Val Glu Ser Gly Gly Gly Leu Val Gln Val Gly Asp
```

-continued

```
1               5               10              15

Ser Leu Arg Leu Ser Cys Ala Ala Ser Gly Arg Ser Phe Glu Asn Tyr
            20              25              30

Ala Ile Gly Trp Phe Arg Gln Ala Pro Gly Lys Glu Arg Glu Phe Val
            35              40              45

Ala Thr Ile Ser Trp Ile Pro Arg Thr Ala Tyr Ser Thr Thr Tyr Tyr
        50              55              60

Ala Asp Ser Val Lys Gly Arg Phe Thr Ile Ser Gly Asp Asn Ser Lys
65              70              75              80

Asn Thr Val Tyr Leu Gln Met Thr Ser Leu Lys Pro Glu Asp Thr Ala
                85              90              95

Val Tyr Tyr Cys Ala Ala Gly Gly Ala Thr Gly Pro Leu Ala Leu Asp
                100             105             110

Ser His Tyr Gly Tyr Trp Gly Gln Gly Thr Gln Val Thr Val Ser Ser
            115             120             125
```

<210> SEQ ID NO 249
<211> LENGTH: 124
<212> TYPE: PRT
<213> ORGANISM: Artificial sequence
<220> FEATURE:
<223> OTHER INFORMATION: AS673 VHH

<400> SEQUENCE: 249

```
Gln Val Gln Leu Val Glu Ser Gly Gly Gly Leu Val Gln Ala Gly Gly
1               5               10              15

Ser Leu Arg Leu Ser Cys Ala Ala Ser Gly Arg Thr Phe Ile Thr Tyr
            20              25              30

Ala Ile Gly Trp Phe Arg Gln Ala Pro Gly Lys Glu Arg Glu Phe Val
            35              40              45

Ser Ala Ile Asn Trp Ser Gly Ser Met Thr Ser Tyr Ala Asp Ser Val
        50              55              60

Lys Gly Arg Phe Thr Ile Ser Arg Asp Asn Ala Lys Asn Thr Val Tyr
65              70              75              80

Leu Gln Met Asn Gly Leu Lys Pro Glu Asp Thr Ala Val Tyr Tyr Cys
                85              90              95

Ala Ala His Arg Gly Ala Ile Ala Pro Ile Ala Gln Ser Val Tyr Thr
            100             105             110

Asn Trp Gly Gln Gly Thr Gln Val Thr Val Ser Ser
            115             120
```

<210> SEQ ID NO 250
<211> LENGTH: 116
<212> TYPE: PRT
<213> ORGANISM: Artificial sequence
<220> FEATURE:
<223> OTHER INFORMATION: AS587 VHH

<400> SEQUENCE: 250

```
Gln Val Gln Leu Val Glu Ser Gly Gly Gly Leu Val Gln Pro Gly Gly
1               5               10              15

Ser Leu Thr Leu Ser Cys Ala Ala Ser Gly Phe Thr Phe Ser Thr Ala
            20              25              30

Ala Met Ser Trp Val Arg Gln Val Pro Glu Glu Gly Leu Glu Trp Val
            35              40              45

Ala Ser Ile Asp Ser Ser Gly Ser Arg Thr Tyr Tyr Ala Gly Ser Val
        50              55              60
```

-continued

```
Lys Gly Arg Phe Thr Ile Ser Arg Asp Asn Ala Lys Asn Thr Leu Tyr
65                  70                  75                  80

Leu Gln Leu Asn Ser Leu Lys Ala Glu Asp Thr Ala Met Tyr Tyr Cys
                85                  90                  95

Ala Lys Asp His Met Ser Trp Leu Pro Arg Gly Gln Gly Thr Gln Val
            100                 105                 110

Thr Val Ser Ser
            115

<210> SEQ ID NO 251
<211> LENGTH: 122
<212> TYPE: PRT
<213> ORGANISM: Artificial sequence
<220> FEATURE:
<223> OTHER INFORMATION: AS588 VHH

<400> SEQUENCE: 251

Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Thr Asp Ser Ser Tyr
                20                  25                  30

Cys Gly Ala Trp Phe Arg Gln Val Pro Gly Lys Glu Arg Glu Gly Val
            35                  40                  45

Ala Ile Ile Asp Arg Tyr Gly Gly Thr Met Tyr Lys Asp Ser Val Lys
        50                  55                  60

Gly Arg Phe Thr Ile Ser Lys Asp Thr Ala Lys Asn Ile Leu Tyr Leu
65                  70                  75                  80

Gln Met Asn Ser Leu Lys Leu Glu Asp Thr Ala Met Tyr Tyr Cys Ala
                85                  90                  95

Ala Ala Glu Tyr Arg Gly Ser Ser Cys Asp Ala Glu Ser Gly Tyr Trp
            100                 105                 110

Gly Gln Gly Thr Gln Val Thr Val Ser Ser
            115                 120

<210> SEQ ID NO 252
<211> LENGTH: 124
<212> TYPE: PRT
<213> ORGANISM: Artificial sequence
<220> FEATURE:
<223> OTHER INFORMATION: AS200 VHH

<400> SEQUENCE: 252

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Leu Ser Tyr
                20                  25                  30

Ala Val Gly Trp Phe Arg Gln Ala Pro Gly Thr Glu Arg Glu Phe Val
            35                  40                  45

Ala Gly Ile Arg Trp Ser Gly Gly Ser Thr Asp Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Arg Thr Ile Ala Thr Val Pro Asn Lys Tyr Glu Tyr Asp
            100                 105                 110

Thr Trp Gly Gln Gly Thr Gln Val Thr Val Ser Ser
            115                 120
```

```
<210> SEQ ID NO 253
<211> LENGTH: 125
<212> TYPE: PRT
<213> ORGANISM: Artificial sequence
<220> FEATURE:
<223> OTHER INFORMATION: AS988 VHH

<400> SEQUENCE: 253

Gln Val Gln Leu Ala Glu Ser Gly Gly Gly Ser Val Gln Thr Gly Gly
1               5                   10                  15

Ser Leu Arg Leu Ser Cys Glu Ala Ser Gly Val Ala Ala Ser Gly Tyr
            20                  25                  30

Cys Met Ala Trp Phe Arg Gln Ala Pro Gly Lys Glu Arg Glu Arg Val
        35                  40                  45

Ala Ala Ile Ser Ser Asn Asp Leu Val Ala Tyr Ala Asp Ser Val Lys
    50                  55                  60

Gly Arg Phe Thr Ile Ser Lys Asp Asn Ala Lys Thr Thr Leu Tyr Leu
65                  70                  75                  80

Gln Met Asn Asn Leu Lys Pro Glu Asp Thr Ala Met Tyr Tyr Cys Ala
                85                  90                  95

Ala Asp Gly Gly Tyr Gly Gly Tyr Cys Gly Arg Leu Arg Pro Gly Thr
            100                 105                 110

Gly Tyr Trp Gly Gln Gly Thr Gln Val Thr Val Ser Ser
            115                 120                 125

<210> SEQ ID NO 254
<211> LENGTH: 124
<212> TYPE: PRT
<213> ORGANISM: Artificial sequence
<220> FEATURE:
<223> OTHER INFORMATION: AS675 VHH

<400> SEQUENCE: 254

Ala Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Leu Thr Tyr
            20                  25                  30

Ala Val Gly Trp Phe Arg Gln Ala Pro Gly Thr Glu Arg Glu Phe Val
        35                  40                  45

Ala Gly Ile Arg Trp Ser Gly Gly Tyr Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Arg Thr Ile Ala Thr Ile Pro Glu Lys Tyr Glu Tyr Glu
            100                 105                 110

Tyr Trp Gly Gln Gly Thr Gln Val Thr Val Ser Ser
            115                 120

<210> SEQ ID NO 255
<211> LENGTH: 123
<212> TYPE: PRT
<213> ORGANISM: Artificial sequence
<220> FEATURE:
<223> OTHER INFORMATION: AS519 VHH

<400> SEQUENCE: 255
```

-continued

```
Gln Ile Gln Leu Val Glu Ser Gly Gly Gly Ser Ala Gln Ala Gly Gly
1               5                   10                  15

Ser Leu Arg Leu Ser Cys Val Val Ser Gly Asn Ile Tyr Asn Arg Asn
            20                  25                  30

Phe Met Gly Trp Phe Arg Gln Ala Pro Gly Lys Val Arg Glu Gly Val
            35                  40                  45

Ala Ala Ile Tyr Thr Gly Thr Ser Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Gln Val Thr Val Ser Ser
            115                 120
```